(12) United States Patent
Branch et al.

(10) Patent No.: US 9,289,157 B2
(45) Date of Patent: Mar. 22, 2016

(54) ROBOTIC KNEE TESTING DEVICE, SUBJECTIVE PATIENT INPUT DEVICE AND METHODS FOR USING SAME

(75) Inventors: Thomas P Branch, Atlanta, GA (US); Thomas Cunningham, Atlanta, GA (US); Edward Dittmar, Marietta, GA (US); Cale Jacobs, Suwanee, GA (US)

(73) Assignee: ERML Inc., Atlanta, GA (US)

( * ) Notice: Subject to any disclaimer, the term of this patent is extended or adjusted under 35 U.S.C. 154(b) by 31 days.

(21) Appl. No.: 13/209,380

(22) Filed: Aug. 13, 2011

(65) Prior Publication Data

US 2012/0046540 A1 Feb. 23, 2012

Related U.S. Application Data

(60) Provisional application No. 61/373,643, filed on Aug. 13, 2010, provisional application No. 61/377,688, filed on Aug. 27, 2010, provisional application No. 61/513,926, filed on Aug. 1, 2011.

(51) Int. Cl.
*A61B 5/103* (2006.01)
*A61B 5/00* (2006.01)
*A61B 5/11* (2006.01)

(52) U.S. Cl.
CPC .................. *A61B 5/1036* (2013.01); *A61B 5/11* (2013.01); *A61B 5/1127* (2013.01); *A61B 5/1128* (2013.01); *A61B 5/4528* (2013.01); *A61B 5/4538* (2013.01); *A61B 5/4585* (2013.01);
(Continued)

(58) Field of Classification Search
USPC ........................................ 600/587, 595; 601/5
See application file for complete search history.

(56) References Cited

U.S. PATENT DOCUMENTS

| T100,602 I4 | 5/1981 | Roley et al. |
| 4,294,141 A | 10/1981 | Miller |
| 4,407,277 A | 10/1983 | Ellison |

(Continued)

FOREIGN PATENT DOCUMENTS

| CA | 2615171 | 1/2007 |
| DE | 36 09 535 | 9/1987 |

(Continued)

OTHER PUBLICATIONS

Office Action dated Feb. 7, 2012 in U.S. Appl. No. 12/267,109, filed Nov. 7, 2008.

(Continued)

*Primary Examiner* — Sean Dougherty
(74) *Attorney, Agent, or Firm* — Gronholm Patent Services, LLC

(57) ABSTRACT

An apparatus for evaluating leg movement characteristics of a patient is provided. The apparatus comprises a base assembly configured to at least partially support the patient's torso; and first and second leg support assemblies independently pivotably mounted about a pivot axis relative to the base assembly. Each leg support assembly is configured to at least partially support a portion of a respective one of the first and second legs, independent of the support of the torso. Each of the leg support assemblies also comprises: a first leg support member including a foot rotation assembly configured to at least partially retain and support an associated foot of the patient and to rotate it about an axis of rotation relative to the base assembly; and a second leg support member configured for supporting a portion of the leg at a location proximal relative to the first leg support member.

27 Claims, 36 Drawing Sheets

(52) U.S. Cl.
CPC ............ *A61B 5/6828* (2013.01); *A61B 5/6829* (2013.01); *A61B 5/702* (2013.01)

(56) References Cited

U.S. PATENT DOCUMENTS

| | | | |
|---|---|---|---|
| 4,586,495 A | 5/1986 | Petrofsky | |
| 4,650,183 A | 3/1987 | McIntyre | |
| 4,727,860 A * | 3/1988 | McIntyre | A61B 5/103 482/112 |
| 4,733,859 A | 3/1988 | Kock et al. | |
| 4,771,548 A | 9/1988 | Donnery | |
| 4,782,831 A | 11/1988 | Gallant | |
| 4,823,807 A | 4/1989 | Russell et al. | |
| 4,825,852 A | 5/1989 | Genovese et al. | |
| 4,834,073 A | 5/1989 | Bledsoe et al. | |
| 4,909,262 A * | 3/1990 | Halpern | A61B 5/1107 33/512 |
| 4,930,497 A | 6/1990 | Saringer | |
| 5,027,799 A | 7/1991 | Laico et al. | |
| 5,056,535 A | 10/1991 | Bonnell | |
| 5,211,161 A | 5/1993 | Stef | |
| 5,228,432 A | 7/1993 | Kaiser et al. | |
| 5,228,454 A * | 7/1993 | Siegler | A61B 5/103 600/592 |
| 5,335,674 A | 8/1994 | Siegler | |
| 5,382,225 A | 1/1995 | Sutcliffe | |
| 5,399,147 A | 3/1995 | Kaiser | |
| 5,402,800 A | 4/1995 | Hollis | |
| 5,435,321 A | 7/1995 | McMillen et al. | |
| 5,645,079 A | 7/1997 | Zahiri et al. | |
| 4,278,860 A | 3/1998 | McIntyre | |
| 6,599,255 B2 | 7/2003 | Zhang | |
| 6,669,660 B2 | 12/2003 | Branch | |
| 6,821,231 B1 | 11/2004 | Hall | |
| 6,872,186 B2 | 3/2005 | Branch et al. | |
| 7,041,069 B2 | 5/2006 | West | |
| 7,479,121 B2 | 1/2009 | Branch | |
| 7,547,289 B2 | 6/2009 | Branch | |
| 7,628,766 B1 * | 12/2009 | Kazerooni et al. | 602/16 |
| 7,665,167 B2 * | 2/2010 | Branch et al. | 5/624 |
| 7,753,862 B2 | 7/2010 | Branch et al. | |
| 7,854,685 B2 * | 12/2010 | Cole et al. | 482/5 |
| 7,951,097 B2 * | 5/2011 | Schaeffer | 601/5 |
| 7,985,227 B2 * | 7/2011 | Branch et al. | 606/88 |
| 2004/0260208 A1 | 12/2004 | Laprade et al. | |
| 2005/0222573 A1 * | 10/2005 | Branch et al. | 606/86 |
| 2006/0064048 A1 | 3/2006 | Stano | |
| 2006/0097557 A1 | 5/2006 | Tholkes et al. | |
| 2007/0055176 A1 | 3/2007 | Branch et al. | |
| 2007/0123997 A1 | 5/2007 | Herr et al. | |
| 2008/0216570 A1 * | 9/2008 | Andres | A61B 5/1071 73/379.01 |
| 2009/0124936 A1 | 5/2009 | Branch et al. | |
| 2009/0264797 A1 | 10/2009 | Mayr | |
| 2010/0179605 A1 * | 7/2010 | Branch et al. | 606/86 R |
| 2011/0218461 A1 * | 9/2011 | Cugat Bertomeu | A61B 5/1071 600/595 |
| 2012/0046540 A1 * | 2/2012 | Branch et al. | 600/415 |
| 2012/0085353 A1 | 4/2012 | Siston | |

FOREIGN PATENT DOCUMENTS

| | | |
|---|---|---|
| DE | 39 25 014 | 1/1991 |
| DE | 3925014 A1 | 1/1991 |
| EP | 0 204 639 | 12/1986 |
| EP | 0293372 | 6/1991 |
| EP | 1 219 240 | 7/2002 |
| WO | WO 88/04536 A1 | 6/1988 |
| WO | WO 8804536 | 6/1988 |
| WO | WO 9302621 | 2/1993 |
| WO | WO 02/096274 | 12/2002 |
| WO | WO 2007/009063 | 1/2007 |
| WO | WO 2009/064367 | 5/2009 |
| WO | WO 2012021726 A1 | 2/2012 |

OTHER PUBLICATIONS

Office Action dated Dec. 9, 2011 in U.S. Appl. No. 12/797,324, filed Jun. 9, 2010.
European Patent Office, Office Action dated Apr. 4, 2012, for Application No. EP06787304.2.
United States Patent and Trademark Office, Office Action for U.S. Appl. No. 12/267,109, dated Mar. 13, 2013, 28 pages, USA.
International Preliminary Examining Authority, Written Opinion for International Application No. PCT/US2011/047696, mailed Aug. 3, 2012, 8 pages, European Patent Office, The Netherlands.
United States Patent and Trademark Office, Office Action for U.S. Appl. No. 12/797,324, dated Oct. 1, 2012, 9 pages, USA.
B.D. Beynnon et al., "The Effect of Functional Knee-Braces on Strain on the Anterior Cruciate Ligament In Vivo," Journal of Bone and Joint Surgery; Boston, US; vol. 74A, No. 9; Oct. 1, 1992; pp. 1298-1312; XP00322579.
Daniel, "MEDmetric® Knee Ligament Arthrometer ModelsKT1000™ and KT1000™," Reference, Maintenance and User guide for the Knee Ligament Arthrometer®, 1$^{st}$ Ed., May 1993, 51 pp. San Diego, CA.
International Search Report for International Application No. PCT/US2006/027376 filed Apr. 19, 2007.
International Search Report from corresponding International Application No. PCT/US2008/012578 received Aug. 11, 2009.
Invitation to Pay Additional Fees and, where Applicable, Protest Fee Search Report for International Application No. PCT/US2008/012578 received Apr. 17, 2009.
Li-Wun Zhang et al., "Dynamic and Static Properties of The Human Knee Joint in Axial Rotation," Engineering in Medicine and Biology Society, 1997, Proceedings of the 19th Annual International Conference of the IEEE Chicago, IL, USA Oct. 30-Nov. 2, 1997; Piscataway, NJ, USA, IEEE, US; vol. 4; Oct. 30, 1997; pp. 1738-1741; XP010325504.
Markolf, K. L., et al., "In vivo knee stability. A quantitative assessment using an instrumented clinical testing apparatus," Journal of Bone and Joint Surgery, American Volume Jul. 1978, vol. 60, No. 5, Jul. 1978, XP002515912, ISSN: 0021-9355, p. 664-p. 674.
Medmetric Corporation, "In These Times of Managed Care, Measured Outcomes are Crucial," found at http://web.archive.org/web120040610111553/http://medmetric.com (1 page).
Medmetric Corporation, "KT1000/S;" found at http://web.archive.org/web/20040628060104/www.kt1000.com/kts.htm (2 pages).
Medmetric Corporation, "KT2000," found at http://web.archive.org/web/20040618192953/www.kt1000.com/kts.htm (2 pages).
Notice of Allowance dated Mar. 9, 2010, U.S. Appl. No. 11/457,443, filed Jul. 13, 2006.
Office Action dated Aug. 6, 2009, U.S. Appl. No. 11/457,443, filed Jul. 13, 2006.
Roley et al., "T100,602—Apparatus for Measuring Angles," United States Defensive Publication, May 5, 1981; 5 pages.
S.C. Shoemaker et al., "In-Vivo Rotatory Knee Stability Ligamentous and Muscular Contributions," Journal of Bone and Joint Surgery; Boston, US; vol. 64, No. 2; 1982; pp. 208-216; XP008050394.
Shino, K. et al., "Measurement of anterior instability of the knee. A new apparatus for clinical testing," The Journal of Bone and Joint Surgery, British Volume, Aug. 1987, vol. 69, No. 4, Aug. 1987, XP002515908; ISSN: 0301-620X, p. 608-p. 613.
Shultz Sandra, J., et al., "Measurement of varus-valgus and internal-external rotational knee laxities in vivo—Part I: assessment of measurement reliability and bilateral asymmetry," Journal of Orthopaedic Research: Official Publication of the Orthopaedic Research Society, Aug. 2007, vol. 25, No. 8, XP002515908, ISSN: 0736-0266, p. 981-p. 988.
Uh B.S., et al., "A new device to measure knee laxity during weightbearing and non-weightbearing conditions," Journal of Orthopaedic Research: Official Publication of the Orthopaedic Research Society Nov. 2001, vol. 19, No. 6, Nov. 2001, XP002515911; ISSN: 0736-0266, p. 1185-p. 1191.

(56) References Cited

OTHER PUBLICATIONS

Van Der Esch, M. et al., "Reproducibility of instrumented knee joint laxity measurement in healthy subjects," Rheumatology (Oxford, England) May 2006, vol. 45, No. 5, pp. 595-599, XP002515910; ISSN: 1462-0324.

International Search Report and Written Opinion of the International Searching Authority dated Nov. 17, 2011, for Application No. PCT/US2011/047696.

Branch, et al. "Instrumented Examination of Anterior Cruciate Ligament Injuries: Minimizing Flaws of the Manual Clinical Examination," *Arthroscopy*, vol. 26, No. 7, Jul. 2010, pp. 997-1004.

Office Action dated Dec. 9, 2011 for Application No. 12/797,324, filed Jun. 9, 2010.

International Searching Authority, ISR and Written Opinion for International Appn No. PCT/US2013/060229, mailed Dec. 5, 2013, 12 pages, EPO, The Netherlands.

Oct. 8, 2015 Examination Report in European Patent Application No. 11764624.0, EPO, Netherlands, 6 pages.

\* cited by examiner

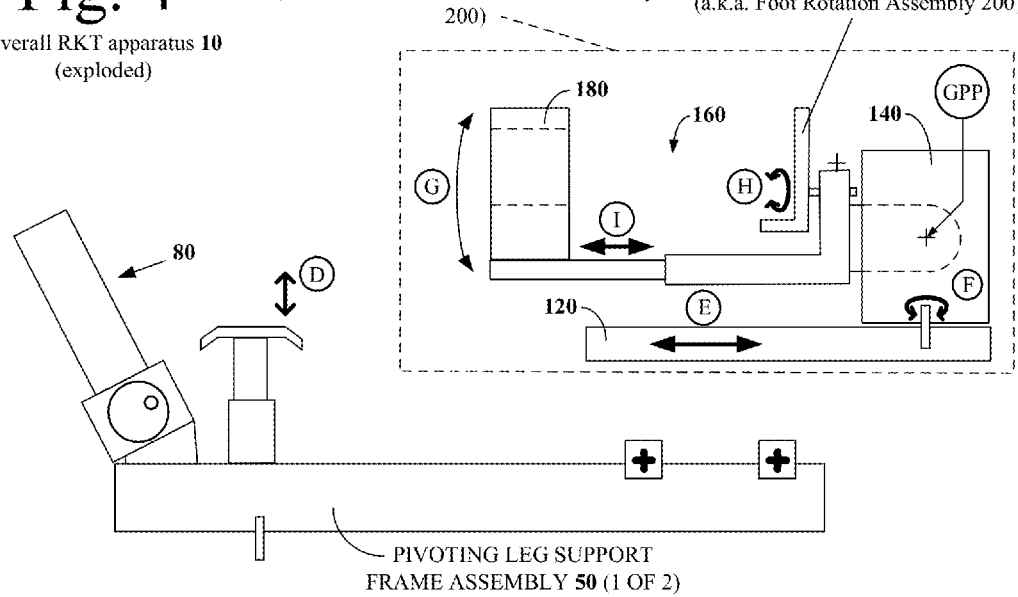
Fig. 4
Overall RKT apparatus 10 (exploded)
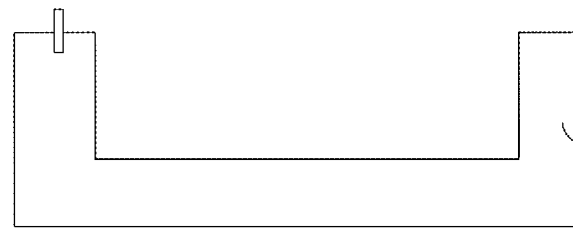
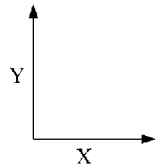

Fig. 8 — Left Tibia Positioning Assembly shown at an angle (pivoted according to Action "B")

Fig. 9 LEFT PIVOTING LEG SUPPORT FRAME ASSEMBLY 50 MORE EXTENDED THAN THE RIGHT ONE

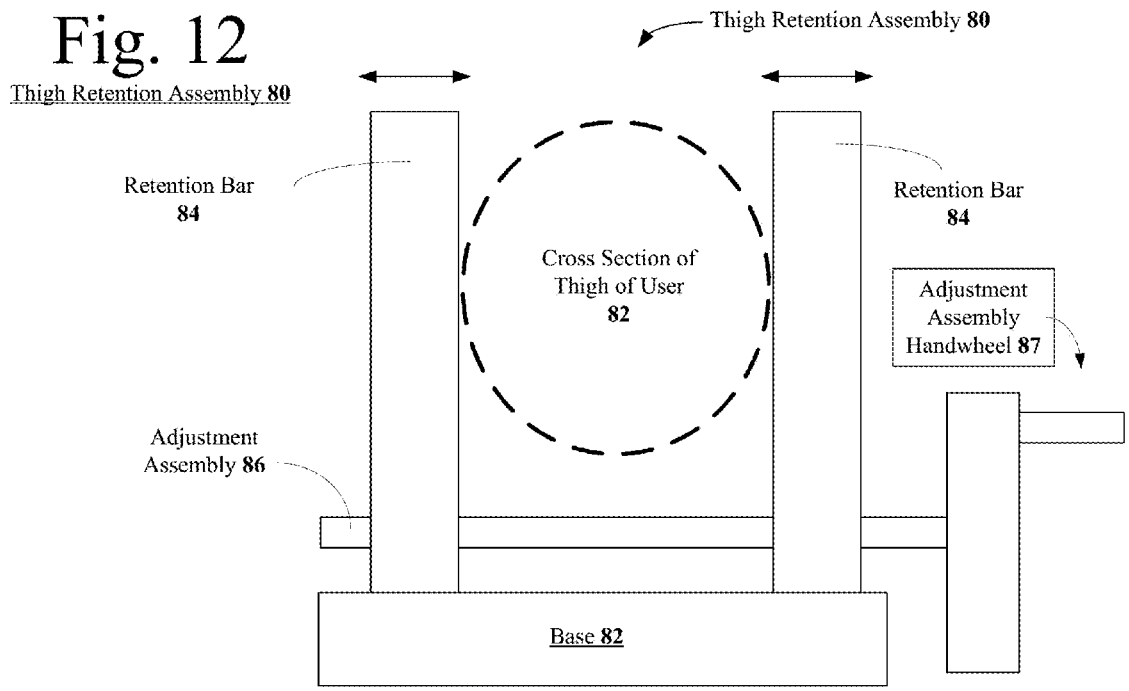

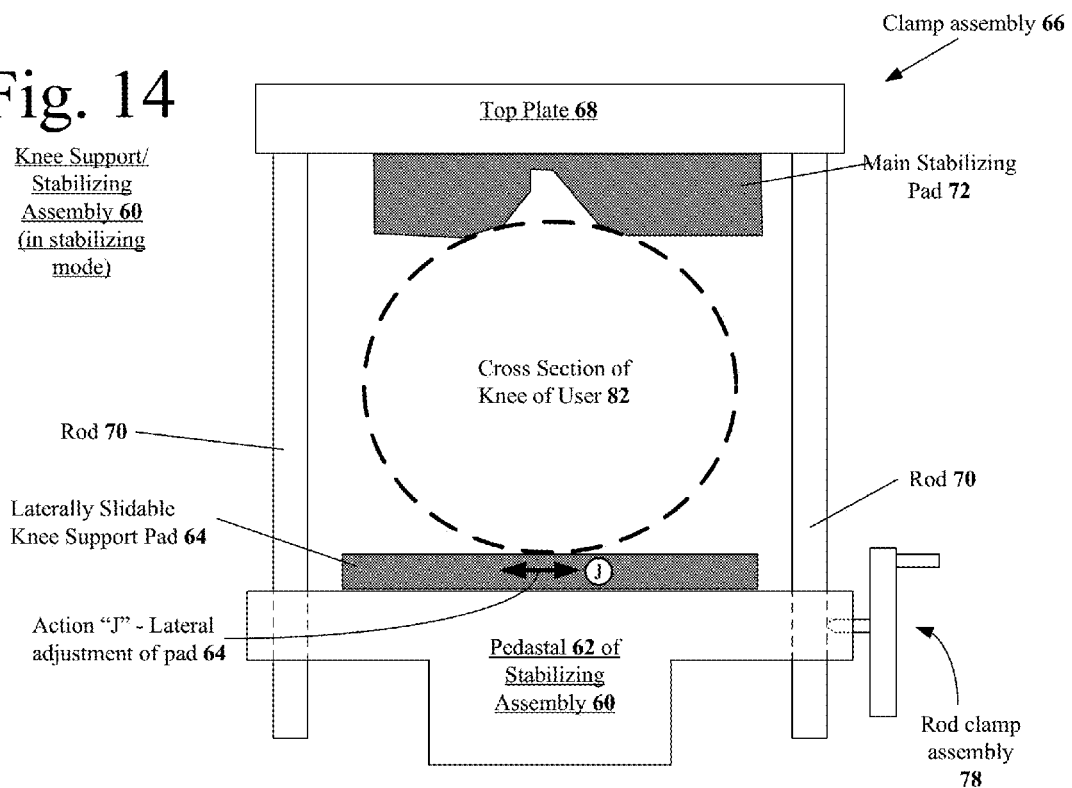
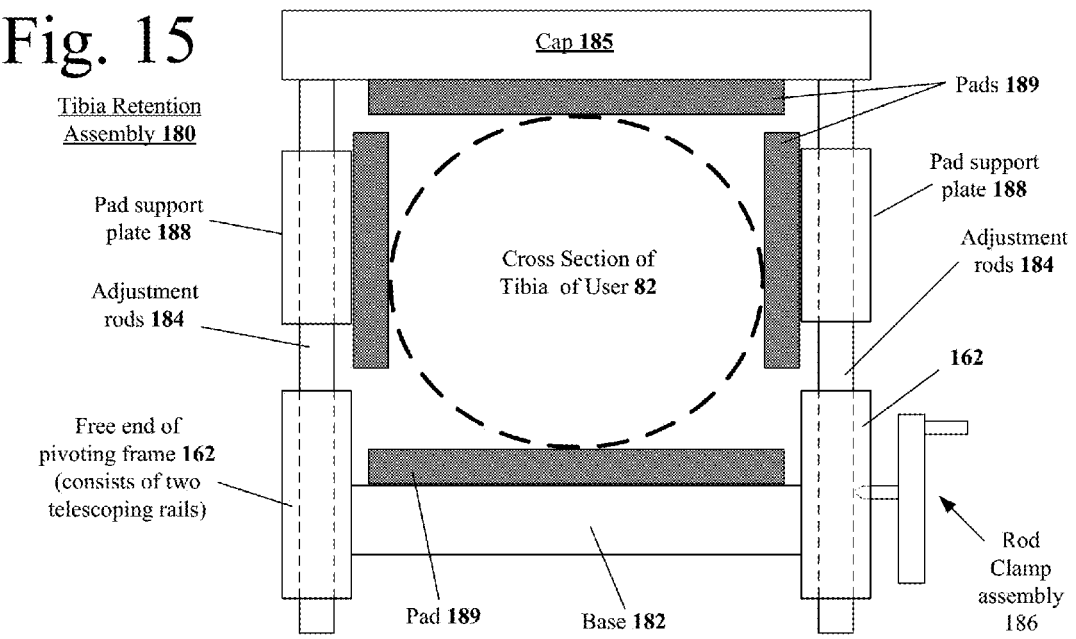

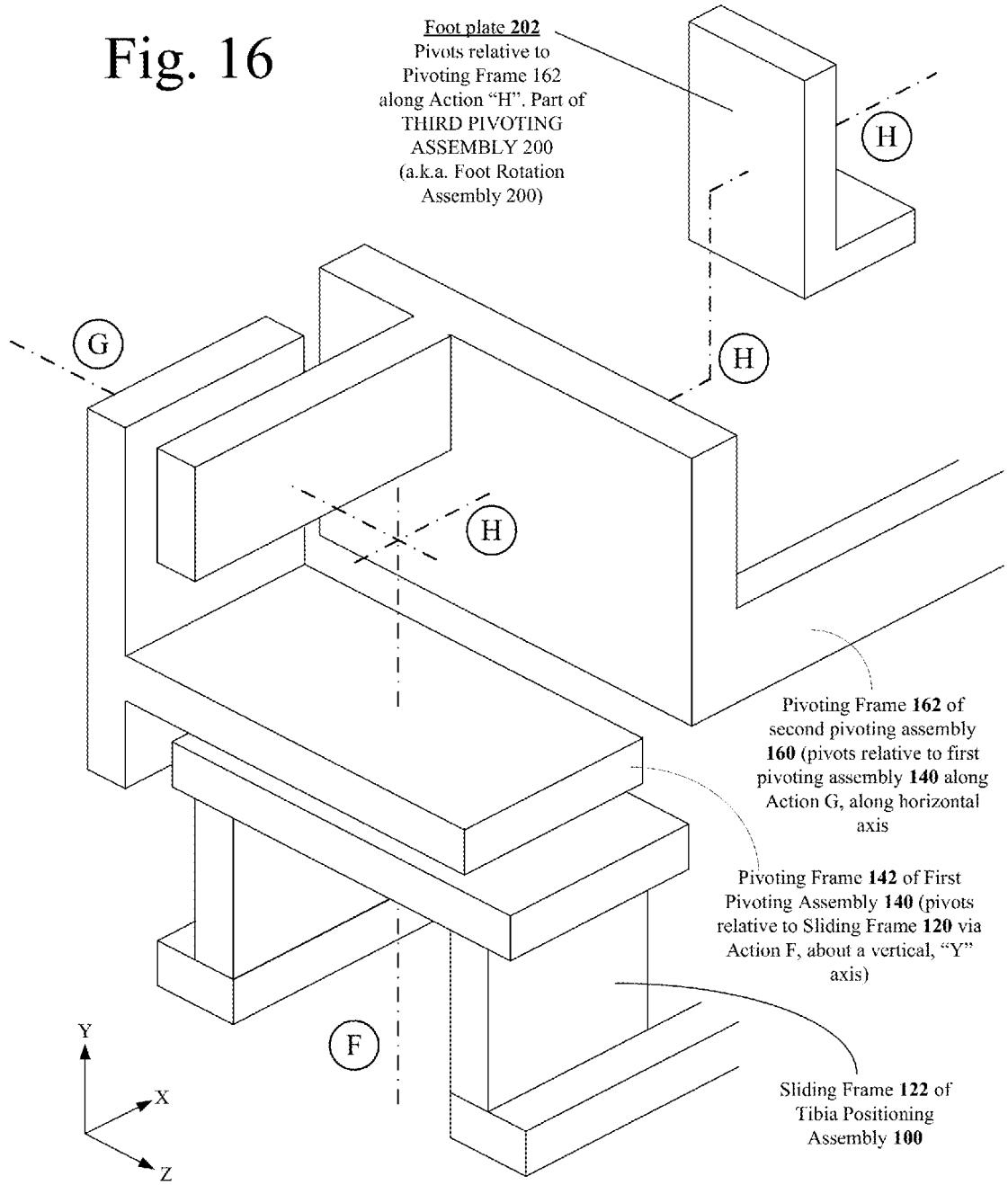

Fig. 17   Subjective Measurement Module 2000
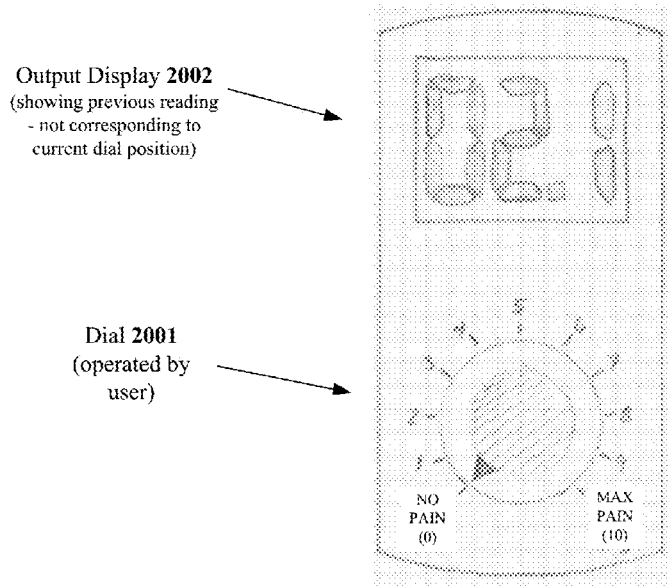
Output Display 2002
(showing previous reading
- not corresponding to
current dial position)
Dial 2001
(operated by
user)
Fig. 18   Subjective Measurement Module 2200
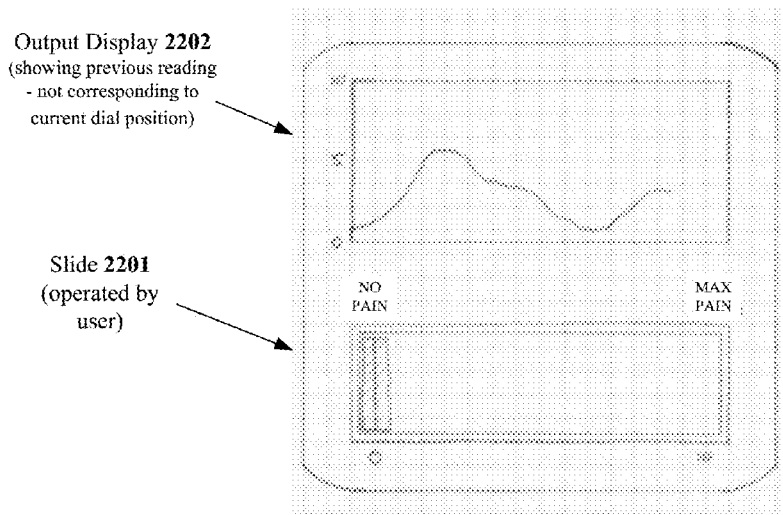
Output Display 2202
(showing previous reading
- not corresponding to
current dial position)
Slide 2201
(operated by
user)

Similar to Figure 20 but without Knee Support Stabilizing Assemblies 60

Same as Figure 23 but More Approximating a Side Elevational View

Slight overhead view from foot of device, shown without Knee Support Stabilizing Assemblies 60

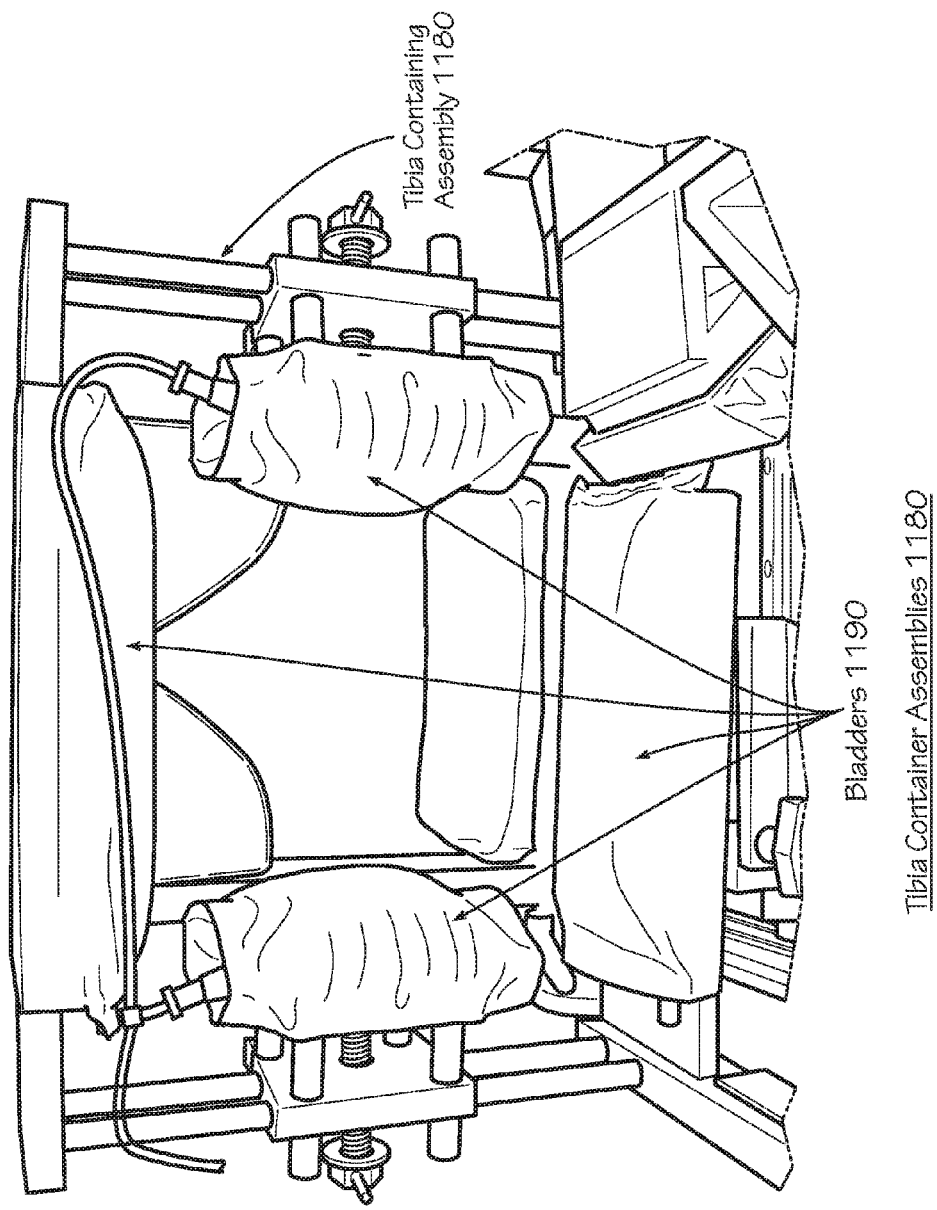

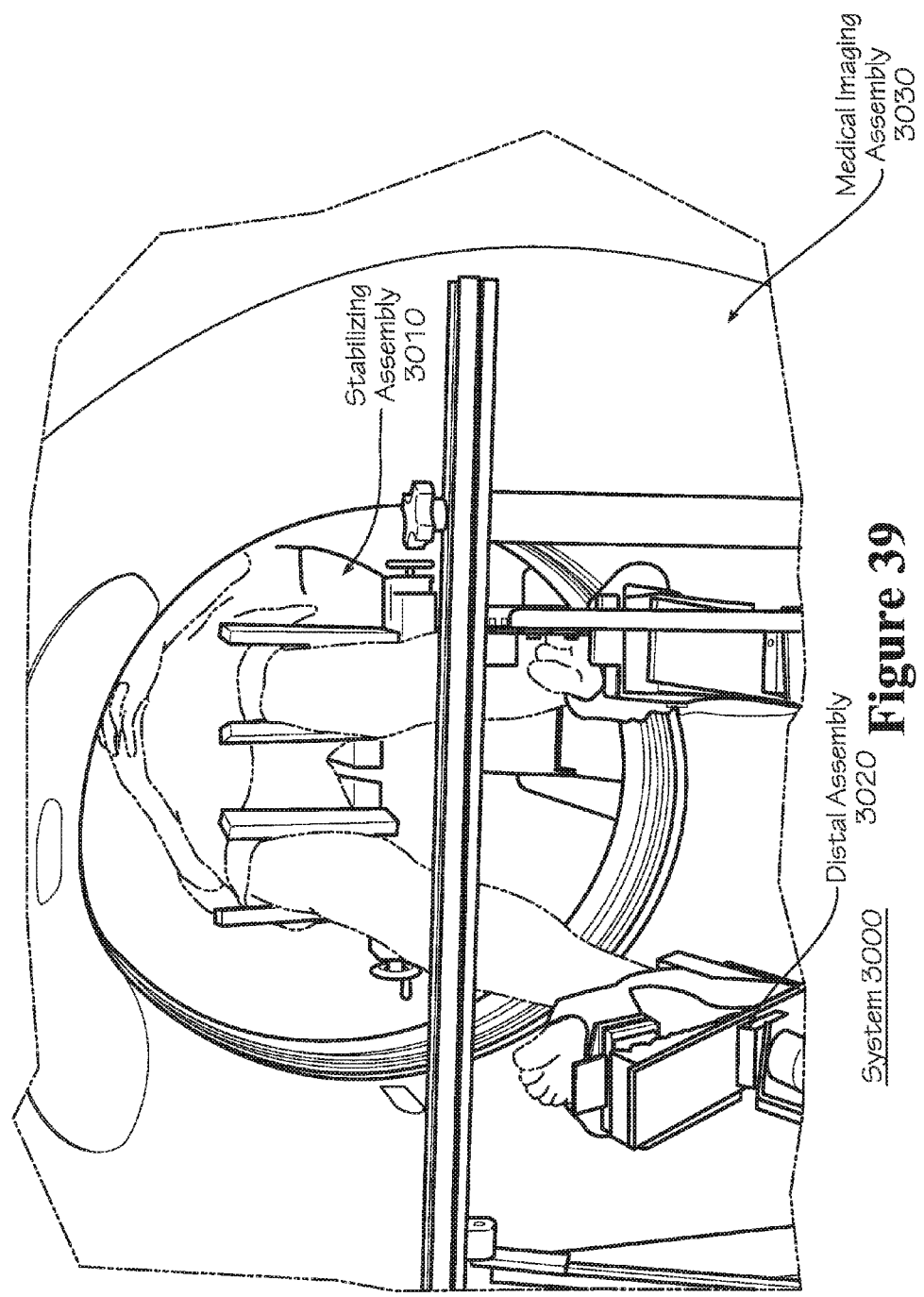

ROBOTIC KNEE TESTING DEVICE, SUBJECTIVE PATIENT INPUT DEVICE AND METHODS FOR USING SAME

CROSS-REFERENCE TO RELATED APPLICATIONS

This application claims priority to and the benefit of U.S. Provisional Application No. 61/373,643, filed Aug. 13, 2010, entitled "Robotic Knee Testing Device, Subjective Patient Input Device, and Method for Using the Same," U.S. Provisional Application No. 61/377,688, filed Aug. 27, 2010, entitled "Robotic Knee Testing Device, Subjective Patient Input Device, Bladder Driven Linear Actuator, and Methods for Using the Same," and U.S. Provisional Application No. 61/513,926, filed Aug. 1, 2011, entitled "Pivotometer Used with CT Scanner or Other Imaging," all of which are incorporated herein in their entirety.

BACKGROUND

1. Field of Invention

This generally relates to three-dimensional joint motion evaluation using medical imaging and computer-controlled torque application via, for example, a robotic knee device (an "RKT" device) which controls the direction, rate, and magnitude of forces applied in at least three directions, namely a flexion or extension force in an x-axis of rotation, a varus or valgus force in a z-axis of rotation, and an internal or external rotation force in a y-axis rotation, any of which while also permitting a patient to input a subjective pain measurement in response to the same.

2. Description of Related Art

The knee is composed of the femur or thigh bone, the tibia or shin bone and the patella or knee cap. They are connected by fibrous structures called ligaments which allow a certain amount of 'joint play' or motion to exist between the bone structures. When this 'joint play' is increased or decreased, an abnormal or pathological condition exists in the knee. Attempts have been made in the past to quantify this increase or decrease in 'joint play' of the knee with limited success.

An injury to the knee can cause damage to one or more of the structures of the knee causing an increase in the 'joint play' or motion of the knee. This increase in 'joint play' can create the sensation to the patient that the knee is slipping or 'coming out of joint'. Commonly, this sensation described by the patient is referred to as the feeling of 'joint instability'. The ability of the two bones to actually 'come out of joint' is related to the length of the fibrous structures or ligaments which connect the two bones together as well as the shape and size of the two bones (or three). The ability of the bones to 'come out of joint' or become unstable is related to the amount of stretch or the amount of increased lengthening of each ligament, the number of ligaments involved, and damage to other support structures of the knee such as the bone itself and the menisci. Accurate measurement of this increased ligament length can be critical to restore the knee to as close to its original functional and anatomical state as possible.

Currently, there are only manual tests used by clinicians to aid in the diagnosis of ligament damage or increased (decreased) joint play. As an example, there are three manual tests to evaluate the increased joint play associated with an ACL tear—the Lachman's test, the Pivot Shift test and the Anterior Drawer Test. All of these tests suffer from the clinician's subjective evaluation of both the extent of the ligament lengthening and the change in the compliance or stretchiness of the ligament.

The Lachman's test is performed by laying the patient in a supine position and bending the knee at approximately 20 to 30 degrees. The clinician places a hand on the patient's upper thigh and his other hand below the upper part of the patient's calf muscle. Pressure is applied under the patient's calf and down on the patient's thigh such that translation between the tibia and femur occurs.

Similar to the Lachman's test, the pivot shift test begins by positioning the patient on his back. The knee is flexed (x-axis rotation) and a valgus (z-axis rotation) force and an internal rotation (y-axis rotation) force is applied to the knee as the knee is brought into full extension (x-axis rotation). The clinician feels for an abnormal internal rotation (y-axis rotation) and anterior translation (z-axis translation) of the tibia with respect to the femur. This shift is felt to represent the relative increased translation (z-axis translation) of the lateral side of the knee with respect to the increased translation (z-axis translation) of the medial side of the knee. Furthermore, the point of sudden shift represents the point at which the back part of the tibia bone slides in front of the radius of curvature of the curved end of the femur. The clinician subjectively rates the pivot shift as Grade I, Grade II or Grade III depending upon the degree of rotational and translational shift felt during the test. This test is difficult to perform, difficult to teach and difficult to quantify.

Finally, the anterior drawer test is performed with the patient lying on his back and his knee bent to 90 degrees. With the patient's foot supported by a table or chair, the clinician applies pressure to the knee using her thumbs. This test is graded based upon the amount or extent of anterior translation along the z-axis of the tibia with respect to the femur. Grade I has 0 to 5 mm of anterior translation (z-axis translation), Grade II has 6 to 10 mm of anterior translation, and Grade III has 11 to 15 mm of translation.

To diagnose an injured ACL using the described tests, the clinician must determine whether the knee feels "abnormal." Thus, the accuracy of an ACL injury diagnosis using currently known tests depends on the skill and experience of the clinician. A misdiagnosis can lead to unnecessary delay in treatment, thereby placing the patient at increased risk for further damage to the knee.

There are manual tests for the LCL, MCL and the PCL. Each manual test relies on grading the extent of the ligament lengthening into three categories. There is no effort to grade the compliance of the ligament; however, the expert clinician will describe the ligament in terms of its 'feel'. The more ligaments and structures that are damaged; the more complex it becomes to perform a knee examination using the subjective manual exams.

There have been multiple attempts in the past to instrument the knee and quantify or measure the change in the structure of the knee after ligament damage. Several devices have attempted to accurately quantify the extent or relative displacement and compliance of a ligament in the knee. One of these devices is The KT-1000 and the KT-2000 Medmetric®, which measures the anterior-posterior translation of the tibia with respect to the femur along the z-axis, but disadvantageously attach to the tibia. These devices attempt to quantify the findings found when the clinician uses the Lachman's test and the Anterior Drawer Test. Force is applied to a handle on the device which measures force and signals to the clinician the amount of force with a low pitched sound for the 15 pound force, a higher pitched sound for the 20 pound force. This force pulls anteriorly along the z-axis through a strap that wraps underneath the calf. The measurement of the translation uses a technique measuring the relative motion of a pad on the anterior tibia with respect to a pad placed on the patella.

This device does not measure relative displacement or compliance in any of the other degrees of freedom previously described in the knee. Furthermore, the quantified results of the KT-1000 or KT-2000 have not been correlated with patient satisfaction whereas the subjective Pivot Shift test has been correlated with patient satisfaction. Other devices such as the Stryker KLT, the Rolimeter, and the KSS system use similar mechanisms to attempt to quantify the normal amount of 'joint play' or motion between two bones, along with any increased 'joint play' or motion associated with damage to the ligaments.

Many non-invasive systems utilize sensors or markers that are attached to the skin, including but not limited to optoelectronic, ultrasonic, and electromagnetic motion analysis systems. These skin sensors or markers are merely representations of location of the underlying bones; however, many published reports have documents the measurement error related to skin artifact with this system. In order to avoid the inaccuracies associated with skin artifact, medical imaging systems must be utilized in order to precisely determine of the bones.

Surgeons manually examine the joint for altered play; however, due to the variability in size of the patient, size and experience of the surgeon, and the subtlety of injury, consistent and reproducible reports of joint play between surgeons is not possible. The need that must be met is to provide a controlled application of torque during joint examination, with the magnitude, direction, and rate of torque application being controlled. Many reports have documented that, whether performed by hand or with manual arthrometers, the manual application of torque varies between clinicians, thus creating inconsistencies in the examination of joint play.

Accordingly, there is a need for an accurate, objective, reliable and reproducible measure of the impact of damage to the ACL as well as other ligaments and structures in the knee that can be used in the clinical setting on patients. For example, since an injury to the ACL produces both an increase in anterior translation (z-axis translation) and rotation (y-axis rotation), an objective measure of these changes would both aid in the diagnosis of the injury as well as verify its restoration after ligament reconstruction surgery. Additionally, measurement of displacement and compliance around different degrees of freedom in the knee would help objectively describe the individual and complex changes to 'joint play' that occur with an injury to the knee. A need exists for systems and methods that can provide accurate, reproducible and objective data on the changes in 'joint play' or motion that occurs with an injured knee compared to their normal knee and to the population as a whole such that the clinician can achieve patient satisfaction with focused, biomechanical and proven surgical interventions individualized for that injury and for that knee across the entire population of damaged knees.

Needs also exist for systems and methods, and devices which accommodate variances of patient body structure; it may well be understood that each human body is different and may require particular attention when being treated and/or analyzed; this may be particularly evident in the case of abnormalities of bone, tendon, joint, etc., due to injury or the like.

SUMMARY

Generally described, the present invention to provide apparatuses and methods for evaluating the performance of joints and their associated elements.

In accordance with the purposes of the various embodiments of the present invention as described herein, a method for evaluating relative bone movement characteristics of a patient, the patient having at least three interconnected bones, a first bone connected to a second, "free positioned" bone, and a third bone connected to the second bone, is provided. The method comprising the steps of: A) fixing the first bone relative to a frame; B) attaching a force application system to the third bone; C) moving the third bone with the force application system such that the second, "free positioned" bone moves relative to the frame; and D) measuring movement of the second, "free positioned" bone relative to the base via external measuring.

In accordance with an additional aspect of the present invention as described herein, an apparatus for evaluating leg movement characteristics of a patient, the patient having a torso, and also having a first leg extending from the torso, the leg including a femur, patella, tibia, and a foot, is provided. The apparatus comprises: A) a base assembly configured to at least partially support the torso; and B) a leg support assembly independently pivotably mounted about a pivot axis relative to the base assembly, the leg support assembly configured to at least partially support a portion of the leg, the support being independent of the support of the torso. The leg support assembly comprises: 1) a first leg support member itself comprising a foot rotation assembly configured to at least partially retain and support an associated foot of the patient and to rotate it about an axis of rotation relative to the base assembly; and 2) a second leg support member configured for supporting a portion of the leg at a location proximal relative to the first leg support member during the rotation of the foot, the foot rotation assembly configured to rotate the associated foot such that an associated leg movement is provided and can be measured.

In accordance with the purposes of the various embodiments of the present invention as described herein, an apparatus for evaluating leg movement characteristics of a patient, the patient having a torso, and also having a first and a second leg extending from the torso, each leg including a femur, patella, tibia, and a foot, is provided. The apparatus comprises: A) a base assembly configured to at least partially support the torso; and B) first and second leg support assemblies independently pivotably mounted about a pivot axis relative to the base assembly, each leg support assembly configured to at least partially support a portion of a respective one of the first and second legs, the support being independent of the support of the torso. Each of the leg support assemblies comprises: 1) a first leg support member itself comprising a foot rotation assembly configured to at least partially retain and support an associated foot of the patient and to rotate it about an axis of rotation relative to the base assembly; and 2) a second leg support member configured for supporting a portion of the leg at a location proximal relative to the first leg support member during the rotation of the foot, each the foot rotation assembly configured to rotate the associated foot such that an associated leg movement is provided and can be measured.

In accordance with an additional aspect of the present invention as described herein, an apparatus for evaluating leg movement characteristics of a patient, the patient having a torso, and also having a first and a second leg extending from the torso, each leg including a femur, patella, tibia, and a foot, is provided. The apparatus comprises: A) a base assembly configured to at least partially support the torso; and B) first and second leg support assemblies independently pivotably mounted about a pivot axis relative to the base assembly, each leg support assembly configured to at least partially support a portion of a respective one of the first and second legs, the support being independent of the support of the torso. Each of the leg support members further comprises: 1) a first leg support member itself including a foot rotation assembly configured to at least partially retain and support an associated foot of the patient and to rotate it about an axis of rotation relative to the base assembly; 2) a second leg support member configured for supporting a portion of the associated leg at a location proximal relative to the first leg support member during the rotation of the foot; and 3) a tibia positioning assembly configured to contact the lower leg portion of the associated leg at a location generally intermediate that of the first and second leg support members. Each of the foot rotation assemblies are further configured to rotate the associated foot such that associated leg movement is provided and can be measured while the tibia retention assembly at least partially laterally retains tibia movement.

In accordance with an additional aspect of the present invention as described herein, an apparatus for evaluating leg movement characteristics of a patient, the patient having a torso, and also having a first and a second leg extending from the torso, each leg including a femur, patella, tibia, and a foot, is provided. The apparatus comprises: A) a base assembly configured to at least partially support the torso; and B) first and second leg support assemblies independently pivotably mounted about a pivot axis relative to the base assembly, each leg support assembly configured to at least partially support a portion of a respective one of the first and second legs, the support being independent of the support of the torso. Each of the leg support members itself comprises: 1) a first leg support member itself including a foot rotation assembly configured to at least partially retain and support an associated foot of the patient and to rotate it about an axis of rotation relative to the base assembly; 2) a second leg support member configured for supporting a portion of the associated leg at a location proximal relative to the first leg support member during the rotation of the foot; and 3) a tibia positioning assembly configured to contact the lower leg portion of the associated leg at a location generally intermediate that of the first and second leg support members, the tibia positioning assembly mounted for linear adjustment relative to the pivoting leg support frame assembly, the tibia positioning assembly providing pivoting support of the foot rotation assembly to provide the axis of rotation relative to the base assembly. Each the foot rotation assembly is further configured to rotate the associated foot such that the associated leg movement is provided and can be measured while the tibia retention assembly at least partially laterally retains tibia movement.

In accordance with an additional aspect of the present invention, a method for evaluating leg movement characteristics of a patient, the patient having a torso, and also having a first and a second leg extending from the torso, each leg including a femur, patella, tibia, and a foot, is provided. The method comprising the steps of: A) providing an apparatus comprising: 1) a base assembly configured to at least partially support the torso; and 2) first and second leg support assemblies independently pivotably mounted about a pivot axis relative to the base assembly, each leg support assembly configured to at least partially support a portion of a respective one of the first and second legs, the support being independent of the support of the torso, each of the leg support assemblies including: a) a first leg support member itself including a foot rotation assembly configured to at least partially retain and support an associated foot of the patient and to rotate it about an axis of rotation relative to the base assembly; and b) a second leg support member configured for supporting a portion of the leg at a location proximal relative to the first leg support member during the rotation of the foot; and B) placing a patient in the device, rotating the associated foot such that the associated leg movement is provided, and measuring the movement.

In accordance with an additional aspect of the present invention, a method for evaluating leg movement characteristics of a patient, the patient having a torso, and also having a first and a second leg extending from the torso, each leg including a femur, patella, tibia, and a foot, the method comprising the steps of: A) providing an apparatus comprising: 1) a base assembly configured to at least partially support the torso; and 2) first and second leg support assemblies independently pivotably mounted about a pivot axis relative to the base assembly, each leg support assembly configured to at least partially support a portion of a respective one of the first and second legs, the support being independent of the support of the torso, each of the leg support members including: a) a first leg support member itself including a foot rotation assembly configured to at least partially retain and support an associated foot of the patient and to rotate it about an axis of rotation relative to the base assembly; b) a second leg support member configured for supporting a portion of the associated leg at a location proximal relative to the first leg support member during the rotation of the foot; and c) a tibia positioning assembly configured to contact the lower leg portion of the associated leg at a location generally intermediate that of the first and second leg support members; and B) placing a patient in the device, rotating the associated foot such that the associated leg movement is provided, and measuring the movement.

In accordance with an additional aspect of the present invention, a method for evaluating leg movement characteristics of a patient, the patient having a torso, and also having a first and a second leg extending from the torso, each leg including a femur, patella, tibia, and a foot, the method comprising the steps of: A) providing an apparatus that has a knee support configuration that allows for alternate uses, including a support mode for varus-valgus testing, and also a stabilizing mode for both anterior-posterior and rotational testing; B) using the knee support apparatus in the support mode for varus-valgus testing; and C) using the knee support apparatus in the stabilizing mode for both anterior-posterior and rotational testing.

All of the various embodiments above can and will be combined with an external measure device to determine accurately the relationship between the femur and the tibia during the application of force presented above. These external measuring devices include Computerized Tomography (CT Scan), Magnetic Resonance Imaging (MRI Scan), electromagnetic tracking systems, optical tracking systems, sound based tracking systems, light emitting diode based tracking systems, fluoroscopy, sterofluoroscopy, steroradiography, piezo-electric measuring systems or photographic measuring systems. It is not obvious that the combination of a precision force application system perturbating the knee rather than holding or trapping the knee and a measuring system leads to the best measure of ligamentous abnormalities or changes in 'joint play'.

It is important to note that that the current concept of perturbating the knee in three directions is different from the prior art concepts relating an MTS (material testing system) or Insitron machine which measures load deformation in a traditional engineering way. In an MTS machine each side of a material or a device is attached to a plate which is attached to the machine. A known load is placed across the material or device at a known rate. The displacement between the two plates is recorded and a load-deformation curves is reported.

In the device and method of the applicant, the tibia is a "floating" or intercalary bone between two other bones, the femur and the 'ankle' bone. Thus, both sides of the knee are not rigidly attached to the machine like an MTS device. The "force application" portion of the device perturbates the tibia by transferring a rotational force through the ankle bone or by pushing tibia in the anterior/posterior or medial/lateral direction. The "measuring system", which is independent but computationally connected to the "force application" portion of the device (aka the "robot") then measures the positional result of this perturbation. This is then placed in a load deformation curve similar to but not the same as in a MTS device. The main difference is that if the tibia were directly held then it would not be allowed to freely move in 6 degrees of freedom whereas with the perturbation technique the full 6 degrees of motion in the tibia is dynamically observed during the anterior/posterior (etc.) application of force seen during a clinical examination.

Other aspects, features, and advantages of the present invention will become apparent upon reading the following detailed description of the preferred embodiment of the invention when taken in conjunction with the drawing and the appended claims.

BRIEF DESCRIPTION OF THE DRAWINGS

Figure 1:
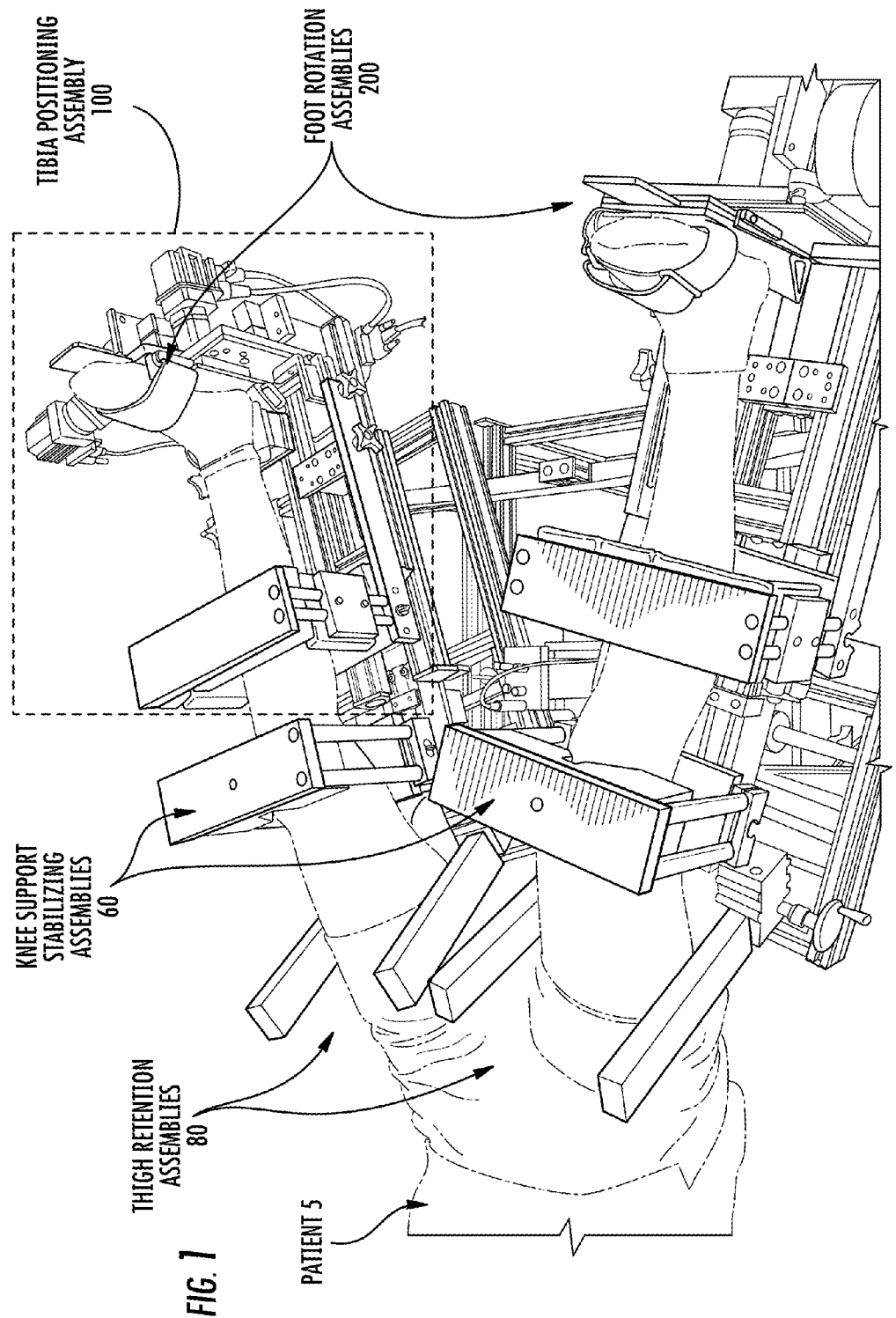

Having thus described the invention in general terms, reference will now be made to the accompanying drawings, which are not necessarily drawn to scale, and wherein:

FIG. 1 is a perspective view of the overall RKT apparatus 10. As may be understood, the apparatus 10 supports the entirety of a foot (shown in outline at the distal end of the leg 5 in FIG. 3) such that certain rotational axes described herein are distal to the entirety of the foot as shown in FIGS. 1 and 3.

Figure 2:
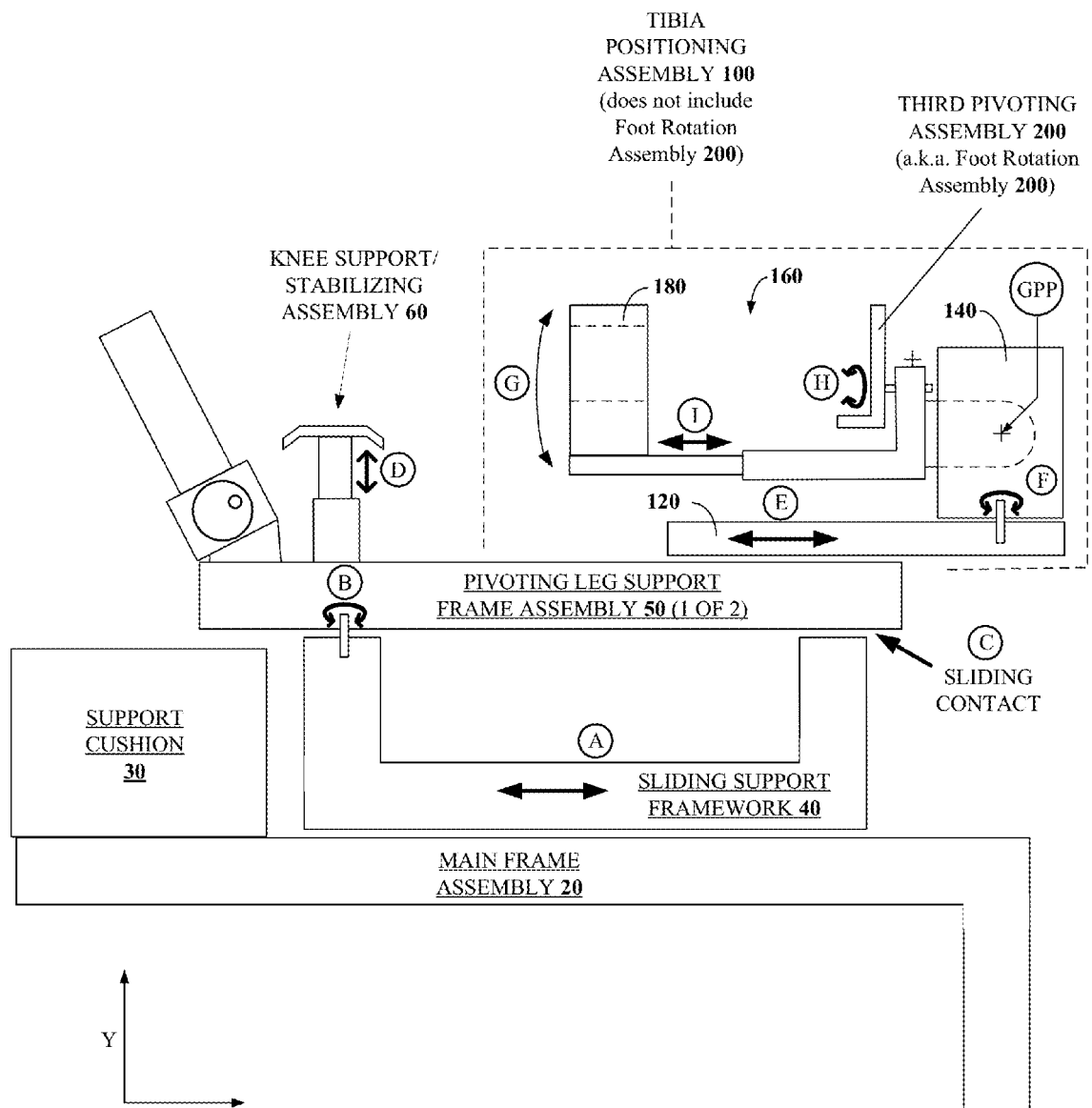

FIG. 2 is an illustrative side elevational view of the general components and operation of the overall RKT apparatus 10.

Figure 3:
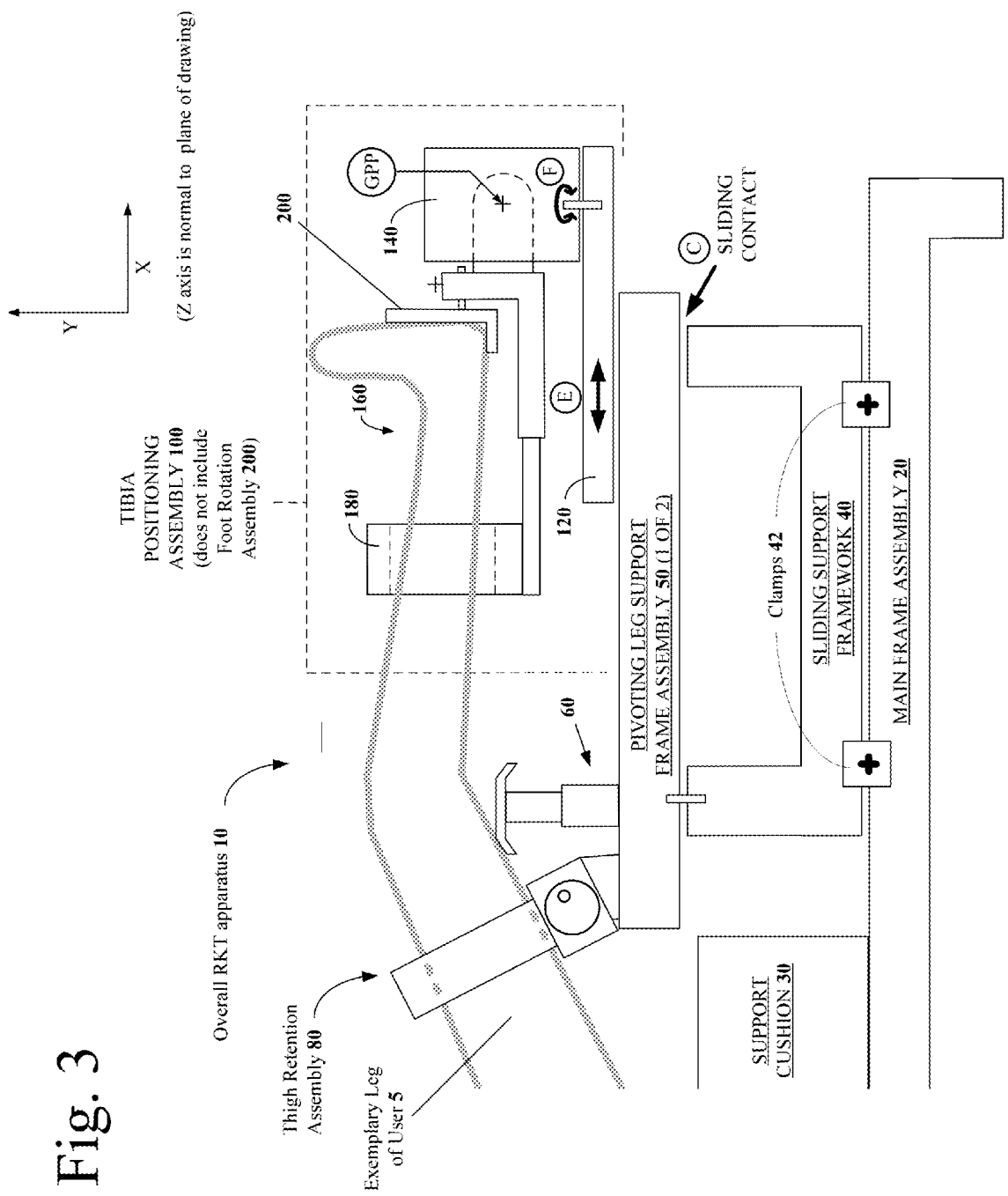

FIG. 3 is a closer view of a portion of that shown in FIG. 2.

FIG. 4 is a closer view of a portion of that shown in FIG. 3.

Figure 5:
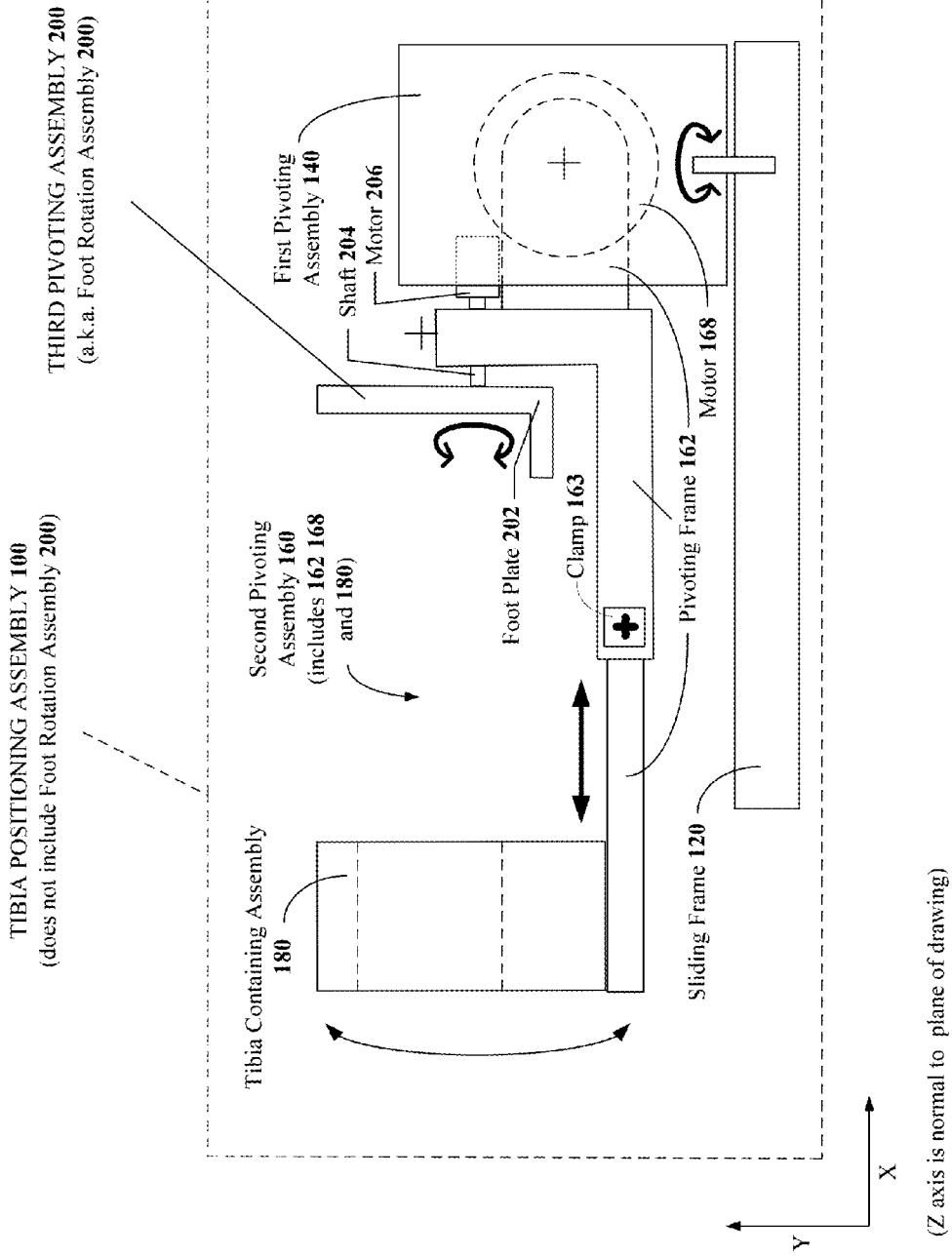

FIG. 5 is a closer view of a portion of that shown in FIG. 4.

Figure 6:
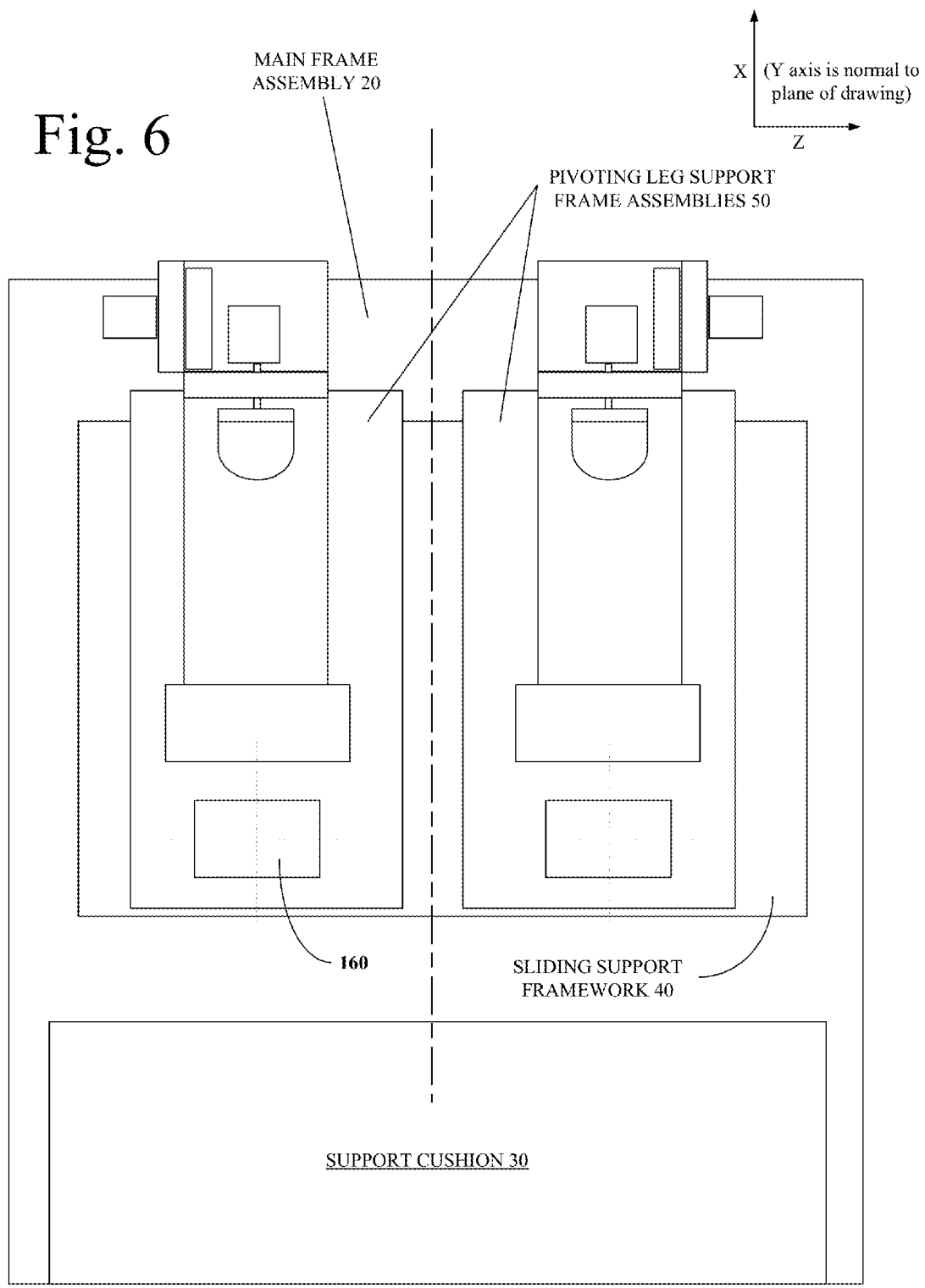

FIG. 6 is a illustrative top elevational view of the general components and operation of the overall RKT apparatus 10. The two pivoting leg support frame assemblies are shown in generally parallel fashion.

Figure 7:
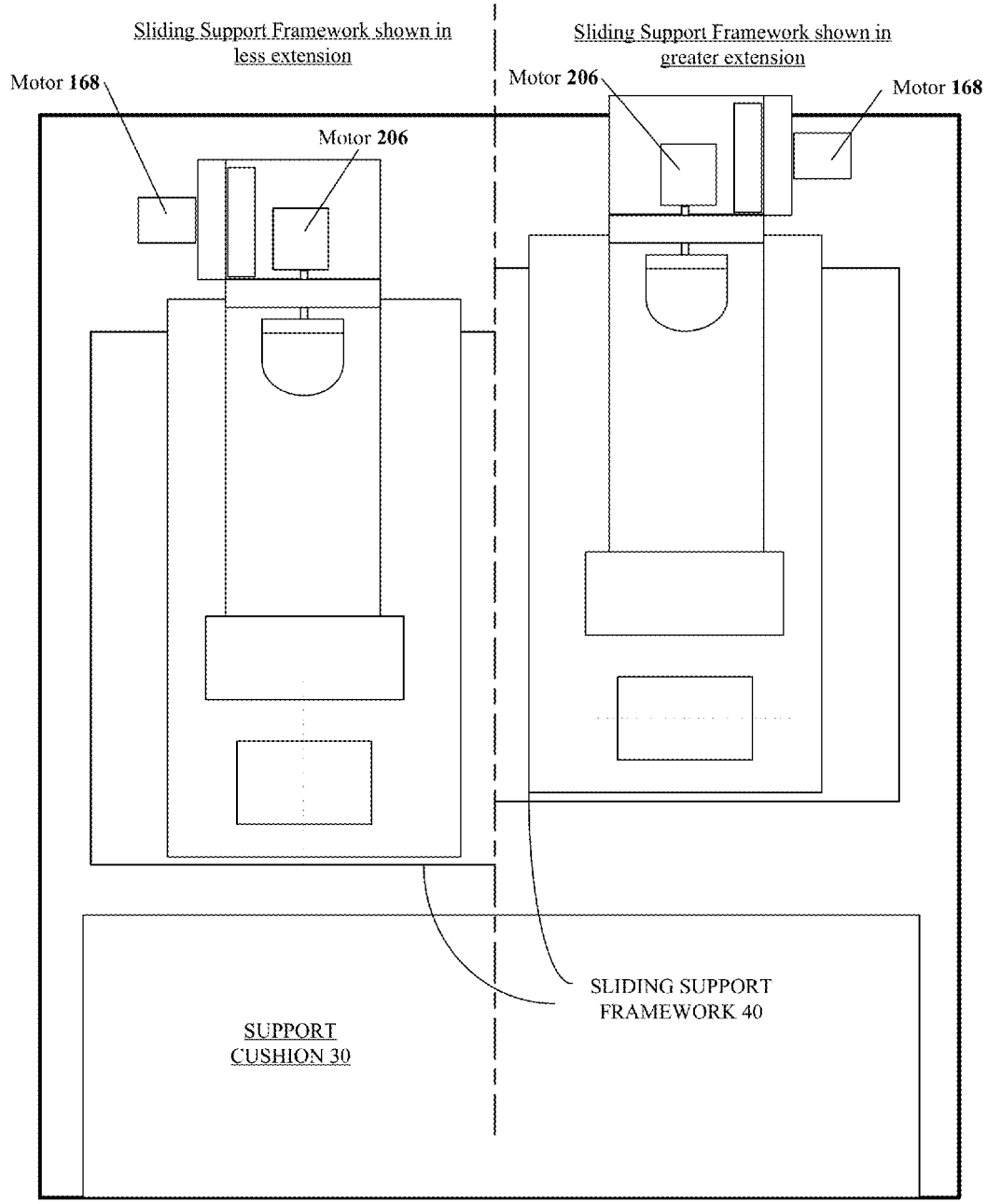

FIG. 7 is a view similar to that shown in FIG. 6, except that the two sliding support frameworks are shown in different extension configurations.

Figure 8:
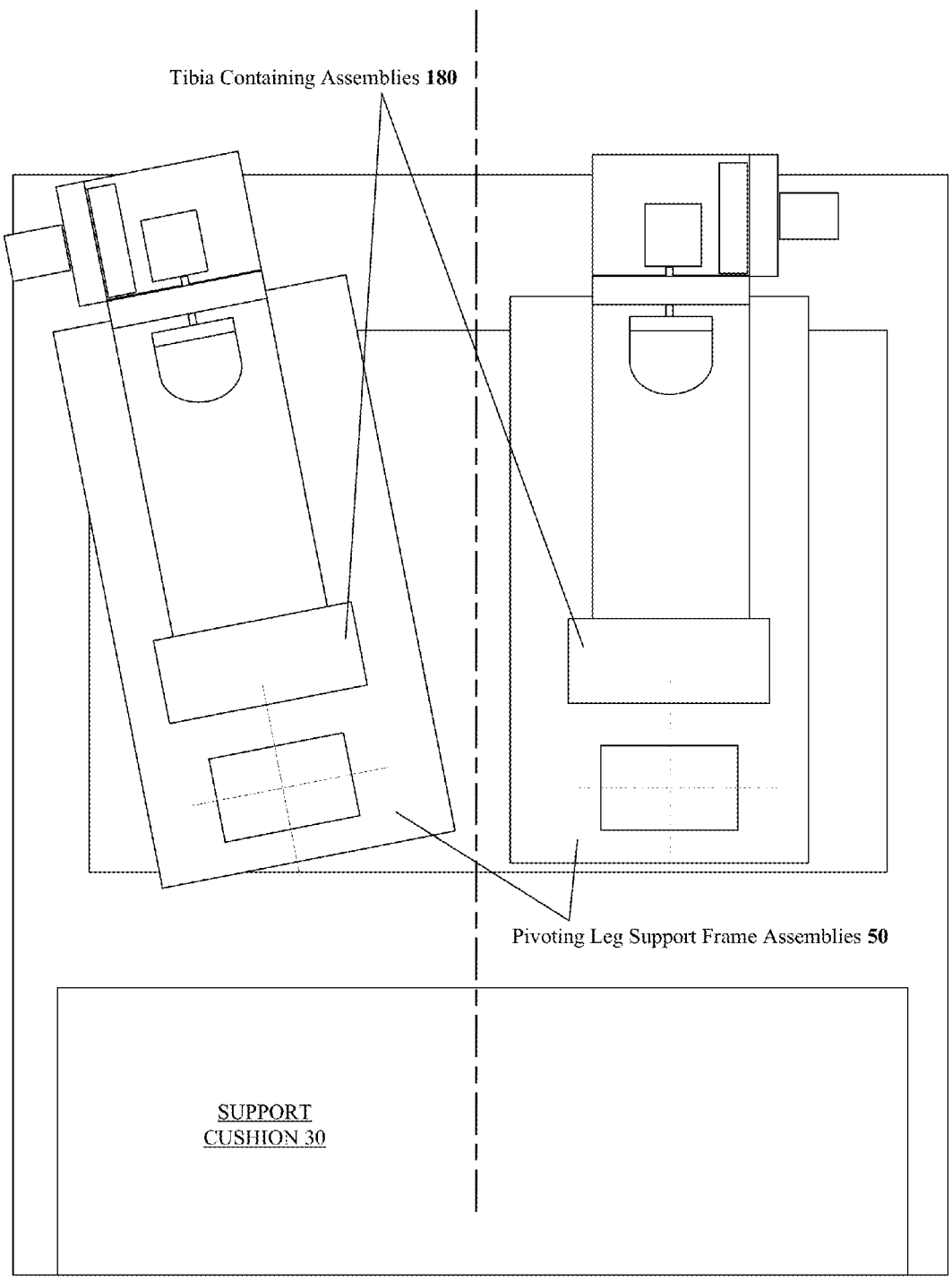

FIG. 8 is a view similar to that shown in FIG. 6, except that the two pivoting leg support frame assemblies 50 are shown in different angular relationships.

Figure 9:
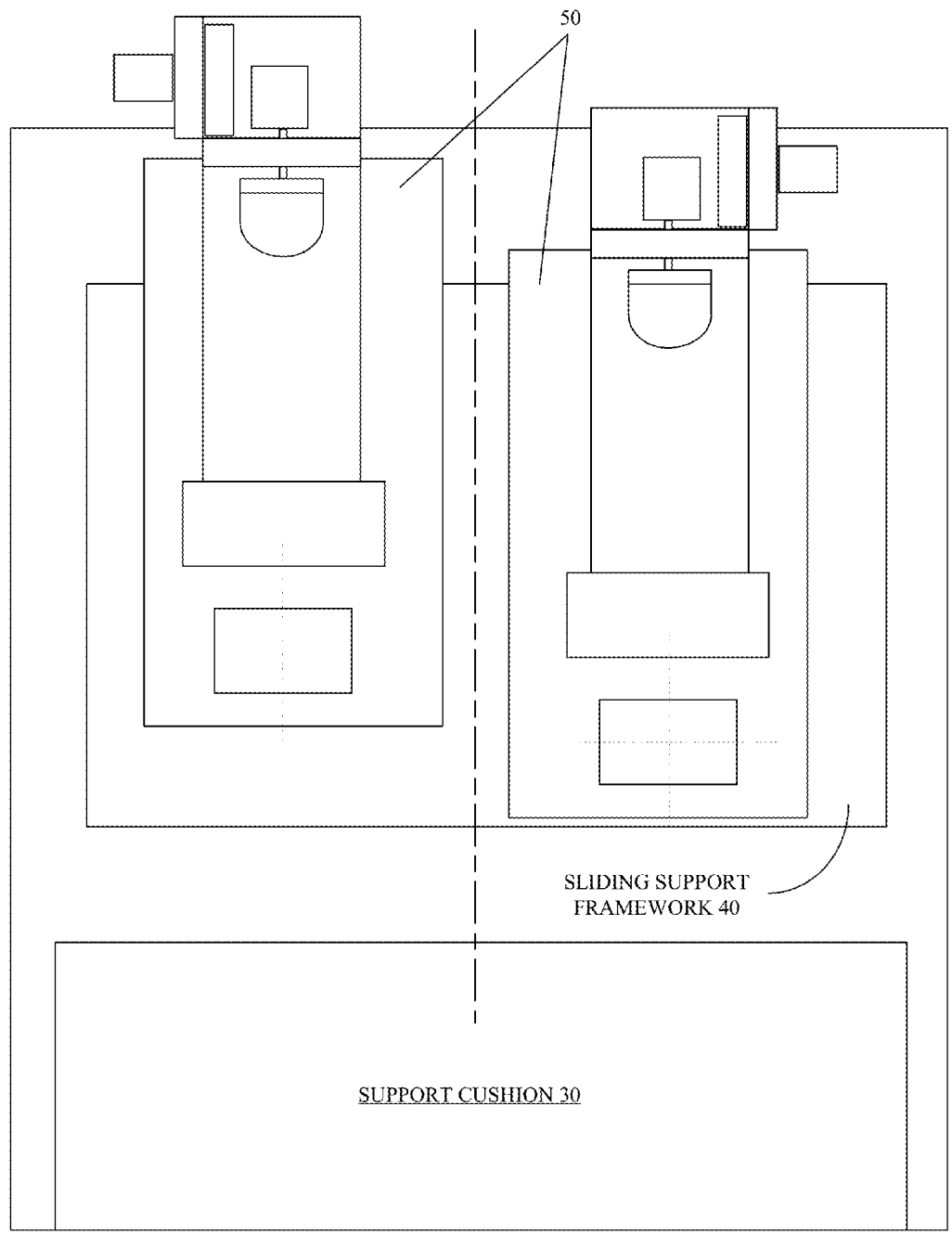

FIG. 9 is a view similar to that shown in FIG. 6, except that the two pivoting leg support frame assemblies 50 are shown in different extension relationships.

Figure 10:
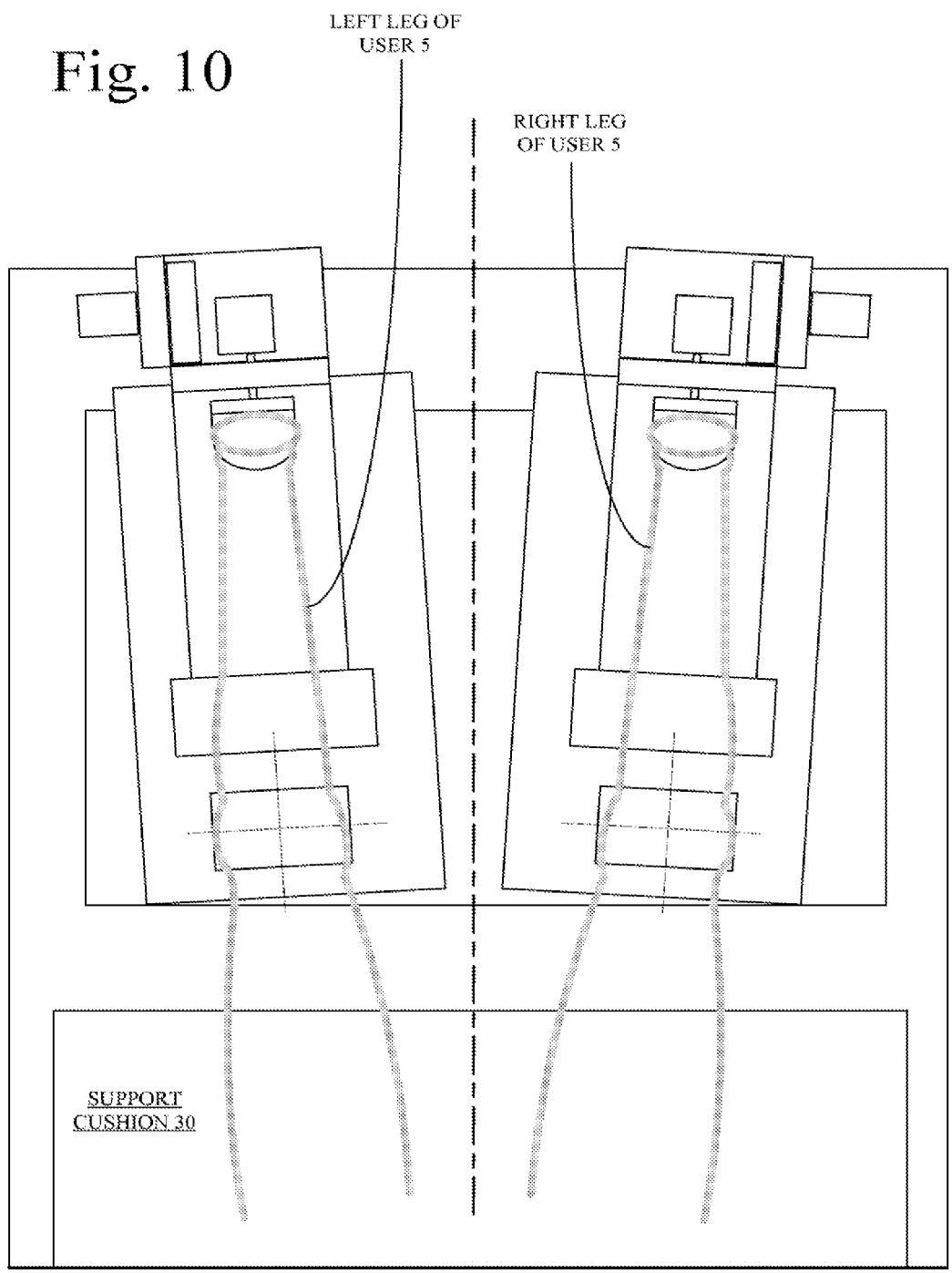

FIG. 10 is a view similar to that shown in FIG. 6, except that the two pivoting leg support frame assemblies 50 are shown in different extension relationships in order to accept the legs of a user 5.

Figure 11:
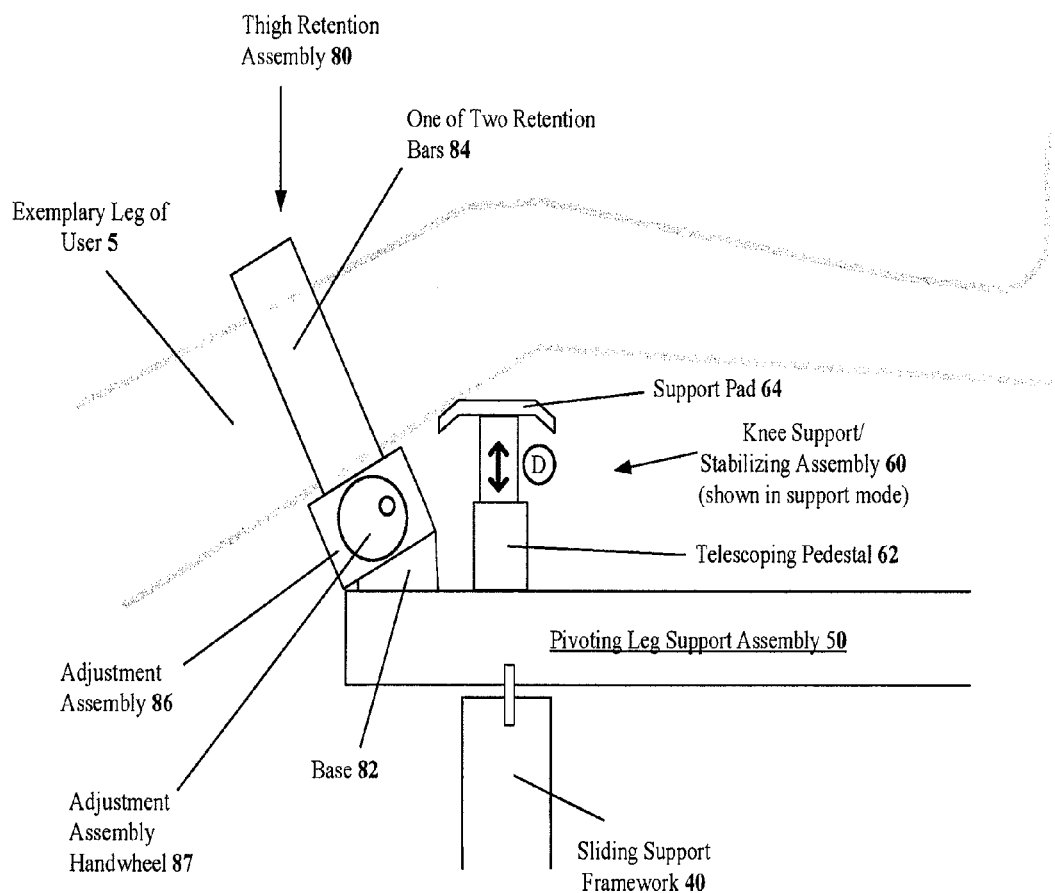

FIG. 11 is a closer view of a portion of that shown in FIG. 3, showing Action D.

FIG. 12 is an illustrative view showing the transverse cross section of a thigh of a user in association with a corresponding thigh retention assembly 80.

FIG. 13 is an illustrative view, showing the transverse cross section of a knee of a user in association with a corresponding knee support/stabilizing assembly 60 (in support mode).

FIG. 14 is an illustrative view, showing the transverse cross section of a knee of a user in association with a corresponding knee support/stabilizing assembly 60 (in stabilizing mode).

FIG. 15 is an illustrative view showing the transverse cross section of a tibia of a user in association with a corresponding tibia retention assembly 60.

FIG. 16 is a pictorial illustrative view of the pivoting interaction between the sliding frame 122 of a tibia positioning assembly 100, a corresponding pivoting frame 142 of a first pivoting assembly 140 (pivots relative to sliding frame 120 via Action F, about a vertical, "Y" axis) a corresponding pivoting frame 162 of a corresponding second pivoting assembly 160, (pivots relative to first pivoting assembly 140 along Action G, along a horizontal axis) and a foot plate 202, which (pivots relative to pivoting frame 162 along Action H).

FIG. 17 shows a subjective measurement module 2000 including a subjective measurement module dial 2001 (operated by the user) and an output display 2002.

FIG. 18 shows a subjective measurement module 2200 including a subjective measurement module slide 2201 (operated by the user) and an output display 2202.

Figure 19:
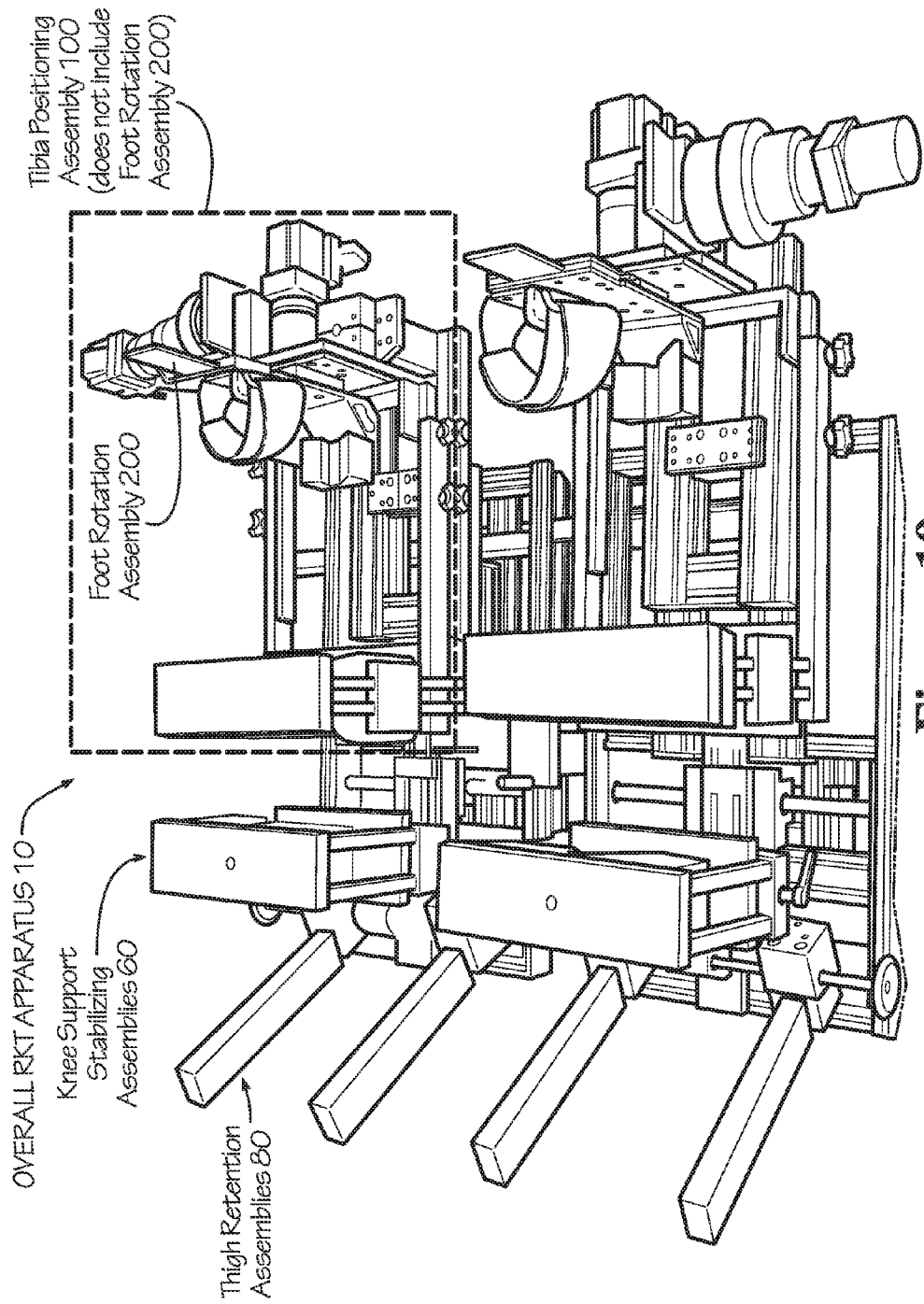

FIG. 19 is another pseudo-overhead view of the overall RKT apparatus 10.

Figure 20:
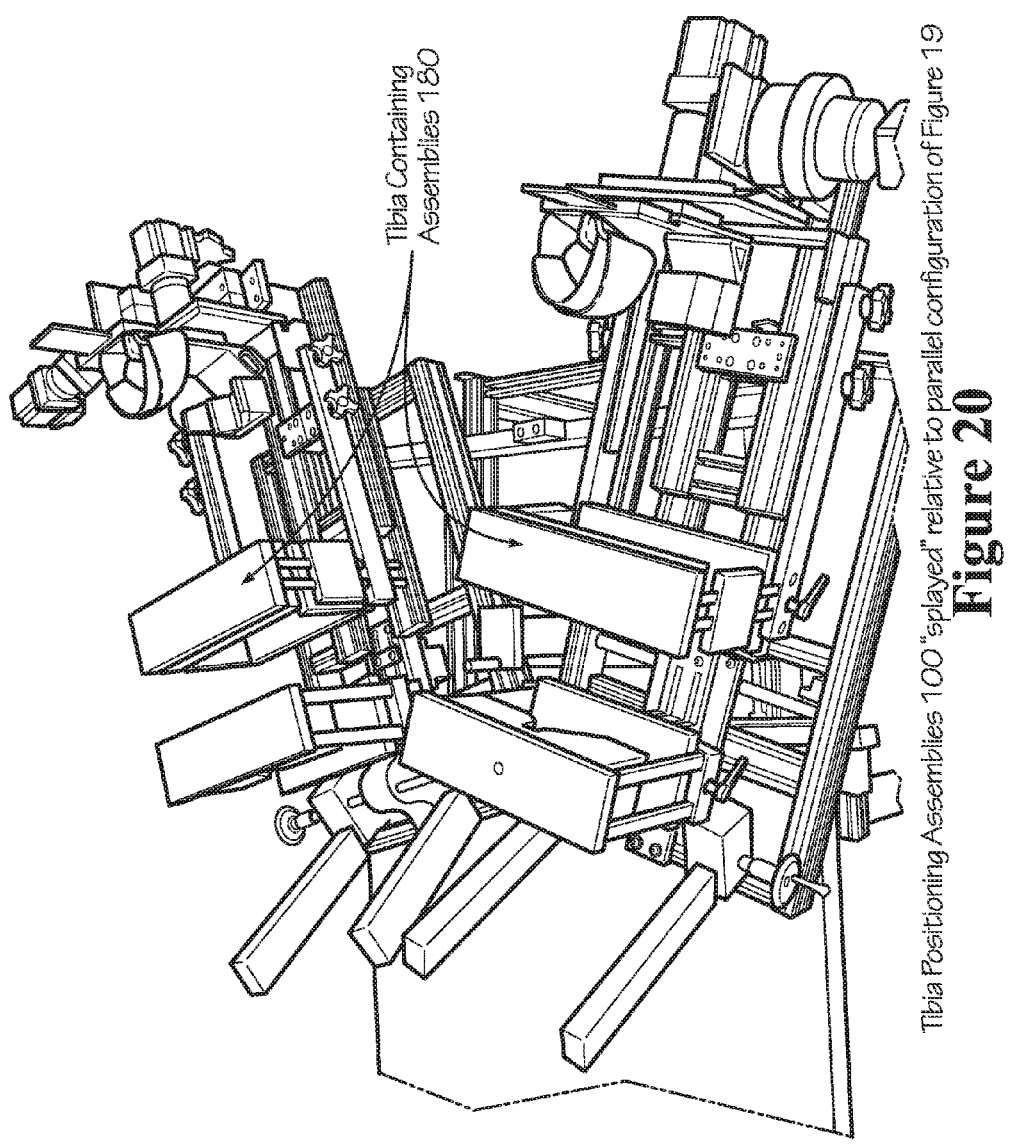

FIG. 20 is a view similar to FIG. 19, with the Tibia Positioning Assemblies 100 and their respective Tibia Containing Assemblies 180 "splayed" relative to the parallel configuration of FIG. 19.

Figure 21:
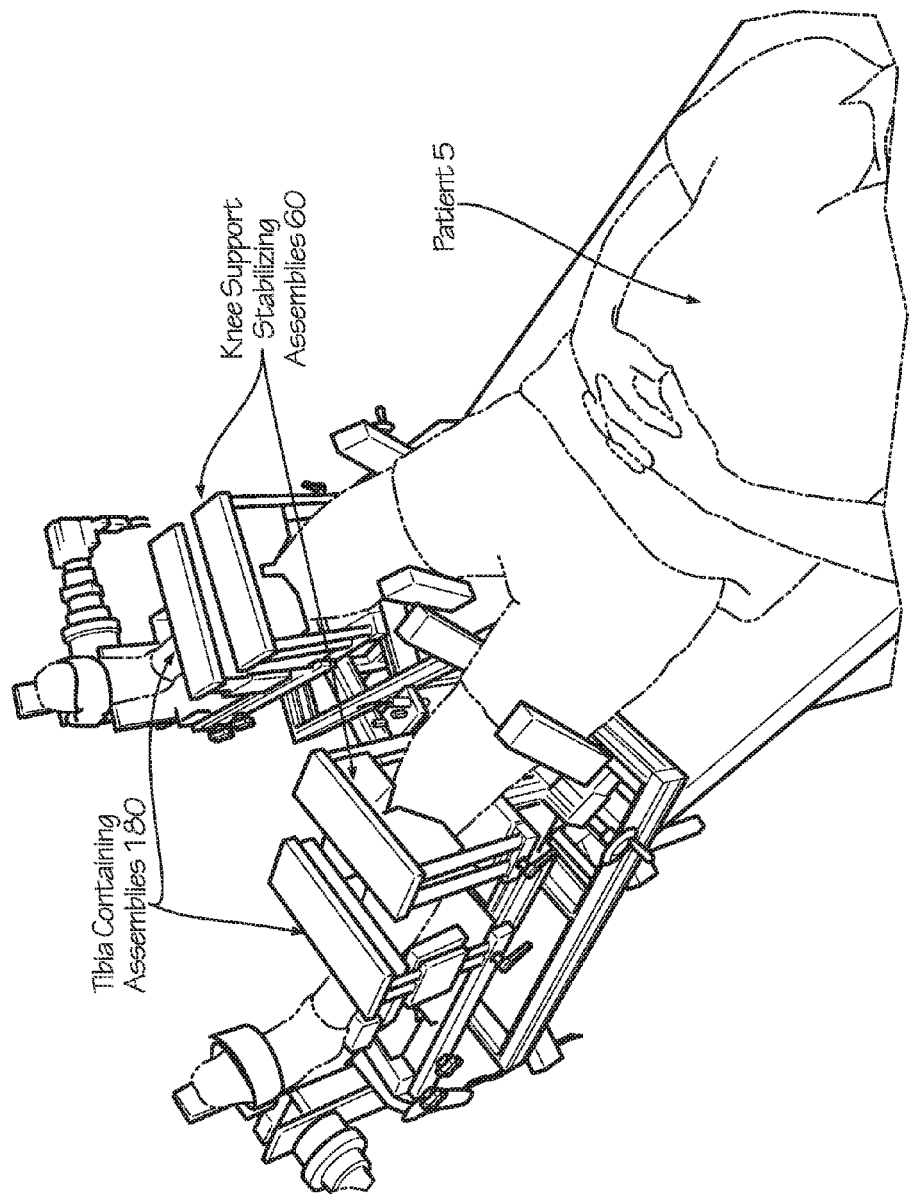

FIG. 21 is similar to FIG. 20 but from different viewpoint and with patient 5 in place.

Figure 22:
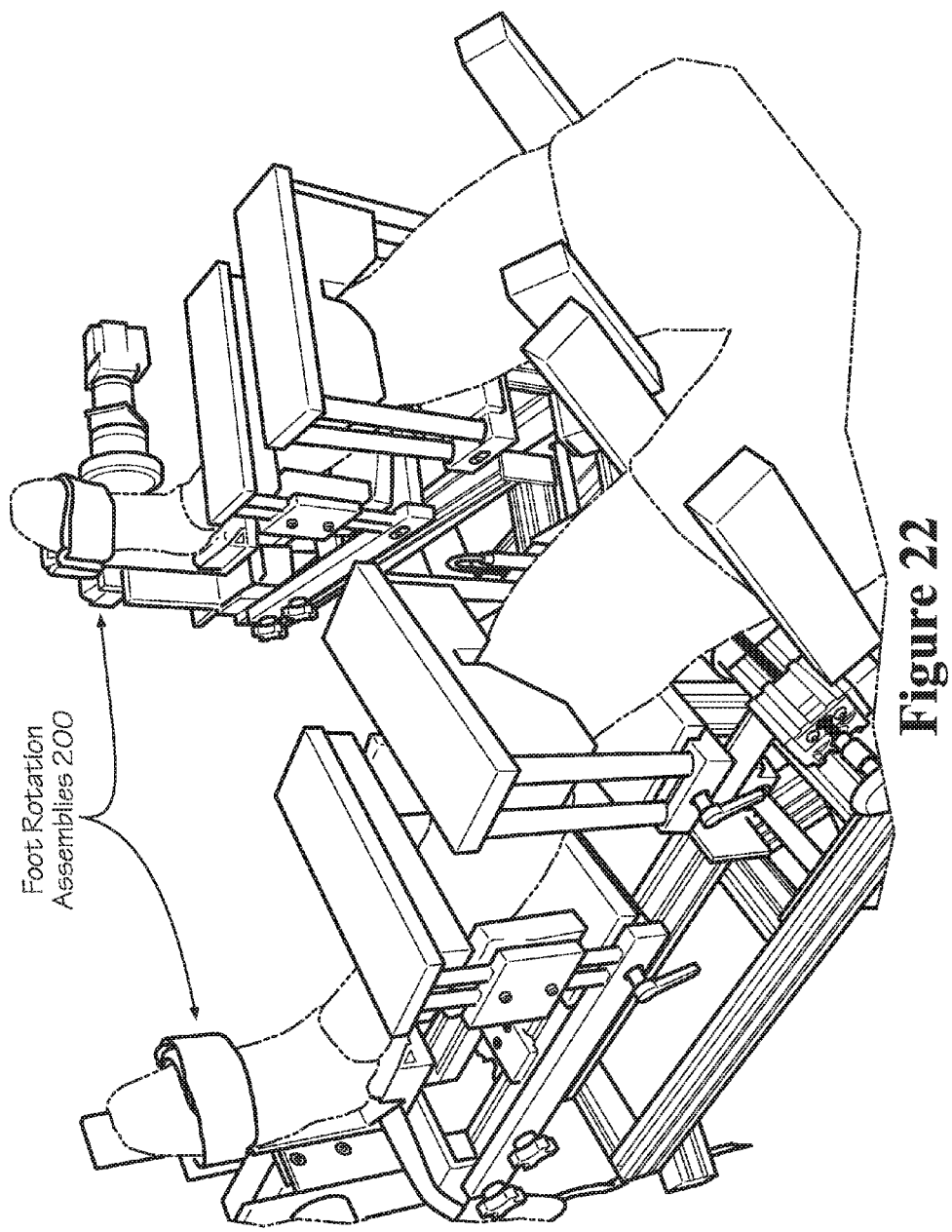

FIG. 22 is similar to FIG. 21 but a closer view.

Figure 23:
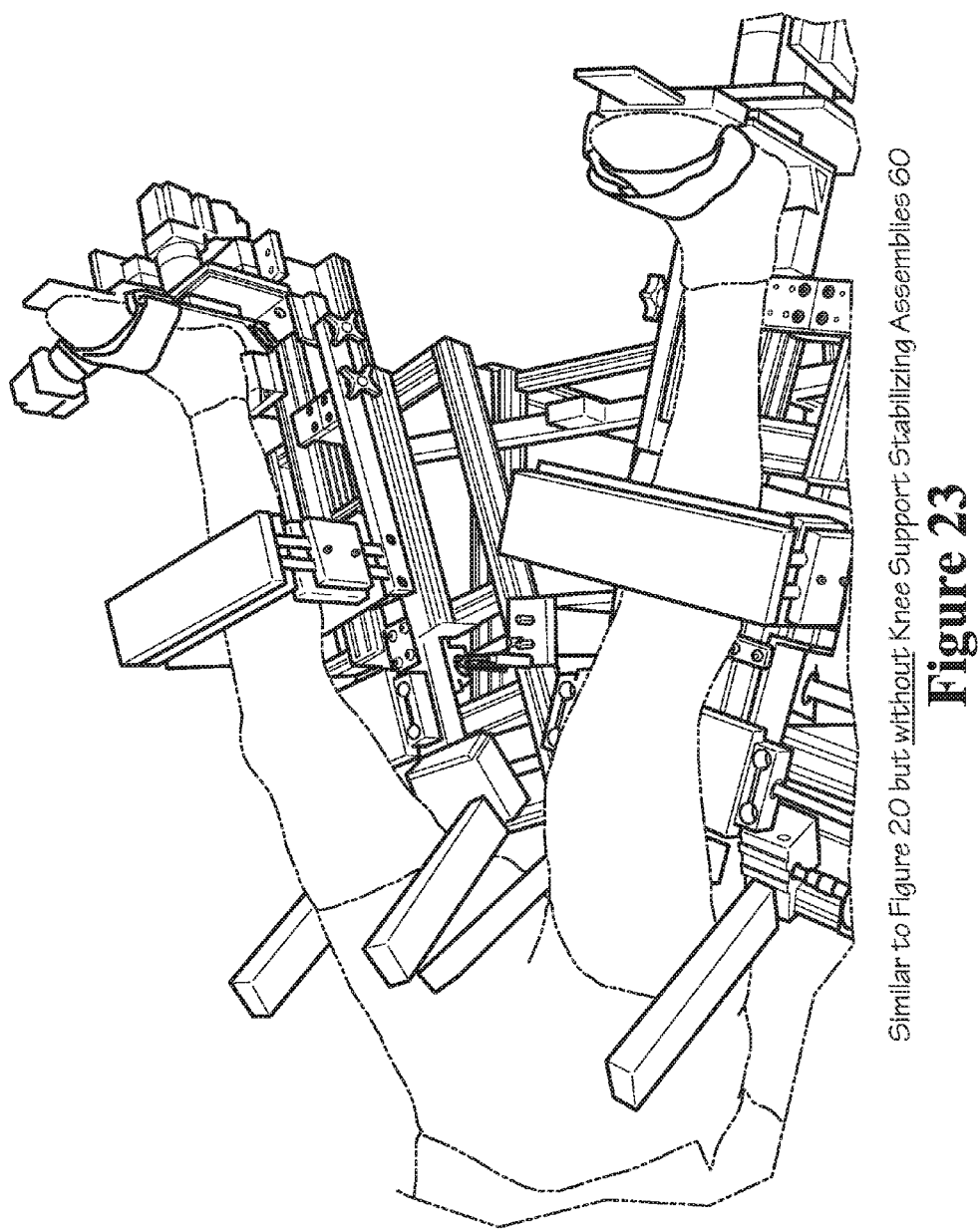

FIG. 23 is similar to FIG. 20 but without knee support stabilizing assemblies 60.

Figure 24:
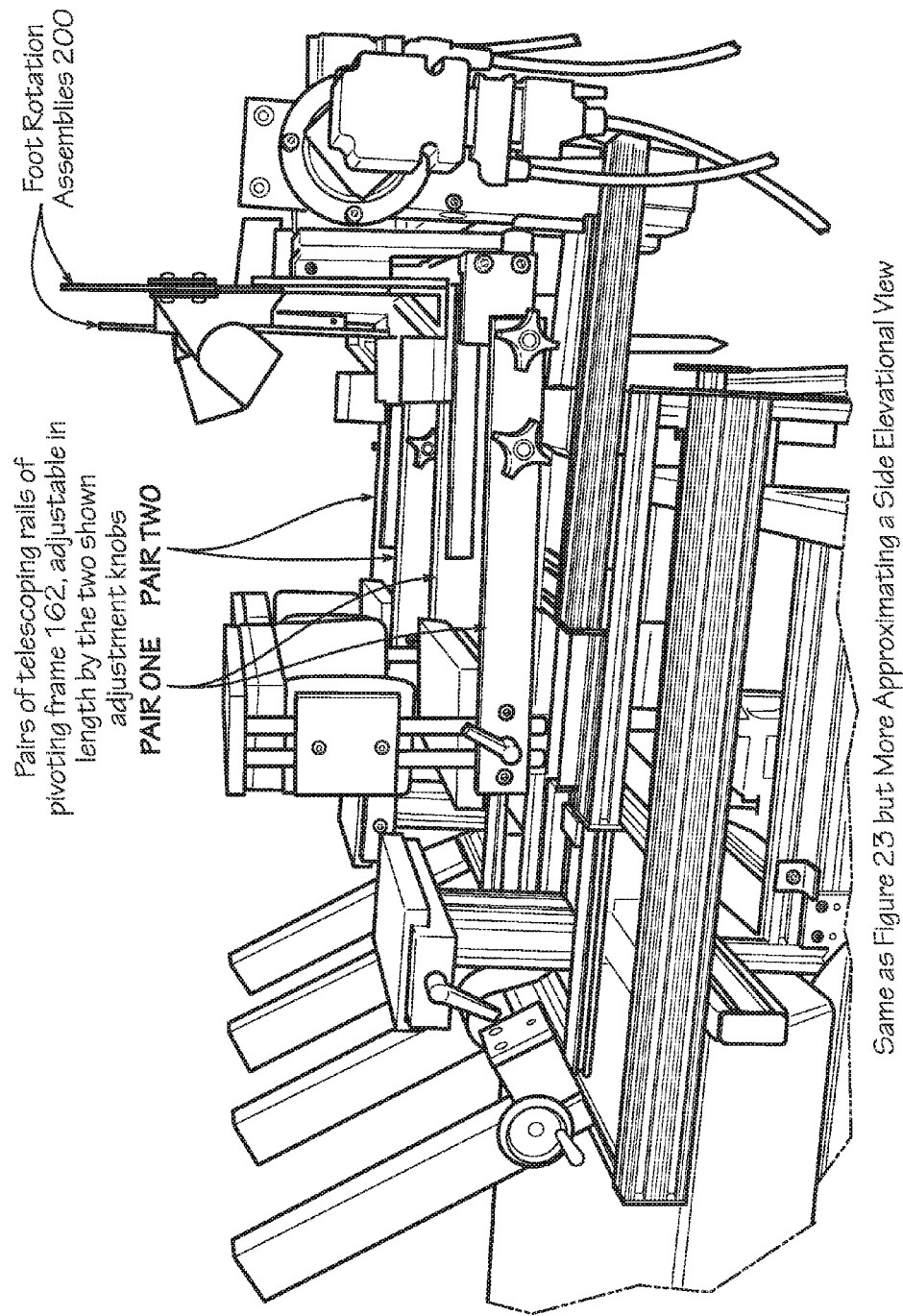

FIG. 24 is similar to FIG. 23 but more approximating a side elevational view.

Figure 25:
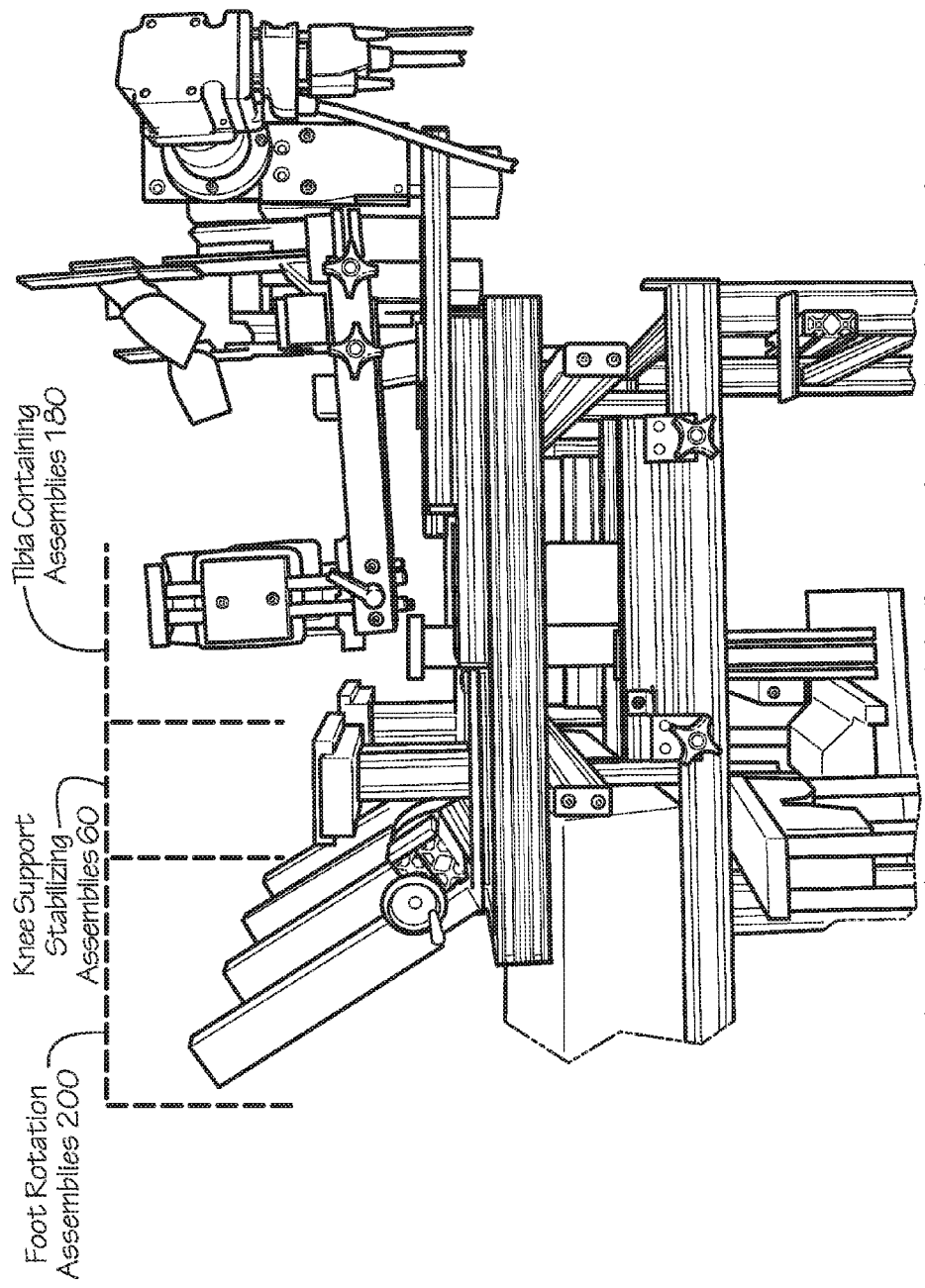

FIG. 25 is even more approximating a side elevational view relative to FIG. 24.

Figure 26:
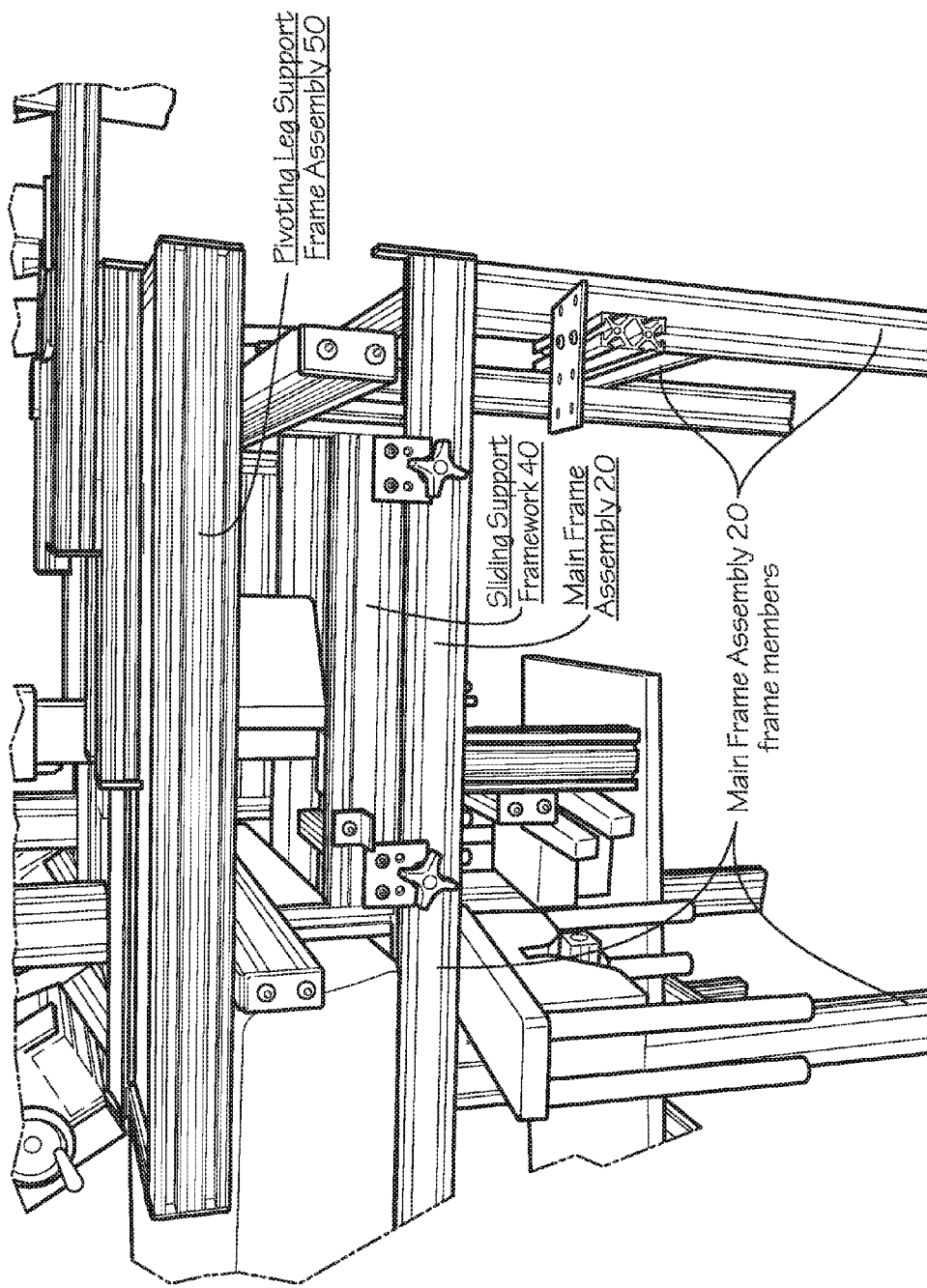

FIG. 26 is a view of the main frame assembly 20 and other lower situation elements.

Figure 27:
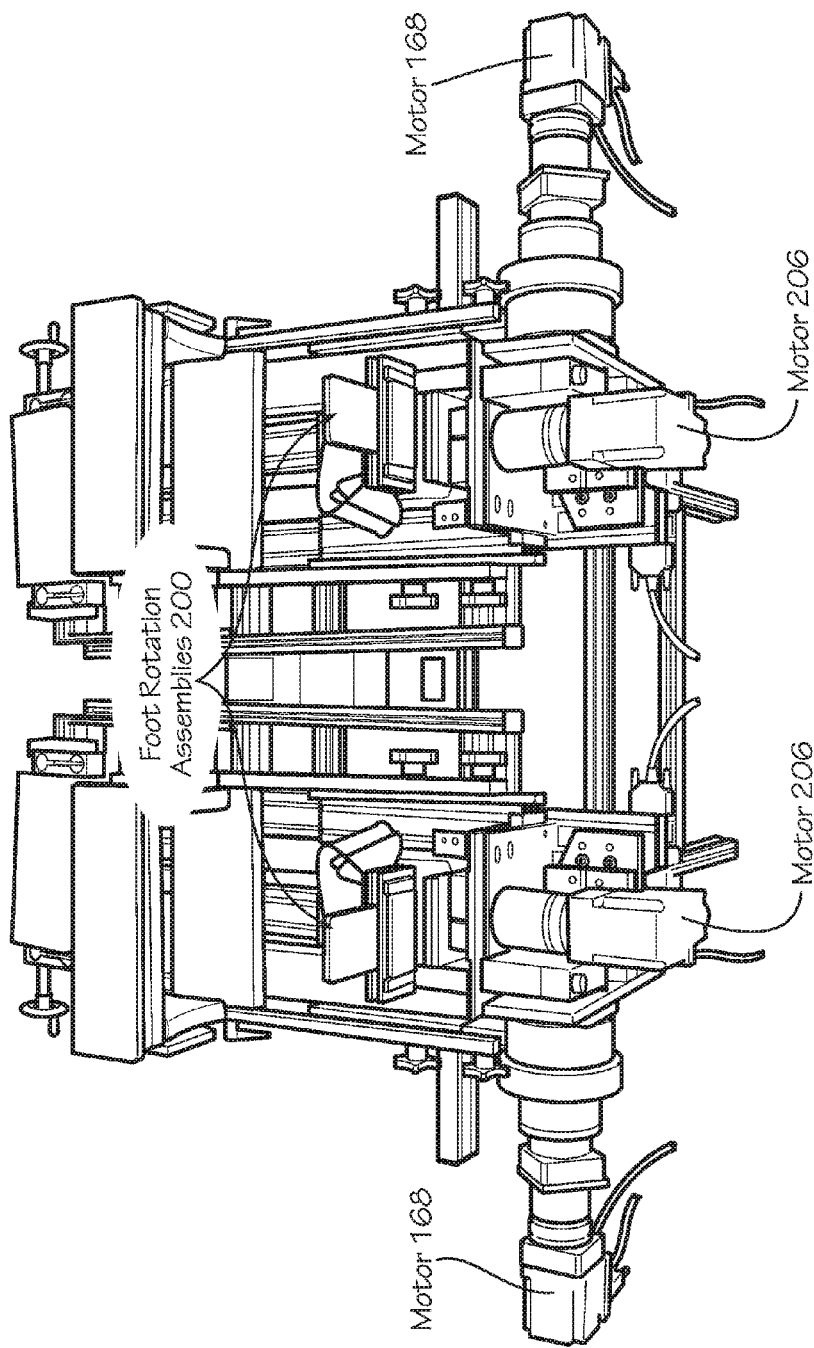

FIG. 27 is a slight overhead view from the foot of the device 10, shown without knee support stabilizing assemblies 60.

Figure 28:
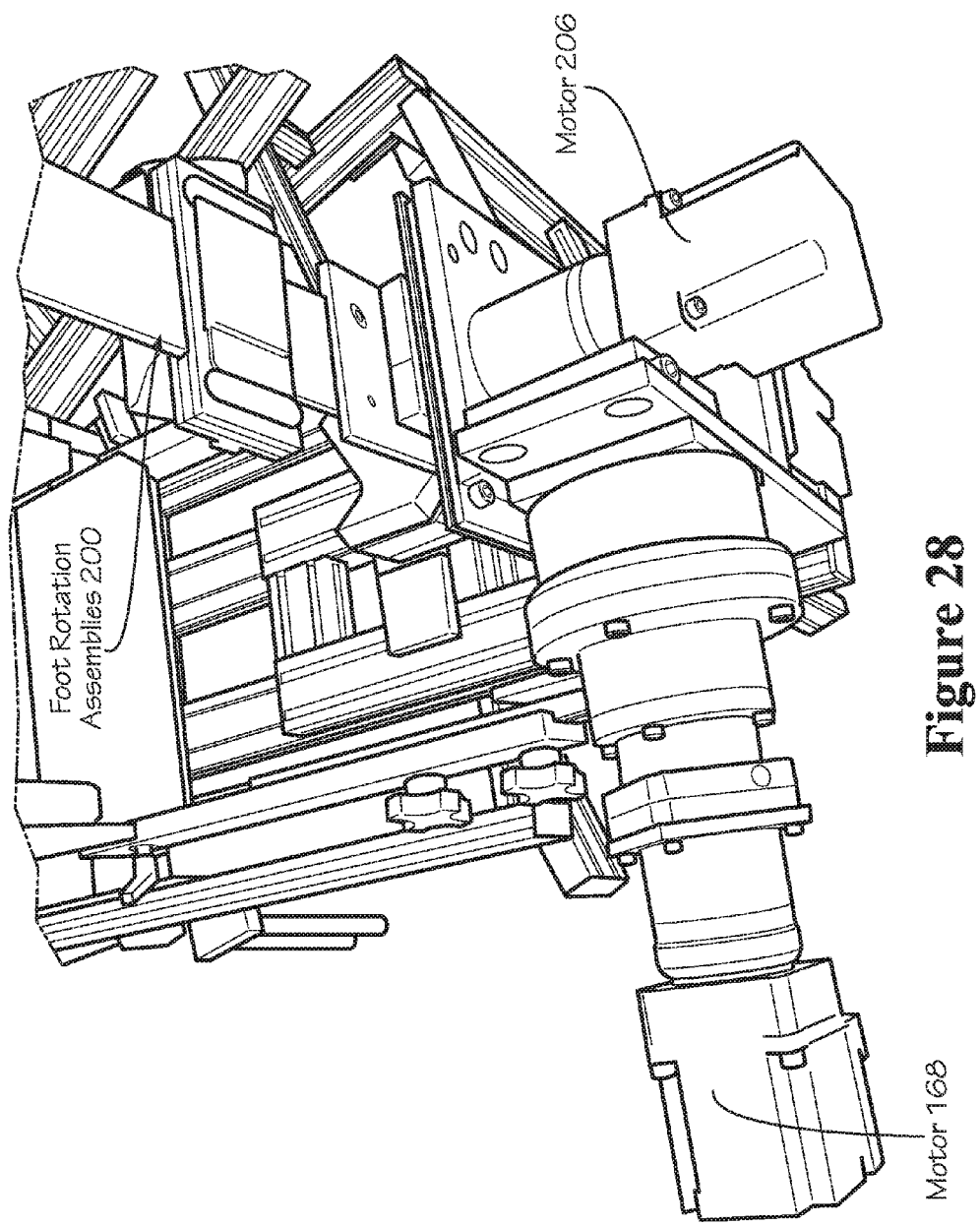

FIG. 28 is a slight overhead view from the foot of the device 10, showing two motors 168 and 206, and the foot rotation assembly 200 (which includes straps for holding the foot).

Figure 29:
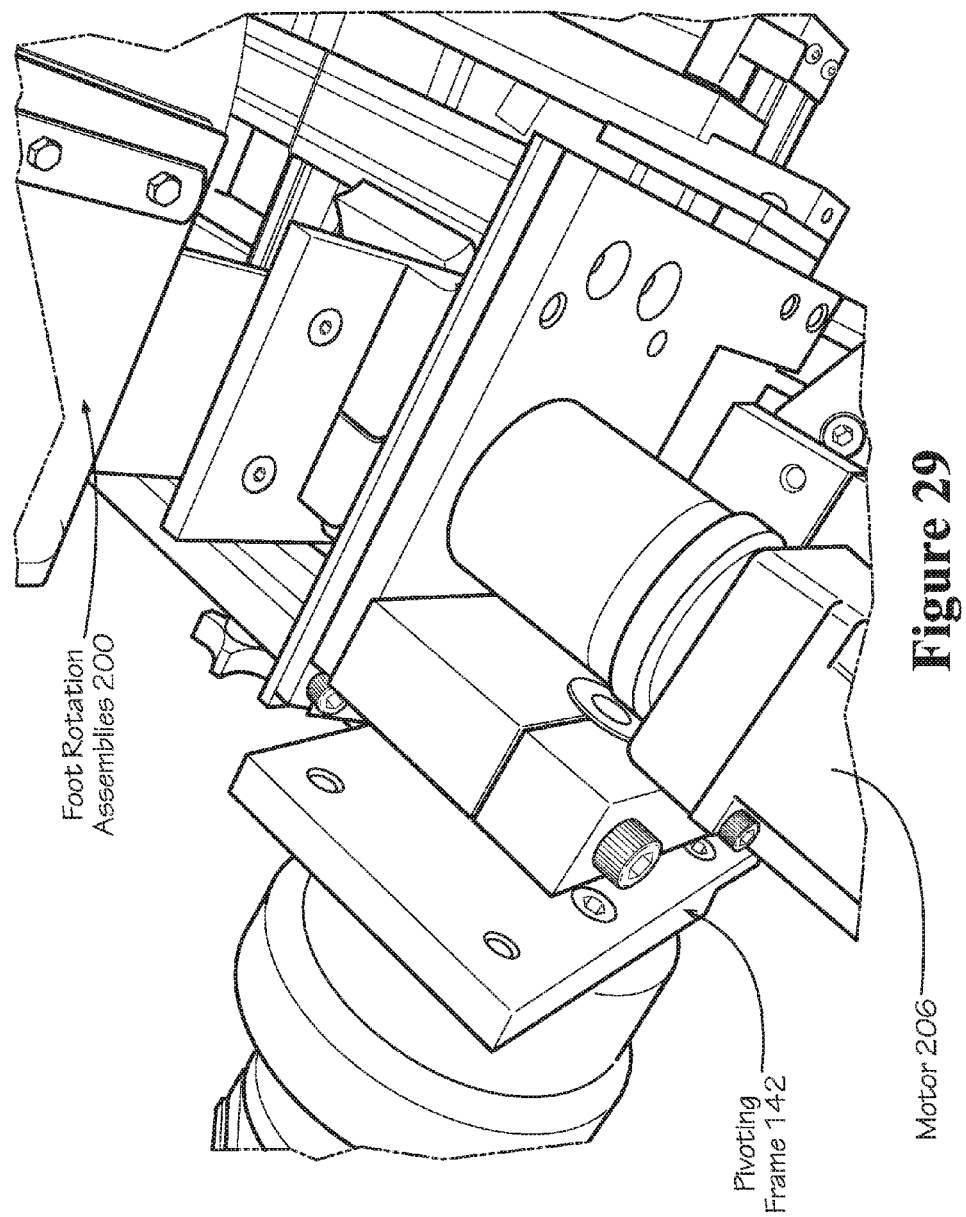

FIG. 29 is a slight overhead view from the foot of the device 10, showing two motors 168 and 206, the foot rotation assembly 200 (which includes straps for holding the foot), and the pivoting frame 142.

Figure 30:
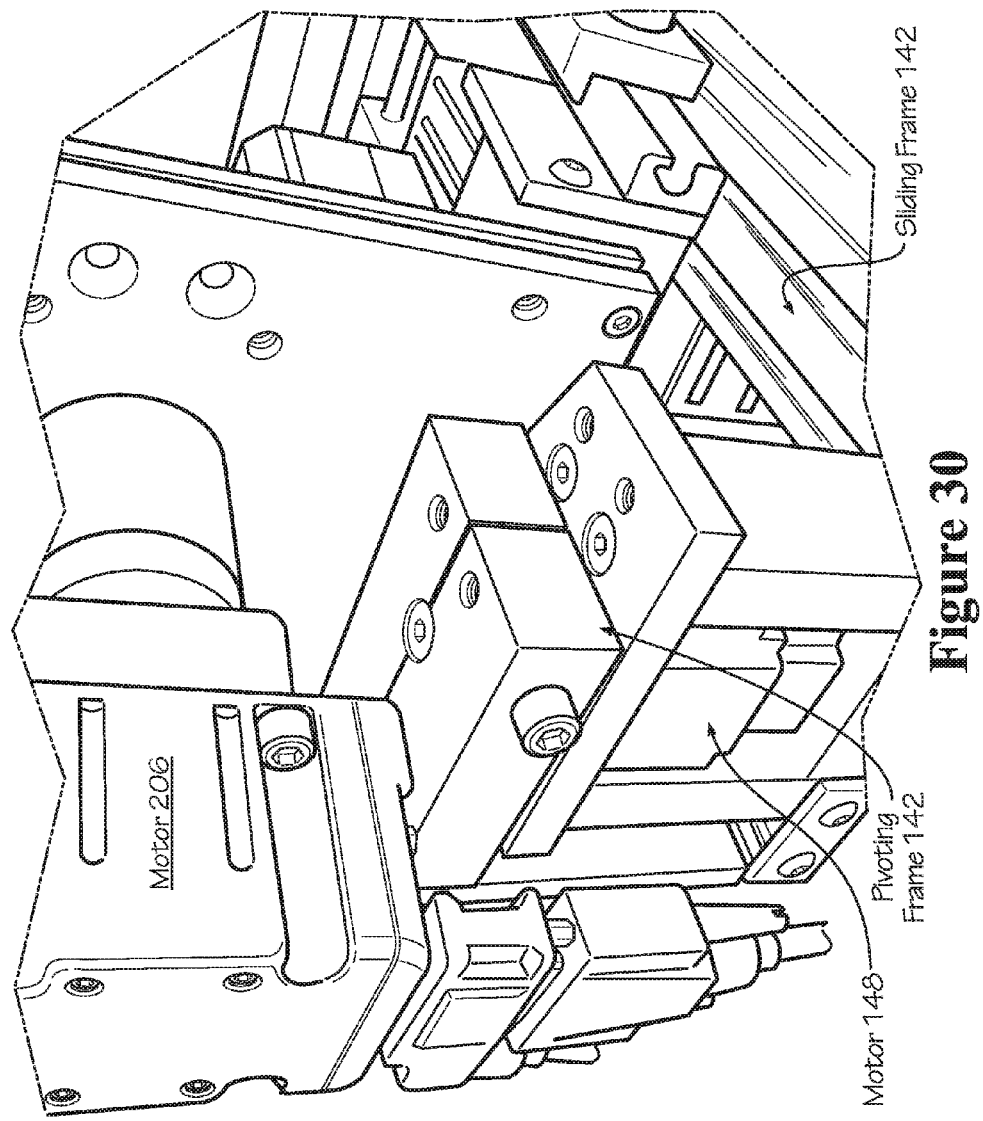

FIG. 30 is a slightly lower view than FIG. 29.

Figure 31:
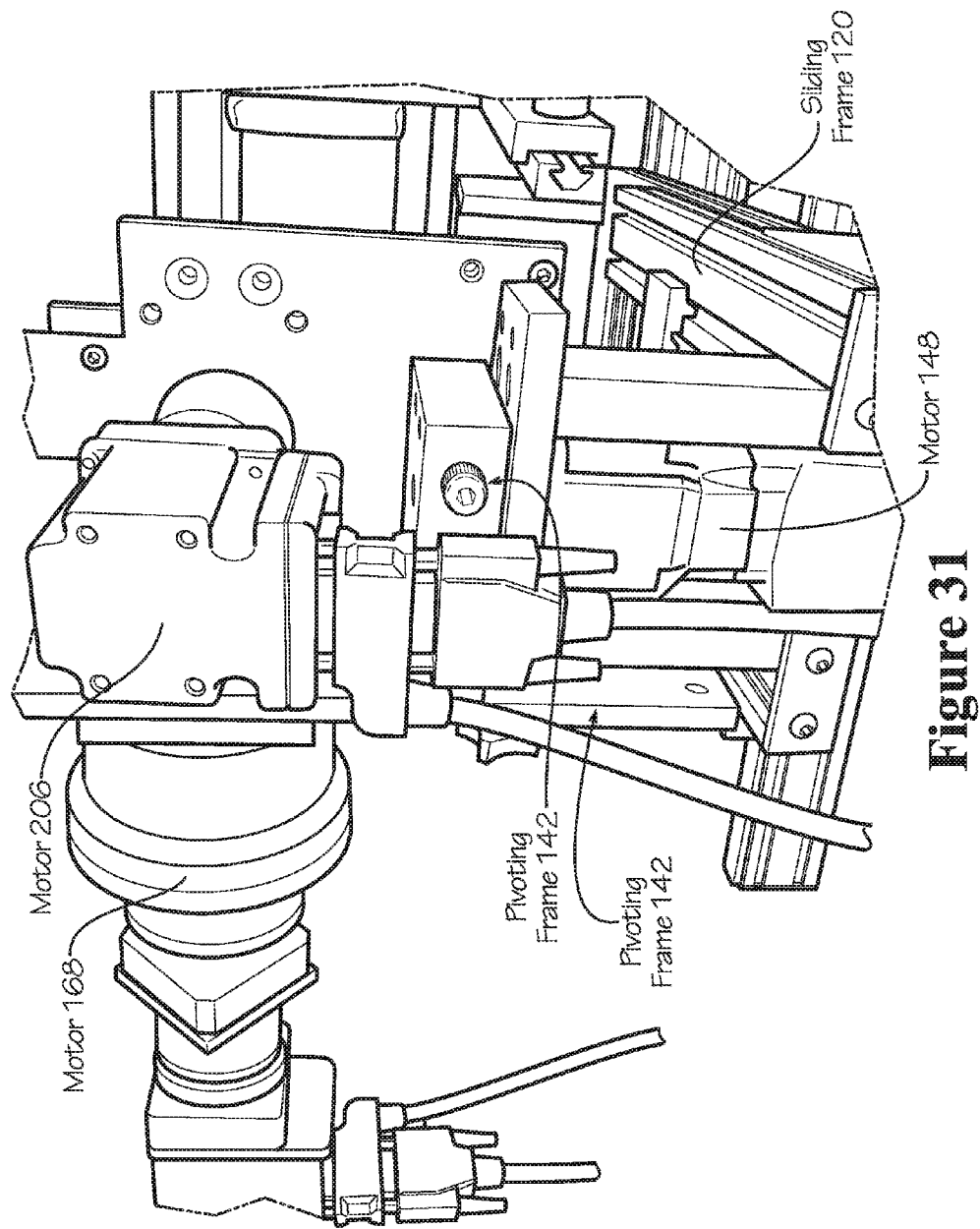

FIG. 31 is a slightly pulled back view than FIG. 30.

Figure 32:
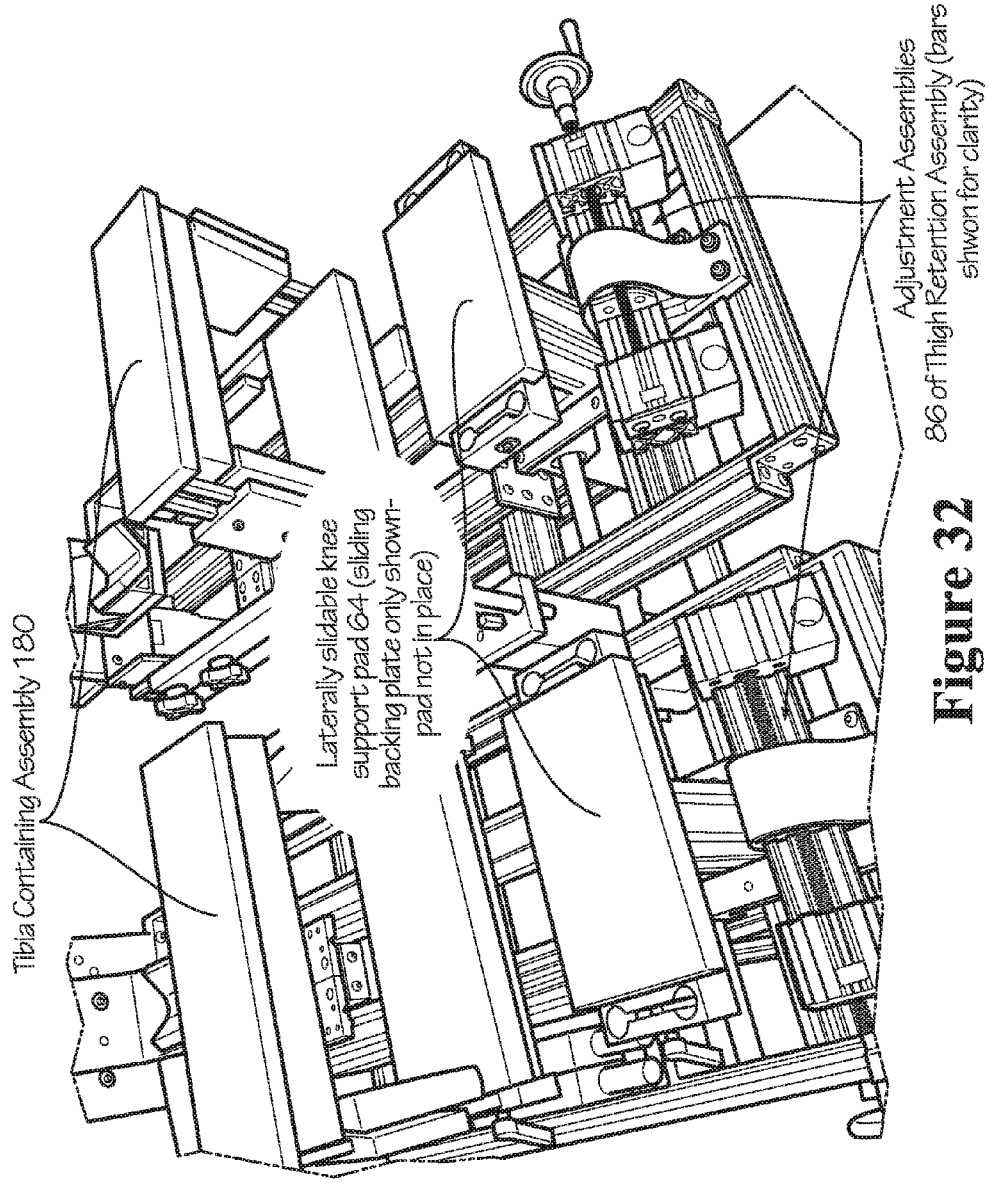

FIG. 32 is a view from the head of the device, without the bars 84 shown for viewing ease.

Figure 33:
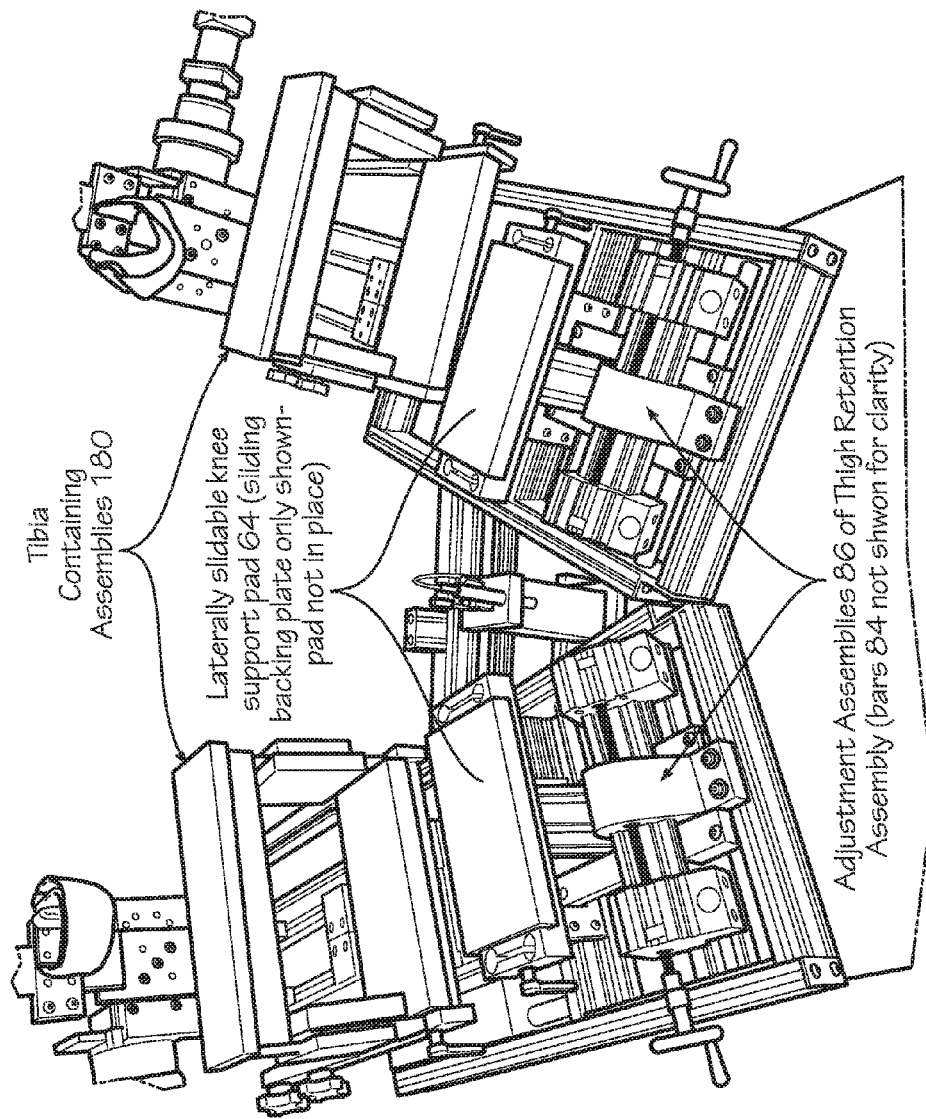

FIG. 33 is a view similar to FIG. 32.

Figure 34:
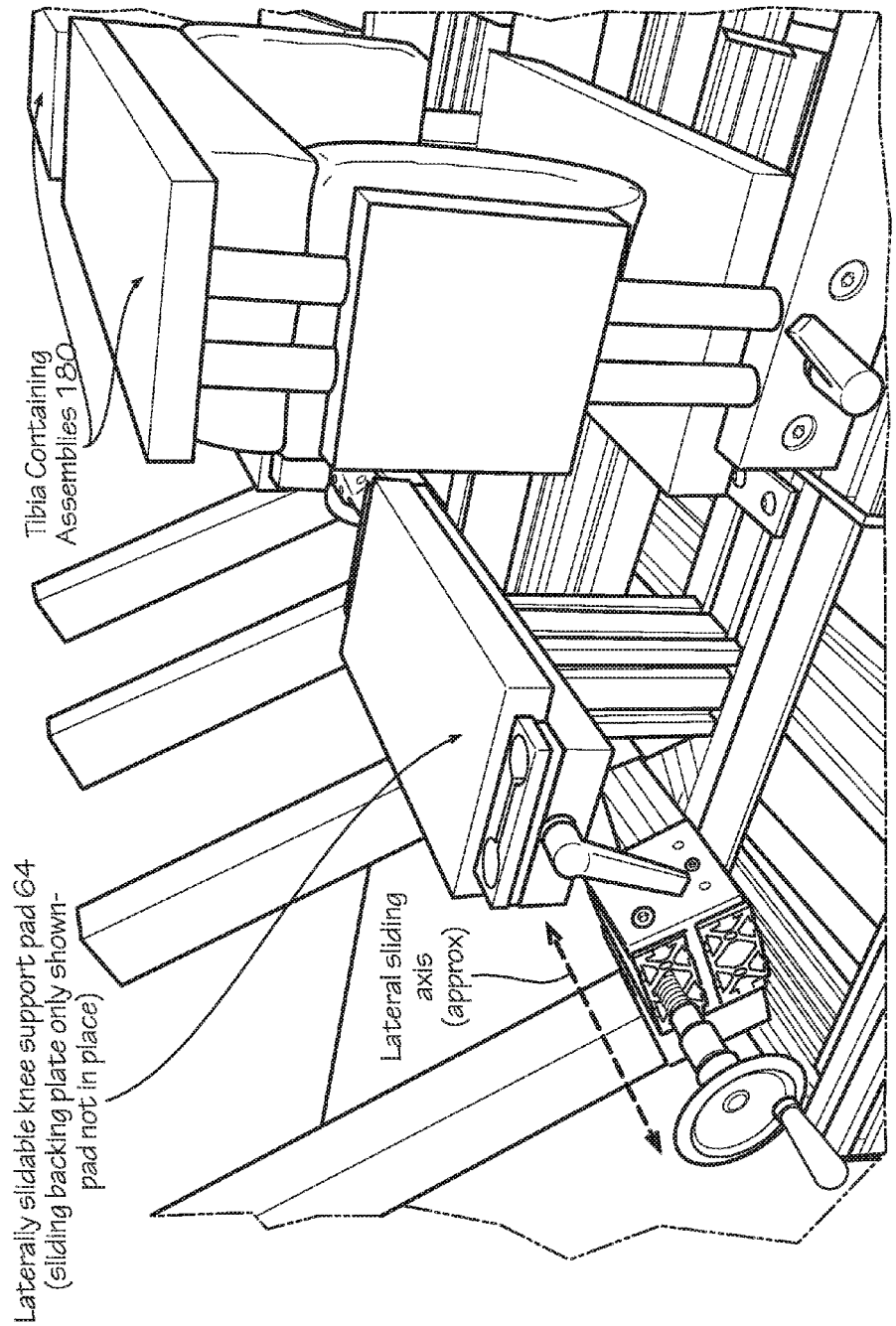

FIG. 34 shows the movement axis of one of the laterally slidable knee support pads 64.

Figure 35:
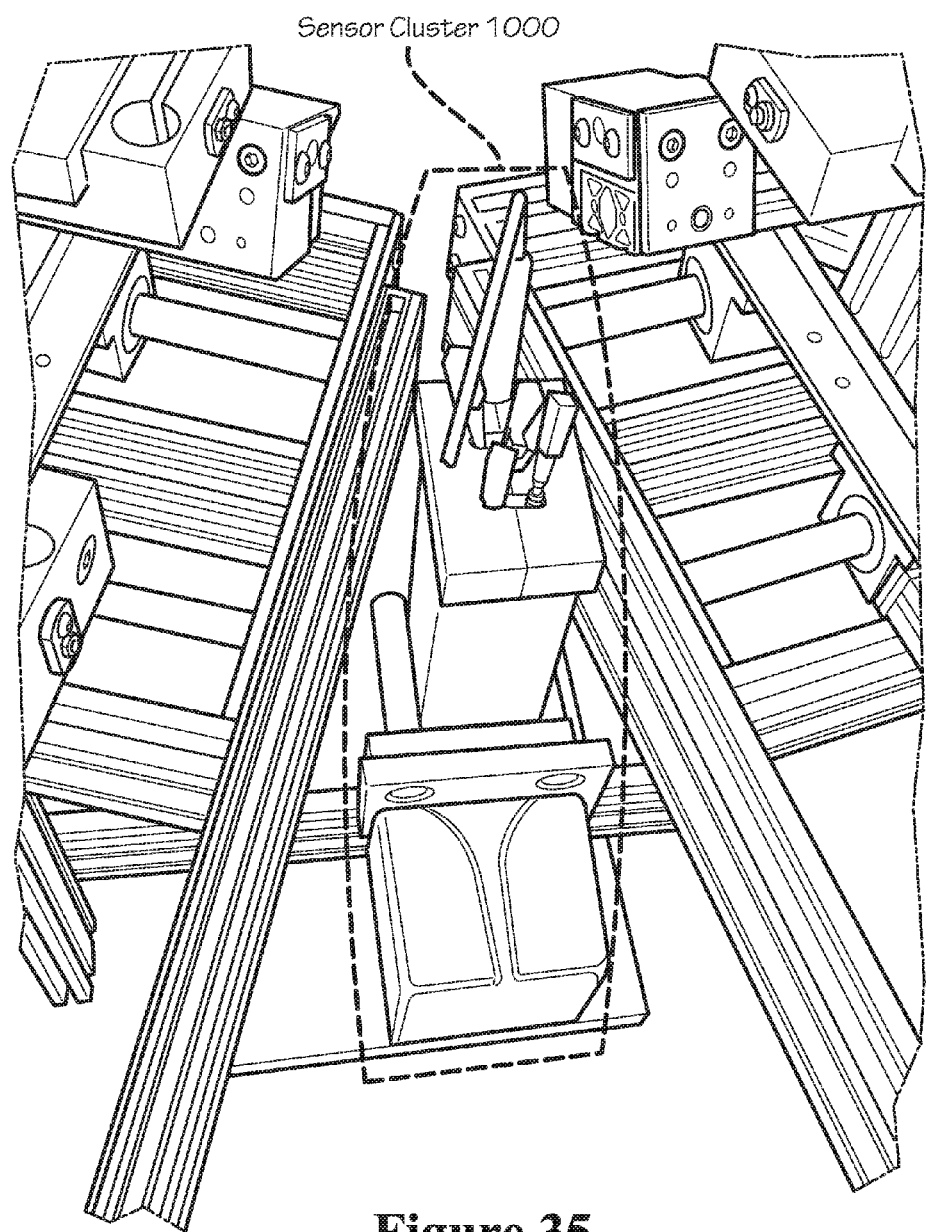

FIG. 35 is a view of an exemplary sensor cluster 1000.

Figure 36:
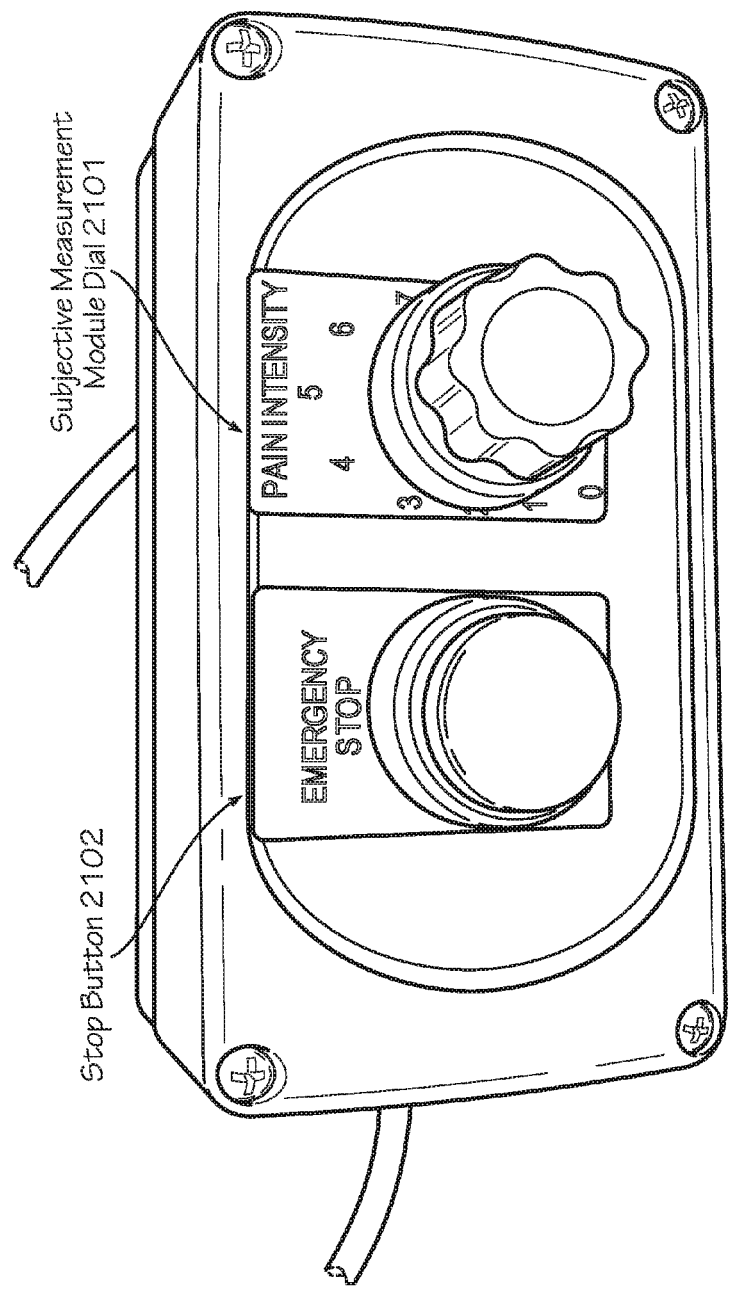

FIG. 36 shows a subjective measurement module 2100 including a subjective measurement module dial 2101 and an overall machine stop button 2102.

Figure 37:
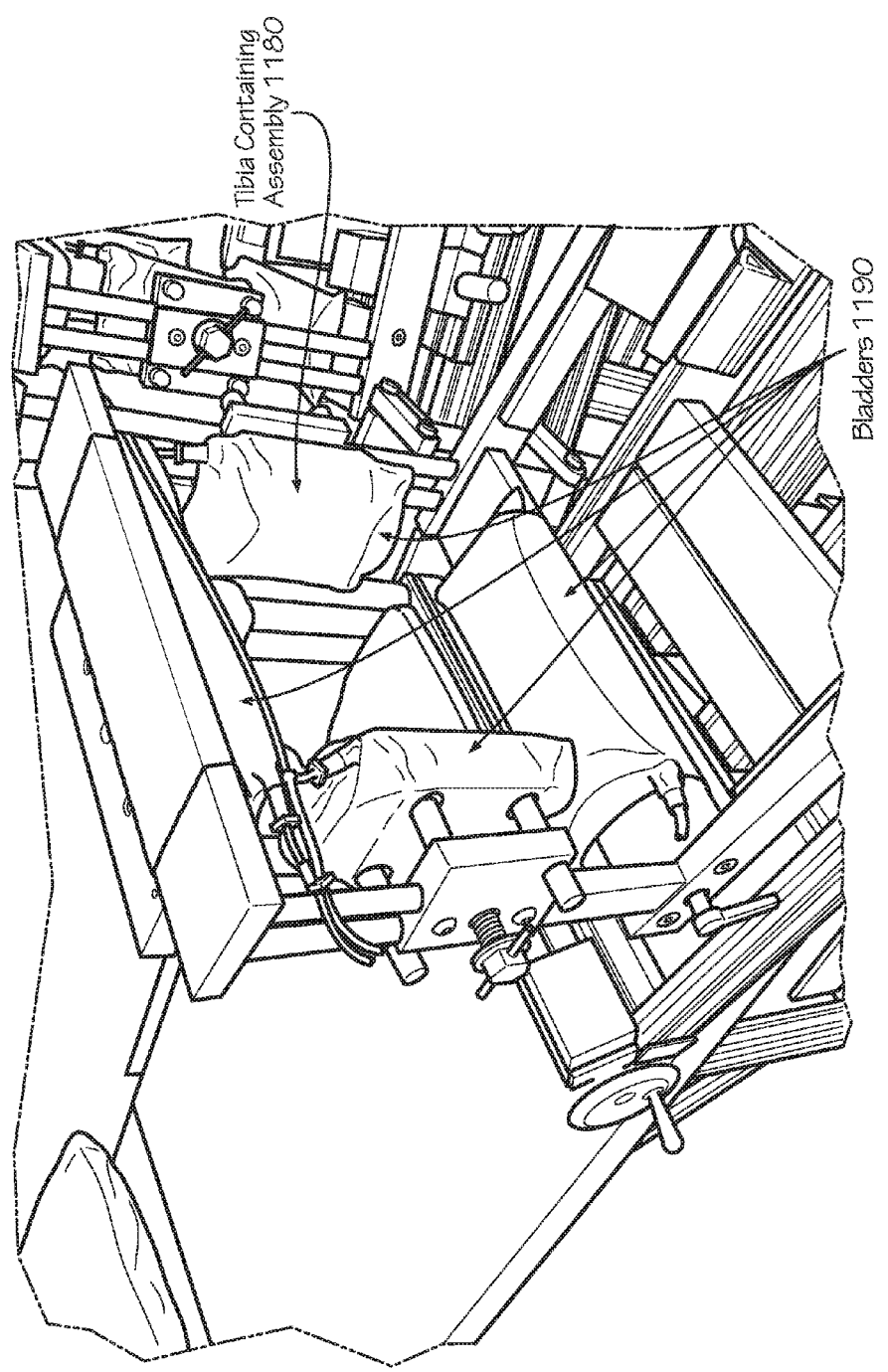

FIG. 37 is a slight overhead view of an additional embodiment of the overall RKT apparatus 10 containing tibia containing assemblies 1180 and a plurality of bladders 1190.

FIG. 38 is a front view of the tibia containing assemblies 1180 and bladders 1190 of FIG. 37.

FIG. 39 is a slight overhead view of an additional embodiment of the overall RKT apparatus 10, together with a system 3000 according to various embodiments for providing accurate and reliable dynamic evaluation of 'joint play.'

DETAILED DESCRIPTION OF VARIOUS EMBODIMENTS

I. General Overview

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Generally described, various embodiments of the present invention provide robotically controlled devices and methods for evaluating the knee, although other joints and limbs can likewise be evaluated such as the elbow and arm. In one aspect of the invention, devices and methods are provided, which apply a known torque to the lower leg of a user and monitor the reaction to this torque at the knee. Such devices and methods may be generally configured to control the direction, rate, and magnitude of force and/or torque application in all three directions (e.g., the x, y, and z axes, as described in further detail below), independently to two legs of a patient. In various embodiments, the user's femur and ankle are stabilized such that the movement of the tibia at the knee in response to a given torque can be accurately measured.

In various embodiments of the present invention, the torque is applied by one or more computer controlled motors. In at least one embodiment, such is accomplished by the use of six (6) brushless servo motors. The computer may be programmed to instruct the motor(s) to perform any desired diagnostic routine. Custom software may be utilized on the computer to calculate the appropriate amount of torque to be used by each motor during testing based on the person's height and weight. The desired torque thresholds are then communicated with the motors.

After the person has been properly positioned, the software may then signal the motor(s) to perform the knee laxity testing. For example, the diagnostic routine may comprise rotating the user's lower leg in a clockwise direction from a neutral position until a predetermined threshold is reached and then back to neutral. This procedure may be repeated for three (3) or more cycles. Then, the user's leg may be rotated from a neutral position in a counterclockwise direction until a predetermined threshold is reached and back to neutral for three cycles. In another example, the diagnostic routine may comprise the rotating of a user's lower leg in a clockwise direction until a predetermined threshold is met and then rotate in a clockwise direction until a predetermined threshold is met in a substantially fluid motion. This procedure may be repeated for several cycles. Clockwise and counterclockwise rotations can be made in either the x, y, or z axes, by placing the motor in different orientations.

In various embodiments, both of the user's lower legs may be rotated simultaneously. For example, the user's left leg may be rotated counter clockwise (external rotation) and then clockwise (internal rotation) while the user's right leg is rotated clockwise (external rotation) and then counter clockwise (internal rotation). By rotating the legs simultaneously in opposite directions, the movement in the hip area can be minimized since the motions counter act each other. This allows evaluation of not only two limbs simultaneously, but also both joints of both limbs (e.g. two knees and two ankles).

While the diagnostic routine is performed, various parameters may be monitored to evaluate the performance of the knee. In one embodiment, angle of rotation and torque measurements are taken at regular intervals during the diagnostic routine. In certain embodiments, the regular intervals may be 120 times per second, collecting the torque currently being applied by each motor and each motor's encoder position. From this data, a hysteresis curve can be generated, which may be used to evaluate the performance of the knee. Further, knee joint laxity may be determined by measuring the amount of motion of the tibia relative to the femur as the tibia is perturbated in single and/or multiplanar motions. More detailed measurement techniques are described elsewhere in this application.

In other embodiments, other methods may be used instead of the motor encoders to measure relative motion of the tibia relative femur or through the use of an external measurement system. External measurement systems can be any number of instrumented systems used to calculate arthrokinematics, including but not limited to electromagnetic, optoelectronic, or ultrasonic motion tracking systems, or other imaging methods such as computed tomography (CT), magnetic resonance imaging (MRI), positron emission tomography (PET), bone scintigraphy (bone scan), dual energy X-ray absorptiometry (DEXA), diagnostic ultrasound, fluoroscopy, radiography, or other imaging methods.

Various embodiments of the present invention further provide an accurate and reliable measure of joint motion in order to better diagnose and treat orthopaedic conditions related to altered joint play. The ideal method to dynamically evaluate joint play is the combination of the accuracy of medical imaging, such as computed tomography (CT), magnetic resonance imaging (MRI), positron emission tomography (PET), bone scintigraphy (bone scan), dual energy X-ray absorptiometry (DEXA), diagnostic ultrasound, fluoroscopy, radiography, or other imaging methods, and the controlled torque application of a computer-controlled motorized system. Due to the potential risks to the clinician or technician associated with medical imaging techniques, the use of medical imaging thus prohibits the clinician from being able to apply the torques necessary to evaluate the joint. A computer-controlled motorized system improves the ability to control torque application without any additional risk to either the patient or clinician.

II. Elements List

The invention is configured to be used by a patient/user 5. The elements of the invention include the following:
- 10. Overall RKT Apparatus
- 20. Stationary Base Frame Assembly
- 30 support cushion
- 40. sliding support framework
  - 42 Clamping members
- 50 Pivoting Leg Support Frame Assemblies (2)
- 60 Knee Support/Stabilizing Assembly
  - 62 telescoping pedestal
  - 64 Laterally Slidable Support pad
  - 66 clamp assembly
  - 68 Top plate
  - 70 rods (4) extending from one side of plate
  - 72 main stabilizing pad
  - 78 rod clamp assembly
- 80 Thigh Retention Assembly
  - 82 Base
  - 84 Retention bars
  - 86 Adjustment Assembly
  - 87 Adjustment Assembly Handwheel
- 100 Tibia Positioning Assembly
- 120 sliding frame
- 140 first pivoting assembly
  - 142 Pivoting frame 148 motor
160 second pivoting assembly
    162 Pivoting frame
    168 motor
180 tibia retention assembly
    182 base
    184 adjustment rods
    185 cap
    186 clamp assembly
    188 Pad support plates
189 pads
200 Third Pivoting Assembly (a.k.a foot rotation assembly 200)
    202 foot plate
    204 rotating shaft
    206 motor
III. Details
Overall RKT Apparatus 10

As illustrated in at least FIGS. 1-2, 19, and 22, various embodiments of the overall RKT (Robotic Knee Testing) Device 10 may include the following features:

Stationary Base Frame Assembly 20;
Support Cushion 30;
Sliding Support Framework 40;
Two (2) Pivoting Leg Support Frame Assemblies 50;
Two (2) Knee Support/Stabilizing Assemblies 60;
Two (2) Thigh Retention Assemblies 80;
Two (2) Tibia Positioning Assemblies 100;
Two (2) Third Pivoting Assemblies 200 (a.k.a. Foot Rotation Assemblies 200).

In use, as will be described in further detail below, a patient 5 may be positioned within the various embodiments of the overall RKT device 10, such that their knees are adjacent the knee support/stabilizing assemblies 60, and their feet are retained within the third pivoting assemblies 200.

Each of these features and their use will now be described in further detail herein-below.

Stationary Base Frame Assembly 20

As illustrated in at least FIGS. 2-4, the stationary base frame assembly 20 according to various embodiments of the overall RKT device 10 is configured to be situated atop and supported by a supporting surface such as a floor (not shown). In certain embodiments, this assembly supports all of the other elements of the overall RKT device 10. In at least one embodiment, the stationary base frame assembly 20 is substantially rigid and is comprised of a plurality of substantially rigid frame members, such as those shown in FIG. 26.

Support Cushion 30

As illustrated in at least FIGS. 2-4, the support cushion 30 according to various embodiments may be configured to be attached to and supported by the stationary base frame assembly 20. In other envisioned embodiments, the cushion 30 may be integrally formed as part of the assembly 20, as illustrated, for example, in FIG. 19 (although not numbered). In any of these and still other envisioned embodiments, the support cushion 30 is generally configured to support the posterior of a patient 5 such that the patient can lie on the patient's back, and the patient's legs can be situated in the overall RKT device 10, as shown for example in at least FIGS. 1, 3, 21, and 23.

Sliding Support Framework 40

As illustrated in at least FIGS. 2-4 and 26, the sliding support framework 40 according to various embodiments, may comprise a substantially rigid substructure slidably supported atop the stationary base frame assembly 20. In this manner, the support framework 40 may, in these and still other envisioned embodiments, be configured to slide relative to the stationary base frame assembly 20 along a linear X axis. This movement is designated as "Action A" by the arrows in, for example, FIG. 2.

In various embodiments, the "Action A" movement is configured to facilitate adjustment of the sliding support framework 40 prior to its testing function. In certain embodiments, this adjustment allows for the sliding support framework 40 to be properly positioned relative to the patient. This adjustment is not made to accommodate varying leg lengths, but allows for proper positioning of the testing apparatus even if the patient is positioned too far toward either the head or foot of the bed. While in the embodiment shown in FIG. 2 this adjustment is along the X axis and is linear, alternative possible, single or multiple, axes of adjustment may be envisioned as within the scope of the present invention.

As will be described below in further detail, the two pivoting leg support frame assemblies 50 according to various embodiments may be attached above and supported by the sliding support framework 40. In this manner, in at least certain embodiments, the frame assemblies 50 may be likewise adjusted as the sliding support framework 40 is adjusted, as may be desirable for particular applications.

In use, according to various embodiments, in order to adjust the sliding support framework 40 relative to the stationary base frame assembly 20, the patient 5 (a.k.a. user 5) may be first positioned in place as generally shown in at least FIGS. 1 and 3. During such positioning, a releasable connection 42 according to various embodiments between the sliding support framework 40 and the stationary base frame assembly 20 is disengaged, thereby permitting adjustment of the framework 40 relative to the assembly 20, as necessary to fine-tune the positioning of the patient 5. In at least one embodiment the releasable connection comprises at least two clamping members 42, as illustrated in FIG. 3, although in other envisioned embodiments, any of a variety of alternative type or number of connections may be employed between the sliding support framework 40 and the stationary base frame assembly 20.

In any of the above-discussed embodiments, once the patient is positioned precisely as desired or needed, then the releasable connection 42 between the sliding support framework 40 and the stationary base frame assembly 20 may be engaged (see e.g., clamps 42 in FIG. 3). In this manner, once the connection or clamps 42 are engaged, relative movement between the framework 40 and the assembly 20 may be prevented, so as to maintain the patient 5 in the proper or desired position.

Two (2) Pivoting Leg Support Frame Assemblies 50

As illustrated in at least FIGS. 2-4 and 26, the general function of each of the two pivoting leg support frame assemblies 50 according to various embodiments of the overall RKT device 10 is to provide a framework to support a corresponding leg of the patient/user such as 5.

In various embodiments, the two pivoting leg support frame assemblies 50 are pivotably attached above and supported by the sliding support framework 40. In this manner, the assemblies 50 may be likewise adjusted as the sliding support framework 40 is adjusted, as previously described herein and as illustrated in, for example FIGS. 6, 7, and 9.

In various embodiments, each of the two pivoting leg support frame assemblies 50 is pivotably mounted relative to the framework about an axis lying parallel to the Y axis (see FIG. 2); thus they lie substantially along mutually parallel axes. In these and other embodiments, as best understood from FIG. 6, the pivoting actions of the assemblies 50 may be independent, in that one can pivot without the other. In still other envisioned embodiments, depending upon a particular application, the pivoting actions of the assemblies 50 may be interdependent, illustrated, at least in part by FIG. 10. In any of these described and still further envisioned embodiments, the pivoting action is an adjustment such as that identified as "Action B" in, for example, FIG. 2 and more fully illustrated in FIG. 8. Action B adjustment allows the individual leg testing apparatuses to be aligned according to the patient's natural alignment. Improper alignment would pre-tension ligaments thus creating error in the test results. This adjustment is made to avoid such errors.

According to various embodiments, each pivoting leg support frame assembly 50 is substantially similar to the other, and thus one can be described as an example of the other. In other envisioned embodiments (not shown), however, each of the assemblies 50 may differ in one or more respects, as may be desirable for a particular application.

Further, as noted above, each pivoting leg support frame assembly 50 may, according to various embodiments, comprise a substantially rigid substructure. In certain embodiments, each pivoting leg support frame assembly 50 itself slidably supports a corresponding one of two tibia positioning assemblies 100, as illustrated in, for example, FIG. 3, and described in further detail below. In various embodiments, as one pivoting leg support frame assembly 50 pivots, so does its corresponding tibia positioning assembly 100. However, it should be appreciated that in still other envisioned embodiments, the respective assemblies 50 and their corresponding assemblies 100 may one or both pivot independently relative to one another, in any of a variety of combinations, as may be desired for a particular application.

According to various embodiments, the pivoting movement of the respective assemblies 50 and their corresponding assemblies 100 is substantially about an axis parallel to the "X" direction, as illustrated in, for example, FIG. 2. In at least one embodiment there are no clamps between 50 and 100, although the pivoting movement could be prevented via clamping after suitable adjustment. In the embodiment without clamps, each of the two pivoting leg support frame assemblies 50 is free to pivotably relative to the sliding support framework 40.

Two (2) Knee Support/Stabilizing Assemblies 60

As illustrated in at least FIGS. 13 and 14, the general function according to various embodiments of the knee support/stabilizing assemblies 60 is to support the knee, when in their "support mode" (see FIG. 13), and to support and stabilize the knees when in their "stabilizing mode" (see FIG. 14). In certain embodiments, the knee support/stabilizing assemblies 60 are used in support mode for varus-valgus testing. In those and other embodiments, the knee support/stabilizing assemblies 60 are used in "stabilizing mode" for both antero-posterior and rotational testing. In still other embodiments, the knee assemblies 60 may be used in either support or stabilizing mode for any of a variety of tests, as may be desired for a particular application. Each of these modes will be discussed in further detail below, although it should be further appreciated that at least certain envisioned embodiments will include no knee support/stabilizing assemblies 60 of any kind, as illustrated, for example, in FIGS. 23 and 27.

Support Mode (Generally Used in Varus-Valgus Testing)

As best illustrated in FIGS. 13 and 21, according to various embodiments, the knee support/stabilizing assemblies 60 may be used in support mode for varus-valgus testing. When in "support mode", the knee support/stabilizing assemblies 60 only support the knee region of the leg from underneath, and is free to move side to side. When in this mode, each of the knee support/stabilizing assemblies 60 includes the following elements, as illustrated in at least FIGS. 11 and 13:

Telescoping Pedestal 62
Laterally Slidable Knee Support Pad 64 (slidable in this mode)
Clamp Assembly 66
Plate 68
Rods 70 (4) extending from one side of plate
Stabilizing Pad 72

According to various embodiments, the telescoping pedestal 62 has a lower end which is configured to be attached atop a corresponding pivoting leg support frame assembly 50. In certain embodiments, the telescoping pedestal 62 supports at its top end a laterally slidable knee support pad 64, which is configured to contact and support a portion of the leg of a patient 5 proximate the knee as shown in for example FIG. 3. When in this mode, according to these and other envisioned embodiments, the pad 64 may be free to move laterally along with the underneath portion of the leg being supported. This is also known as Action J, as illustrated in at least FIG. 13.

With reference to FIG. 13 in view of FIG. 3, according to various embodiments, during varus-valgus testing, as the device rotates about pivot point shown in Action F, it will be necessary to allow the knee move laterally side to side in order to actually perform the test. This is facilitated by the provision of the laterally slidable knee support pad 64. Further according to various embodiments, during the varus-valgus testing, the knee itself need not be stabilized as in the anteroposterior and rotational tests described immediately below. However, the proximal thigh may, in certain embodiments, be stabilized by the thigh retention assembly 80 while the foot may be stabilized by the foot rotation assembly 200, as illustrated in at least FIG. 3, for example.

Therefore it may be seen that the knee support/stabilizing assemblies 60 may be used according to various embodiments in support mode to allow for a consistent degree of knee flexion during varus-valgus testing. Such benefit arises in at least certain embodiments due to the sliding pads 64 allowing the knees to slide laterally or otherwise, as previously described herein.

Stabilizing Mode (Generally Used in Antero-Posterior and Rotational Testing)

According to various embodiments, as illustrated in at least FIGS. 14 and 25, the knee support/stabilizing assemblies 60 may likewise be used in "stabilizing mode" for both antero-posterior and rotational testing. In these and other embodiments, during anteroposterior and rotational testing, a clamp assembly 66 may be added to minimize motion of the femur, as described in further detail below.

When in "stabilizing mode" according to various embodiments, each of the knee support/stabilizing assemblies 60 may include one or more of the following elements, generally depicted in FIGS. 11 and 14, as will be described in further detail below:

Telescoping Pedestal 62
Support Pad 64
Clamp Assembly 66
Top Plate 68
Rods 70 (4) extending from one side of plate
Main Stabilizing Pad 72
Rod clamp assembly 78

In certain embodiments, the knee support/stabilizing assemblies 60 may be used in stabilizing mode to allow for a consistent degree of knee flexion, as was done during varus-valgus testing described above. However, when in stabilizing mode, each of the knee support/stabilizing assemblies 60 also includes a clamp assembly 66, as described in further detail below.

This clamp assembly 66 according to various embodiments may be configured to cooperate with the support pad 64 so as to substantially encircle the leg and to substantially engage or grip it from the top, as illustrated in at least FIGS. 14 and 21 (in the latter as assembly 60 generally). When in this mode according to certain embodiments, the pad 64 may not be adjusted laterally relative to the general longitudinal axis of the leg, as it is captured on its ends by at least the rods 70. According to these and other envisioned embodiments, the clamp assembly 66 may include the following:

Top Plate 68
Adjustment Rods 70 (4) extending from one side of plate
Main Stabilizing Pad 72
Rod clamp assembly 78

According to various embodiments, the top plate 68 may be configured such that the upper ends of four rods 70 may be attached to its underside. So configured, the rods 70 in at least certain embodiments may extend substantially downwardly and slidably into through-holes defined by the pedestal 62 until they are clamped in place. In at least one embodiment, the rod clamp assembly 78 is configured to clamp the rods relative to the pedestal 62 such that the top plate 68 is retained in place. When so retained according to these and still other embodiments, the pads 64 and 72 substantially surround and contact the patient's leg, as illustrated in at least FIG. 14. In still other envisioned embodiments, the rods 70 themselves may also provide some degree of containment of the patient's leg.

Remaining with FIG. 14, according to various embodiments, the shape of pad 72 may be at least in part dictated by the need to stabilize the patella within the femoral trochlea. Such stabilization, in certain embodiments, prevents undesirable rotation and anteroposterior translation of the femur, while also satisfying a need to place an electromagnetic sensor, retro-reflective ball or array, ultrasonic sensor, or other motion tracking device on the patella. In certain embodiments, the pad may be "V-shaped," which then allows the device to adequately capture the patella no matter the patellar dimensions of a given patient. In these and still other embodiments, the apex of the "V" shape may be deepened and/or widened in order to create a channel or pocket for the motion tracking device to be placed on the patella, as may be desired for a particular application.

In various embodiments, adjustments may be made such that the rod clamp assembly 78 is applied around the patient's leg, and in particular the patient's patella, by using a consistent known amount of force. For example, a downward (e.g., posteriorly-directed) force of 25 pounds may be used when positioning all patients. In these and still other envisioned embodiments, a substantially consistent force should be used to allow for accurate and repeatable side-to-side comparisons. Indeed, inconsistent force application would allow one femur to be more easily moveable than the other, thus potentially creating error in the bilateral comparisons of translation and rotation of the tibia relative to the femur between the person's right and left knees.

Height Adjustment of Knee Support/Stabilizing Assemblies 60

Whether or not the knee support/stabilizing assemblies 60 according to various embodiment are configured in support or stabilizing mode, the height the assemblies support the leg may be variable via adjustment of the telescopic portion of the telescoping pedestal 62. This adjustment is illustrated as Action D in at least FIG. 2.

According to various embodiments, Action D adjustment may be provided either prior to testing in one embodiment or to change the degree of knee flexion in an effort to be consistent with previously accepted clinical evaluation procedures, as may be desirable or necessary for a given application.

Two (2) Thigh Retention Assemblies 80

As illustrated in at least FIG. 12, the general function of each of the thigh retention assemblies 80 is to retain the thigh of the patient/user 5 such that internal/external and varus/valgus rotations of the femur are limited.

According to various embodiments, each thigh retention assembly may include two retention bars 84, which are positioned on either side of the thigh of the patient/user's 5 thigh 82 so as to discourage it from movement lateral to the longitudinal axis of the tibia. In certain embodiments, the two retention bars 84 are configured for centered adjustment, in that they are commonly mounted within an adjustment subapparatus that facilitates their common adjustment relative to a common central point. In this manner, in at least one embodiment, as one bar is moved a given distance in one lateral direction, the other bar moves a given distance in the opposite lateral direction. This allows tightening or loosening of the bars about the intermediate thigh without moving the thigh to one side or the other. This could be considered a "self-centering" feature in at least certain of the envisioned embodiments.

Turning now to FIG. 11, each thigh retention assembly 80 according to various embodiments may include the following:

Base 82
Two (2) Retention bars 84
Adjustment Assembly 86 (see also FIGS. 32 and 33)
Adjustment Assembly Handwheel 87

According to various embodiments, the base 82 of the thigh retention assembly 80 may be rigidly attached atop a corresponding one the pivoting leg support assemblies 50. In certain embodiments, the base 82 may support a corresponding adjustment assembly 86, which in turn may adjustably support two retention bars 84, as further illustrated in at least FIG. 12. In operation according to at least one embodiment, an adjustment assembly hand wheel 87 allows an operator (such as a clinician, not shown) to rotate the hand wheel 87. Rotation of the hand wheel 87 in this manner, according to various embodiments, rotates a threaded rod (or analogous mechanism, as commonly known or understood in the art) having two threaded portions of opposite direction, each one engaging relative to one of the retention bars 84, such that adjustment of the spacing of the two retention bars 84 is facilitated such that a thigh can be suitably clamped therebetween.

Each of the two thigh retention assemblies 80 may according to various embodiments be attached atop a corresponding pivoting leg support frame assembly 50, such that pivoting of the pivoting leg support frame assembly 50 about its vertical axis (e.g., during adjustment, as previously described herein) likewise facilitates pivoting of the corresponding thigh retention assembly 80.

During patient set-up, it should be understood that the two retention bars 84 may generally squeeze the thigh in order to stabilize the femur while ensuring that the femur is centrally located in relation to both of the retention bars.

Two (2) Tibia Positioning Assemblies 100

Returning now to FIGS. 2 and 3, the general function of each of the two tibia retention assemblies 100 according to various embodiments is to position the tibia of the patient/user 5. In certain embodiments, each of the tibia retention assemblies 100 includes the following features:

sliding frame 120 first pivoting assembly 140 second pivoting assembly 160

According to various embodiments, the sliding frame 120 of the tibia positioning assembly 100 provides the sliding connection between the tibia positioning assembly 100 and the pivoting leg support frame assembly 50, as there is a sliding connection between elements 50 and 120, which is Action E. Action E, as illustrated in at least FIG. 2 provides a degree of adjustment, which allows the tibia positioning assembly 100 to be adjusted according to the patient's leg length.

First Pivoting Assembly 140

Turning now to FIG. 5, the first pivoting assembly 140 according to various embodiments may be pivotably mounted relative to the sliding frame 120 of the tibia positioning assembly 100. In this manner, in certain embodiments, the first pivoting assembly 140 may be configured to pivot relative to sliding frame 120 via Action "F" (see e.g., FIG. 2), about a vertical axis along the "Y" axis.

Remaining with FIG. 2, it should be understood that Action "F" action according to various embodiments is driven and controlled by motors 148 (see at least FIGS. 30 and 31), and provides a varus-valgus torque to the knee. Such action around the axis of rotation is used for valgus-varus or medial-lateral testing. One current embodiment uses a servomotor to provide the rotational force, although other manual or mechanical methods of force application could be used.

According to various embodiments, the first pivoting assembly 140 includes the following:

Pivoting frame 142 (See, e.g., FIG. 16)

Motor 148 (see at least FIGS. 30 and 31)

Focusing upon at least FIG. 16, it should be understood that the pivoting frame 142 according to various embodiments provides the pivoting connection between the first pivoting assembly 140 and the sliding frame 120 and in at least certain embodiments the motor 148 (see FIGS. 30 and 31) drives this pivoting action. Further, in at least certain embodiments, the pivoting frame 142 may be configured in substantially the same manner as pivoting frame 162, as will be described in further detail here-below. In other embodiments, the pivoting frame 142 and frame 162 may be substantially different in shape, size and/or configuration, as may be desired for a particular application.

Second Pivoting Assembly 160

Returning to FIG. 5, the second pivoting assembly 160 according to various embodiments may be configured to be pivotably mounted relative to the first pivoting assembly 140, such that the second pivoting assembly 160 pivots relative to the first pivoting assembly 140 via Action "G" (see FIG. 2), about a horizontal axis shown by pivot point GPP (see FIG. 4). In certain embodiments, this axis is the axis of rotation (normal to the drawing plane, in axis "Z") for anteroposterior laxity testing, causing the rotation indicated as Action G. At least one current embodiment uses a servomotor 168, as illustrated in at least FIG. 5, so as to provide the rotational force, although other manual or mechanical methods of force application may be envisioned and/or used, as desirable for any of a variety of applications.

According to various embodiments, Action G, whether manually driven or driven and controlled by motors 168, is configured to provide internal-external rotation torque to the tibias, as will be described in further detail below. In these and still other envisioned embodiments, the second pivoting assembly 160 may include any or all of the following features:

Pivoting frame 162

Clamp 163 (see FIG. 5)

Motor 168 (see FIGS. 5 and 27-29 and 31)

Tibia Retention Assembly 180

The pivoting frame 162 according to various embodiments provides the pivoting connection between the second pivoting assembly 160 and the first pivoting assembly 140, and in at least the illustrated embodiment the motor 168 drives this pivoting action. In other embodiments, as previously described, alternative manual or mechanical methods and/or devices may be employed. In any of these and other envisioned embodiments, the tibia retention assembly 180, as illustrated in at least FIGS. 20, 21 and 25, may be configured to be attached at the free end of the pivoting frame 162. According to various embodiments, the location along the patient/user's leg that the tibia retention assembly 180 contacts the leg may be adjustable via Action "I" as illustrated in at least FIGS. 2, 4, and 5, which is an adjustment of the length of the pivoting frame 162.

Turning specifically to FIG. 4, Action I adjustment according to various embodiments, may be provided so that the location of force application during the anteroposterior, mediolateral, or valgus/varus testing can be held consistent for each patient. For example, the location of force application may need to be 1" distal to the tibial tuberosity; therefore, this portion of the frame must be adjusted so that the location of force application can be consistently located for patients. Once Action I adjustment is provided clamps such as 163, as provided according to various embodiments, may be clamped down so Action I movement is restricted. In other embodiments, any of a variety of commonly known and understood mechanisms may be used and operated so as to selectively permit and/or restrict Action I movement.

Tibia Retention Assembly 180

Referring now to at least FIGS. 5 and 15, the tibia retention assembly 180 according to various embodiments may be configured to laterally retain the tibia during at least the anteroposterior and varus-valgus testing processes. In at least certain embodiments, the tibia retention assembly 180 includes the following, each of which as illustrated in at least FIG. 15:

Base 182

Adjustment rods 184

Cap 185

Clamp assembly 186

Pad support plates 188

Pads 189

According to various embodiments, the base 182 of the tibia retention assembly 180 may be attached to the free end of the free end of pivoting frame 162 (which as seen in FIGS. 5 and 24 may comprise one or more pair of telescoping rails). In certain embodiments, the two rail-like free ends of the pivoting frame 162 each define holes through which the adjustment rods 189 can slidably fit until they are clamped in place. The adjustment rods 189 all have one end rigidly mounted to the cap 185. In at least one embodiment, the clamp assembly 186 may be configured to clamp the rods relative to the base such that the cap 185 is retained in place. In these and still other envisioned embodiments, the pads 189 may be configured to substantially surround and contact the patient/user's leg. In at least the illustrated embodiment of FIG. 15, the pads are attached to the rods via the pad support plates 188, although in still other envisioned embodiments, the pads may be attached relative to the rods via any of a variety of methods and devices, as commonly known and understood in the art and desirable for a given application.

Remaining with FIG. 15, adjustment of the clamp assembly 186 according to various embodiments may be made such that the location of the anterior pad (185 attached to 189) is 1-2 cm above the anterior aspect of the low leg, with the entire system rotated about pivot point GPP so that the posterior pad (182 attached to 189) is located 1-2 cm below the posterior aspect of the low leg. Tightening the clamp assembly 186 fixes this position allowing for the system to function rigidly during anteroposterior and varus-valgus testing, and further allows for subtle changes in tibial anteroposterior position during rotational testing.

Tibia Retention Assembly 1180

Referring now to at least FIGS. 37 and 38, an alternative tibia retention assembly 1180 according to various embodiments may be configured substantially the same as tibia retention assembly 180 so to laterally retain the tibia during at least the anteroposterior and varus-valgus testing processes. In at least certain embodiments, the tibia retention assembly 1180 further includes a plurality of bladders 1190 configured for applying a force so as to retain at least a portion of the patient's tibia within the assembly. In at least one embodiment, the plurality of bladders 1190 are contained within corresponding cuffs that are positioned relative to the assembly 1180 such that two cuffs are adjacent opposing side portions of the assembly, one cuff is adjacent a top portion of the assembly, and one cuff is adjacent a bottom portion of the assembly, as best illustrated in at least FIG. 38. In other embodiments, any combination of bladders 1190 and cuffs may be incorporated (e.g., merely one atop and one below the leg or merely two side opposing ones) as may be desired for a particular application.

In use according to various embodiments, each of the bladders 1190 may be selectively inflated so as to apply or increase a corresponding force to the portion of the patient's tibia positioned substantially adjacent each bladder. In certain embodiments, the bladders 1190 may be likewise selectively deflated so as to remove or decrease the corresponding force, as desirable. In at least these and other envisioned embodiments, the bladders 1190 may all be inflated and/or deflated simultaneously, while in still other envisioned embodiments, each of the bladders 1190 may be manipulated individually.

According to various embodiments, a single pressure sensor may be connected to the bladders 1190 (e.g., via the lines or tubes, as seen (but not numbered) in at least FIG. 38)) and used to measure the change in pressure for the same. In certain embodiments, multiple pressure sensors may be employed, as may be desirable for a particular application. Still other embodiments may employ additional and/or alternative sensors or measurement tools, as may be desired.

Two (2) Third Pivoting Assemblies 200 (a.k.a. Foot Rotation Assemblies 200)

Returning again to FIG. 5, each third pivoting assembly 200 according to various embodiments includes at least the following features:

foot plate 202
rotating shaft 204
motor 206

According to various embodiments, the foot plate 202 of each of the third pivoting assembles 200 may be pivotably mounted relative to the pivoting frame 162 of the second pivoting assembly 160 via a rotating shaft 204, such that the foot plate 202 pivots relative to the pivoting frame 162 via Action "H," as illustrated in at least FIG. 4.

Action "H" of FIG. 4 is powered movement about an axis of rotation for tibial internal and external rotation testing. At least one current embodiment uses a servomotor 206 to provide the rotational force, although other manual or mechanical methods of force application could be used, as desirable for any of a variety of given applications, as commonly known and understood in the art. In these and still other embodiments using the motor 206, such may be configured with a housing mounted relative to the pivoting frame 162, such that the motor drives the rotating shaft 204, which itself drives the foot plate 202. Of course, it should be understood that any of a variety of alternative configurations may be envisioned as within the scope of the present invention, as may be desirable for a given application.

Actions of the Apparatus

Reference is made to FIGS. 2 and 3, which show all the actions performed by various embodiments of the overall RKT device 10. These actions are designated primarily upon FIG. 2, with capital letters in circles; for example Action is designated with a circle with an "A" inside.

Action A—This adjustment according to various embodiments allows for the entire testing system to be properly positioned relative to the patient. This adjustment is not made to accommodate varying leg lengths, but allows for proper positioning of the testing apparatus even if the patient is positioned too far toward either the head or foot of the bed. In at least the shown embodiment this adjustment is along the X axis and is linear.

Action B—This adjustment according to various embodiments allows the individual tibia positioning assemblies to be aligned according to the patient's natural alignment, as may be seen in at least FIGS. 8 and 10, respectively. Improper alignment can potentially pre-tension ligaments, thus creating error in the test results. The adjustment of Action B according to various embodiments is made to avoid such errors. In one embodiment, the tibia positioning assemblies are able to be moved by hand on sliding contact C; however, the coefficient of friction is such that the valgus-varus position of the tibia positioning assemblies may be maintained during laxity testing. In another embodiment the tibia positioning assemblies pivot freely and independently, including during testing, to allow for proper varus-valgus alignment of the limb to match the person's natural alignment. In another embodiment, the tibia positioning assemblies are clamped relative to their supporting frame just prior to testing.

Action C—This is a frictional sliding contact point (1 of 2) which supports the tibia positioning assemblies as they pivot according to various embodiments.

Action D—As noted above, Action D adjustment is provided prior to testing in one embodiment to change the degree of knee flexion in an effort to be consistent with previously accepted clinical evaluation procedures. However, alternate embodiments and methods include the use of automated actions to perform more complicated, multi-planar motions. For example, the apparatus could be so used to simulate the pivot shift test which involves applying internal rotation and valgus torques while at the same time increasing the degree of knee flexion. As noted, Action D according to these and still other envisioned embodiments changes the degree of knee flexion.

Action E—This adjustment according to various embodiments allows the tibia positioning assembly 100 to be adjusted according to the patient's leg length. In a second embodiment, this action can be automated with the use of a ball screw, worm gear, or other motorized linear actuator. The entire tibial positioning assembly 100 may then be moved closer to or further away from the support cushion 30. Moving the tibial positioning assembly closer to the support cushion would increase the degree of knee flexion and moving further away from the support cushion 30 would then move the knee into extension. This allows, in at least certain embodiments, for individualized static positioning of the knee for each person or would allow for the degree of knee flexion or extension to be changed during laxity testing, and could be coordinated to perform multiplanar testing with any or all of the three testing axes (Actions F, G, and H).

Action F—This action according to various embodiments is driven and controlled by motors 148, and provides a varus-valgus torque to the knee. Such action around the axis of rotation is used for valgus-varus or medial-lateral testing. At least one envisioned embodiment uses a servomotor to provide the rotational force, although other manual or mechanical methods of force application could be used.

Action G, about Pivot Point GPP—According to various embodiments, GPP is the axis of rotation (normal to the drawing plane, in axis "Z") for anteroposterior laxity testing, causing the rotation indicated as Action G. At least one envisioned embodiment uses a servomotor 168 to provide the rotational force, although other manual or mechanical methods of force application could be used.

Action H—This is the axis of rotation for tibial internal and external rotation testing according to various embodiments. At least one envisioned embodiment uses a servomotor 206 to provide the rotational force, although other manual or mechanical methods of force application could be used.

Action I—This action may be adjusted according to various embodiments so that the location of force application during the anteroposterior, mediolateral, or valgus/varus testing can be held consistent for each patient. For example, the location of force application may need to be 1" distal to the tibial tuberosity; therefore, this portion of the frame must be adjusted so that the location of force application can be consistently located for patients.

Action J—This action according to various embodiments is lateral sliding movement of laterally slidable knee support pad 64 knee support/stabilizing assembly 60. The laterally slidable knee support pad is slidably mounted relative to the pedestal 62 of the knee support/stabilizing assembly 60, such that it can move about an axis such as shown by the arrows in FIGS. 15 and 34.

Input/Output Signals of the Device

As may be seen from FIGS. 27-31, various embodiments of the testing procedures made possible by the overall RKT device 10 may be accomplished by the use of six (6) brushless servo motors, namely two motors 148, two motors 168, and two motors 208. It should be understood that fewer or additional motors may be employed, as may be desirable for any of a variety of envisioned applications, in particular those involving one or more manual inputs, as previously described herein.

In certain embodiments, perhaps best illustrated in FIG. 31, all input and output signals are accomplished through the use of these motors. However, it should be noted that other motion tracking systems may be used in conjunction with the motors in order to accurately and reliably measure motion of the tibia relative to the femur. Examples of motion tracking systems would include, but not limited to, optoelectronic, electromagnetic, ultrasonic, fluoroscopic, stereo bi-plane radiographic, and other imaging methods commonly used to measure motion of the tibia relative to the femur in vivo.

According to various embodiments, input signals are sent to the motors regarding the target torque thresholds for each of the three tests for each patient, as well as the signals to start and complete each test. In a similar fashion according to various embodiments, output signals are sent from or regarding the motors regarding the amount and direction of torque from each motor as well as the encoder count for each motor.

The Testing Processes

As may be understood at least initially from FIG. 1, the patient 5 may be positioned supine, and motion tracking sensors are applied to each tibia, femur, and the patella as needed. The patient's feet are then strapped into the corresponding Foot Rotation Assemblies 200.

The underlying rationale of the laxity testing methods described in the following paragraphs is that the tibia, which is an intercalary bone, is perturbated in a given direction by the device, and the motion of the tibia relative to the femur is measured. This is inherently different from all other techniques and devices and methods previously utilized to evaluate knee joint laxity. Simply put, the tibia retention assembly does not squeeze tightly on the lower leg, but leaves gaps between the assembly and the anterior, posterior, medial, and lateral aspects of the proximal low leg. Squeezing tightly on the proximal low leg makes it more difficult to accurately measure motion of the tibia itself, as the act of squeezing the proximal low leg causes compression of soft tissues thus resulting in greater soft tissue artifact or error in the measurements of tibial motion. Squeezing makes it more difficult to differentiate motion of the tibia from motion of the skin, muscle, adipose, etc. On the contrary, by perturbing the tibia in a given direction, only one aspect of the low leg is compressed, thus allowing accurate measurements of tibial motion relative to the femur. It is for this reason that this system has demonstrated excellent reliability (ICC>0.87) with accuracies of ±0.3 mm and ±0.5°.

Once the patient is properly positioned in the RKT apparatus 10, the RKT apparatus 10 simultaneously cycles both knees into 1) internal and external rotation, 2) anterior and posterior translation, and 3) varus and valgus rotations. Each test can be performed individually or performed in any combination or order of the three motions.

Each of these three motions may be tested separately. For each motion, three cycles of each motion are performed to precondition the structures of the knee, and both the amount of torque applied and the rate at which the torque was applied are controlled by the system. Following the three preconditioning cycles, three test cycles are performed with the magnitude, direction, and rate of force/torque application as well as motion of the tibia relative to the femur being collected. Each of the three motions will now be discussed individually.

Internal and External Rotation

First, according to various embodiments, the patient is suitably positioned within the RKT apparatus 10, and patient's feet are ensured to be suitably strapped into the corresponding Foot Rotation Assemblies 200. Each of the knee support/stabilizing assemblies are configured in stabilizing mode (clamp assembly 66 in place, see, for example FIG. 21) and adjusted such that the knee is suitably stabilized. As each of the two pivoting leg support frame assemblies 50 is free to pivot relative to the sliding support framework 40, the legs of the patient, the two pivoting leg support frame assemblies 50 thus tend to be aligned according to the patient's natural alignment. Improper alignment would pretension ligaments thus creating error in the test results. All adjustments are then complete and the patient is then ready to be tested.

According to various embodiments, the knee is preconditioned by performing at least three complete rotational cycles. Following the 3 preconditioning cycles, 3 additional test cycles will be performed and the data from these test cycles will be used for analysis. Of course, it should be understood that in other envisioned embodiments, any of a variety of cycles or testing programs may be employed, as desirable for a particular application.

After such preconditioning, the RKT apparatus 10 then provides torque first in tibial external rotation at a velocity of 5°/sec until the desired torque threshold of 6 N-m is reached.

The RKT apparatus 10 then reverses direction until the threshold is reached in internal rotation, thus completing one cycle. The RKT again reverses direction and repeats this process for two additional cycles. The number of cycles performed can be increased or decreased as necessary and the torque threshold and test velocity can also be individually adjusted if deemed appropriate. Testing for internal and external rotation is thus complete.

Anterior and Posterior Translation

First, the patient is suitably positioned within the RKT apparatus 10, and patient's feet are ensured to be suitably strapped into the corresponding Foot Rotation Assemblies 200. Each of the knee support/stabilizing assemblies are configured in stabilizing mode (clamp assembly 66 in place) and adjusted such that the knee is suitably stabilized. As each of the two pivoting leg support frame assemblies 50 is free to pivotably relative to the sliding support framework 40, the legs of the patient, the two pivoting leg support frame assemblies 50 thus tend to be aligned according to the patient's natural alignment. Improper alignment would pre-tension ligaments thus creating error in the test results. The pivoting frame 162 is adjusted to control the location of force application so that force is applied with the tibia containing assembly 180 in a location that proximal to the gastrocnemius muscle belly and distal to the tibial tuberosity. The position is then maintained by tightening clamp 163. The tibia containing assembly 180 is then adjusted so that the pads 189 are located 1 cm away from both the anterior aspect of the tibia and the posterior aspect of the gastrocnemius. This adjustment is made using adjustment rods 184 and the position is maintained by tightening clamp 186. According to certain embodiments, all adjustments are then complete and the patient is then ready to be tested. In other embodiments having an alternative tibia containing assembly 1180 having a plurality of bladders 1190 contained within cuffs (e.g., pads substantially similar to pads 189) further adjustment of the bladders (e.g., by inflation and/or deflation thereof) may be completed prior to performing patient testing.

The knee is preconditioned by performing 3 complete rotational cycles. Following the 3 preconditioning cycles, 3 additional test cycles will be performed and the data from these test cycles will be used for analysis.

During both preconditioning and test cycles, the RKT apparatus 10 provides torque first in anterior translation at a velocity of 1 mm/s (The 1 mm/s was based on the velocity at the knee joint of an average male using accepted anthropometric normative values.) until the desired force threshold is reached. The RKT apparatus 10 then reverses direction until the threshold of 223 N is reached in posterior translation, thus completing one cycle. In anterior translation, the applied force takes into account the patient's height and weight, equaling 134 N in addition the force necessary to raise the mass of the low leg. The weight of the low leg can be estimated based on the patient's height and weight based on accepted anthropometric measures. For example, the force necessary to raise a low leg that weighs 20 lb is 89 N. The force threshold is then 134 N plus 89 N, for a total of 223 N.

The RKT again reverses direction and repeats this process for two additional cycles. The number of cycles performed can be increased or decreased as necessary and the force threshold and test velocity can also be individually adjusted if deemed appropriate. Testing for anterior and posterior translation is thus complete.

Varus and Valgus Rotation

The knee is preconditioned by performing 3 complete varus-valgus cycles. Following the 3 preconditioning cycles, 3 additional test cycles will be performed and the data from these test cycles will be used for analysis.

After such preconditioning, the RKT apparatus 10 then provides torque first in varus rotation at a velocity of 1°/sec until the desired torque threshold is reached. Under one method, the torque threshold is calculated based on the patient's height and weight, and is equal to 1 N-m per unit of Body Mass Index ($kg/m^2$). Alternately, the torque threshold could be based on the patient's height and weight and/or BMI, or a fixed torque threshold of 7 or 12 N-m could be used as has been done in previous studies.

Since there is a frictional component of the slide attached to the knee pedestal and since the force is being applied at varying lever lengths based on patient height, we are increasing/decreasing the force based on patient height and weight in order to apply enough force to move the joint in this plane. The RKT apparatus 10 then reverses direction until the threshold is reached in valgus rotation, thus completing one cycle. The RKT again reverses direction and repeats this process for two additional cycles. The number of cycles performed can be increased or decreased as necessary and the torque threshold and test velocity can also be individually adjusted if deemed appropriate. Testing for varus-valgus rotation is thus complete.

Testing for varus and valgus rotation according to various embodiments is thus complete.

Sensing Devices and Methods of Use

As shown in at least FIG. 35, a Sensor Cluster 1000 is shown. This sensor cluster in various embodiments anticipates the use of electromagnetic motion tracking system consisting of an electromagnetic transmitter and 4 to 6 (or any of a variety number of) electromagnetic sensors. The electromagnetic system outputs the location and orientation of each sensor, and a custom software is used to calculate the six degree of freedom kinematics of the knee during laxity testing. The tracking system and custom software allow for accurate and clinically meaningful measurements of motion of the tibia relative to the femur. In further embodiments, the motion tracking system is a Polaris Spectra® system manufactured by Northern Digital Inc., of Waterloo, Canada. The Polaris® System uses a camera to measure three-dimensional positions and orientations of retro-reflective markers placed on a patient. The reflective markers are affixed to rigid arrays that are then applied to the patient's thigh, low leg, and foot. The Polaris® system is able to determine the position and orientation of each of the rigid arrays in space, and therefore the relative position and orientation of the patient's knee. It is able to measure joint motion in six degrees of freedom, meaning that it can determine both rotation and translation of the joint about all three planes of motion. In additional embodiments, opto-electronic tracking devices may be used, which emit optical signals that are received by a camera and the camera is configured to follow the three-dimensional position of each sensor, thus allowing for the determination of the three-dimensional position and orientation with respect to one another of the various bones.

In further embodiments, ultrasonic devices may be used. These devices determine their three-dimensional position and orientation with respect to one another.

In addition to conventional motion tracking systems that feature skin-based sensors or markers, this system could be used in conjunction with medical imaging systems to evaluate relative motion between the tibia and femur. The materials of the device could be made from non-ferrous materials to allow use with medical imaging systems, which may include, but are not limited to, computed tomography (CT), magnetic resonance imaging (MRI), positron emission tomography (PET), bone scintigraphy (bone scan), dual energy X-ray absorptiometry (DEXA), diagnostic ultrasound, fluoroscopy, radiography, or other imaging methods.

In addition to using external devices to measure the relative motion between the tibia and the femur, external measurement devices can be incorporated within the system as a direct measure of the force or torque being applied to the joint. In one embodiment, the assembly that perturbates the tibia into anteroposterior translation and varus-valgus rotation can be made with a plurality of inflatable air cuffs. These air cuffs may be individually attached to pressure sensors so that as force is applied to the leg, the change in pressure is recorded and used for later analysis. The air cuffs may also be attached in series since only one cuff is being compressed at a time in order to reduce the number of pressure sensors needed to capture this information.

During the internal/external rotation portion of the diagnostic routine, an external reaction torque transducer may be incorporated between the foot plate and the output shaft from the motor or gearhead. These transducers will then record the torque being applied in regular intervals throughout, and then be used for later analysis.

Special Comment Regarding Perturbation of Intermediate Joint

Note that one feature of the present apparatus and method applies to a 'perturbation' type of evaluation across every joint. For instance, the pelvis could be held in a clamp or device and the torso rotated at the thorax by a brace. All of the intercalary segments between the thorax and the pelvis would then be subjected to a rotational force. A CT scan could then follow accurately measuring/recording the motion that occurs between each of the segments. A known force is then correlated with a known motion and a load-deformation curve is constructed describing the relationship between these intercalary bones. The same could be of the elbow, wrist, shoulder, ankle, and hip. Fingers could also be evaluated. The 'perturbation' technique is safe and opens up an entirely new way of testing.

Uses of the Above Devices with Subjective Measurement Modules, Such as 2000, 2100 or 2200

Reference is now made to subjective measurement modules 2000, 2100, and 2200 shown in FIG. 17, FIG. 36, and FIG. 18, respectively.

FIG. 17 shows a subjective measurement module 2000 including a subjective measurement module dial 2001 (operated by the user) and an output display 2002.

FIG. 36 shows a subjective measurement module 2100 including a subjective measurement module dial 2101 and an overall machine stop button 2102.

FIG. 18 shows a subjective measurement module 2200 including a subjective measurement module slide 2201 (operated by the user) and an output display 2202.

The device described consists of a digital potentiometer or similar device that a patient can continuously adjust to rate their current level of pain (either a 0-10 scale or "no pain" to "maximum pain" scale) during joint laxity testing. To our knowledge, no other joint laxity measurement system has the ability to capture subjective pain ratings from the patient that can then correlated with the instantaneous torque, position, and angle data being captured as part of the joint laxity examination. The ability to incorporate subjective pain ratings with the objective measures being collected with the laxity test system allows surgeons and other medical professionals to better understand the anatomic structure(s) that may be involved.

The proposed device may according to various embodiments comprise a separate hand-held pendant to be used by a patient during instrumented joint laxity testing. In certain embodiments, the device may have either a dial (see modules 2000 and 2100) or slide potentiometer (see module 2200) that a patient would adjust according to his/her pain level at any given moment. In other embodiments, the patient would be able to rate his/her pain with a single hand through the use of a hand-held device featuring either a plunger that could be depressed with the thumb and/or a lever or other "trigger" that could be depressed with the fingers. The patient could then use either depress the thumb plunger or squeeze the trigger to report increasing levels of pain and/or discomfort. Examples of hand held systems that could be used include, but are not limited to, the Aurora AFX Adjustable Control or the Omron A4EG. The Aurora device features a trigger mechanism that could be squeezed to indicate the patient's current level of pain and the Omron device features a compressible area that can be squeezed by the fingers as well as an emergency stop button that can be activated with the thumb.

According to various embodiments, the subjective ratings of pain would be output not only to the output displays shown, but also to a dedicated computer that would also be collecting torque and position data from the motors as well as the position and angle data from the three-dimensional motion tracking system. The pain ratings would be captured at regular sub-second intervals and synchronized with the torque, position, and angle data. Data could be sent from the Subjective Measurement Module to the computer by a number of means including, but not limited to direct USB cable or other cables, or wirelessly with a Bluetooth connection or other wireless means.

The patient's pain rating may be output to a visual display on the pendant in real time. Pain ratings could either be displayed using a numeric display or graphical display. The numeric display (see e.g., FIG. 17) could range from 0.0 to 10.0, with 0 representing "No Pain" and 10 representing "Max Pain". The graphical display (see e.g., FIG. 18) may use a scrolling horizontally-directed line to indicate pain (y-axis) as a function of time (x-axis).

The pain measurement device may according to various embodiments also be used as an additional safety measure for the laxity system, such that when the patient indicates maximum pain or pain above a pre-determined threshold (8 out of 10 for example), then the motors applying the torque would either reverse direction or be disengaged. This threshold could vary in intensity for different tests or patient profiles, as some patients will perceive pain differently from others. In embodiments that feature multiple methods for patient input, one input could be used to rate pain and the other input be used as an emergency stop for the knee testing system. For example, the subjective measurement module 2100 (see e.g., FIG. 36) features two such patient inputs. One input in certain embodiments, the subjective measurement module dial 2101, would be used by the pain to indicate his or her level of pain. The second input, stop button 2102, would then be used as an emergency stop switch that would disengage the motors and terminate a given laxity test. In the embodiment with thumb plunger and finger "trigger" patient inputs, the "trigger" could be squeezed by the patient to indicate his or her current level of pain, and the thumb plunger could be used as an emergency stop button that would disengage the motors and terminate a given laxity test.

In addition to pain ratings, the Subjective Measurement Module may according to various embodiments also be used by patients to rate other subjective measures. For example, the same 0 to 10 rating system could be used for patients to rate their sensations of instability or the feeling of "giving way", which is clinically associated with joint laxity or instability.

It should also be understood that the subjective measurement module described above could be used with other devices such as those described in U.S. Pat. Nos. 6,669,660, 6,872,186, and 7,547,289, each of which are incorporated herein by reference, as well as any other devices which provide range of motion or other similar flexion analysis and/or therapy.

Uses of the Above Devices with Medical Imaging Devices within System 3000

Overall System 3000

Reference is first made to FIG. 39, which shows certain elements of a system 3000 according to various embodiments for providing accurate and reliable dynamic evaluation of joint play. According to various embodiments, the system is composed of a stabilizing assembly 3010 placed proximal to the joint being evaluated, a distal assembly 3020 that allows for dynamic manipulation of an intermediate joint through the use of computer-controlled motorized torque application, device or devices to allow for the measurement of the magnitude and/or rate of torque application, and a medical imaging system 3030 placed intermediate to the proximal stabilizing assembly and distal assembly to allow for accurate measurement of joint play or motion, including, but not limited to internal and external rotation, flexion and extension rotation, and varus and valgus rotation.

The methods and devices may be used to test an individual joint, but may also be used for simultaneous bilateral joint evaluation. The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements.

Proximal Stabilizing Assembly 3010

According to various embodiments, the proximal stabilizing assembly 3010 comprises an apparatus that is generally configured to grasp the leg(s) of the patient approximately above each knee(s), as shown in at least FIG. 39. It should be understood that while the assembly 3010, as illustrated, is configured to grasp the patient/user's leg(s), such may be alternatively configured to grasp any of a variety of limb and/or joint portions (e.g., the non-limiting examples of wrist, forearm, upper arm, elbow, shoulder, thorax, etc.), as may be desirable for a particular application.

The function of the stabilizing assembly 3010 according to various embodiments is to substantially limit or direct motion of the proximal segment while the intermediate joint of the body is manipulated. In certain embodiments, the assembly 3010 may be free-standing, but may in other embodiments also be fixed to the moveable gantry of medical imaging devices. In at least the embodiment depicted in FIG. 39, the assembly 3010 is customized to be slotably inserted into the gantry of a computed tomography (CT) scanner for the use of evaluating the human patellofemoral joint. In at least that embodiment and other envisioned embodiments, the proximal stabilizing assembly may be slotably inserted into the gantry of a CT scanner, and may be rigidly locked into place relative to the gantry. In these and still other envisioned embodiments, the assembly 3010 may feature several inferior adjustable components that allow for the patient's limb to be stabilized in its natural resting alignment.

According to various embodiments, by using the inferior adjustment components according to various embodiments, the left and right stabilizing subassemblies can be moved either medially or laterally to be appropriately positioned to the desired degree of hip abduction. In certain embodiments, the upper left and right stabilizing subassemblies can then be individually pivoted to be perpendicular to the long axis of each femur and locked into place. This allows the stabilizing pads to be placed parallel to the long axis of the femur thus avoiding uneven application of stabilizing force. In certain embodiments, the upper left and right stabilizing subassemblies can then be individually adjusted so that an appropriate stabilizing force can be applied to one or both limbs. In these and still other envisioned embodiments, such adjustments allow the individual left and right stabilizing subassemblies to be aligned according to the patient's natural alignment. Improper alignment would pre-tension ligaments thus creating error in the test results. This adjustment is made to avoid such errors.

The function of the proximal stabilizing assembly 3010 according to various embodiments as described is to direct or limit the amount of long axis rotation or mediolateral translation or rotation of the segment located proximal to the joint to be evaluated. It is important to note that an additional strap or rigid fixture may be used in conjunction with the proximal stabilizing assembly in order to direct or limit the amount of anteroposterior or cranial-caudal translation. In these and still other envisioned embodiments, the proximal stabilizing assembly and all subcomponents can be made from non-ferrous materials such in order to limit any potential metal artifacts on the created images and/or to prevent damage to the imaging systems themselves.

Distal Assembly to Allow Controlled Joint Manipulation

According to various embodiments, the distal assembly 3020 comprises an apparatus that is grasping the feet of the patient, as depicted in at least FIG. 39. In various embodiments, the functions of the distal assembly 3020 are to allow for 1) appropriate alignment of the segment distal to the joint being evaluated prior to the controlled manipulation of the joint and 2) the controlled manipulation of the joint. In this manner, much like the proximal stabilizing assembly, the distal assembly according to various embodiments does not provide direct support of the joint that is to be manipulation. This then allows to joint to move freely without being inappropriately guided or directed if there was a direct articulation between the testing system and the joint itself. It should be understood that while the distal assembly 3020, as illustrated, is configured to grasp the patient/user's feet, such may be alternatively configured to grasp any of a variety of limb and/or joint portions (e.g., the non-limiting examples of wrist, ankle, pelvis, elbow, shoulder, etc.), as may be desirable for a particular application.

The distal assembly 3020 according to various embodiments has several adjustments that can be made to properly position the limb for testing. In certain embodiments, the entire assembly can be slidably moved along a track near the floor that is in-line with the long axis of the body to position the system for testing and for repositioning the system to a position at which it will not interfere with the conventional use of the imaging system when not in use. When positioned in at least these embodiments for use in the evaluation, the assembly 3020 may be locked or clamped into a fixed position to prevent motion of the entire apparatus during testing if desired. In this way the system can be used to maintain a fixed position on the floor during testing, or can be allowed to move along the track near the floor if it is so desired during testing. However, it should be understood that in still other envisioned embodiments the assembly 3020 may or may not be locked or clamped into a fixed position, as may be desirable for a particular application. These and related concepts will be discussed in more detail in the following section related to the method of capturing and analyzing the images.

According to various embodiments, once the assembly 3020 is positioned along the track near the floor for testing, several other adjustments may be made to accommodate a patient's leg length and natural alignment as well as the desired joint angles necessary for joint evaluation. In certain embodiments, the left and right aspects of the main assembly can be moved along a track that is perpendicular to the long axis of the body to accommodate varying degrees of knee varus or valgus alignment and can be locked into place. In at least one embodiment, the left and right aspects of the main assembly can be individually aligned, or in the case of bilateral evaluation, can be fixed to one another with a rigid cross-member in order to allow both assemblies to be positioned at the same degree of knee varus/valgus alignment. However, it should be understood that in still other envisioned embodiments, the left and right aspects of the main assembly may be otherwise configured, as may be desired for a particular application.

Similarly, according to various embodiments, a clamp may be is located on the vertical rod for both the left and right aspects of the main assembly. The entire manipulation assembly (the motor/foot plate combination that is used to actually manipulate the joint) can then be moved superiorly or inferiorly in order to change the relative degree of knee flexion or extension. The left and right manipulation assemblies can be individually aligned, or in the case of bilateral evaluation, can be fixed to one another with a rigid cross-member in order to allow both assemblies to be positioned at the same degree of knee extension. The clamping mechanism also allows for the long axis of the manipulation assembly to be pivoted medially or laterally in order to align the axis of rotation with the long axis of the body segment distal to the joint being manipulated. The inability to make the adjustment would create a situation in which the torque being applied would not be in-line with the physiologic motion of the joint, resulting in measurement errors. The clamping mechanism can then be tightened to maintain proper alignment throughout the test.

A second clamping mechanism according to various embodiments may be located on the vertical rod for both the left and right aspects of the main assembly allows for the system to be adjusted for the patient's individual limb length. When loosened, the clamp allows for the elongate member attached to the manipulation assembly to be translated cranially or caudally in order to position the foot on the manipulation assembly. In addition, when loosened, the clamp allows for the manipulation assembly to be pivoted up or down to align the axis of rotation with the long axis of the body segment distal to the joint being manipulated. The inability to make the adjustment would create a situation in which the torque being applied would not be in-line with the physiologic motion of the joint, resulting in measurement errors. The clamping mechanism can then be tightened to maintain proper alignment throughout the test.

It should be noted that one or more axis of rotation can be evaluated using this system. Motors mounted perpendicular to the long axis of the distal segment on the manipulation assembly will allow for the evaluation of flexion/extension rotation and/or varus/valgus rotation.

Measurement of the Magnitude and/or Rate of Torque Application

The remainder of the manipulation assembly is similar in form and function to our apparatus previously described in U.S. Patent Application 2009/0124936. The computer-controlled motorized system allows for the consistent application of torque, and also features measurement devices that allow the magnitude of the torque and rate of torque application to be measured at routine intervals throughout the dynamic test.

Method of Using Computer-Controlled Motorized Manipulation System with Medical Imaging Systems Once the user has been secured by the proximal stabilizing and distal assemblies, data related to the motion of the joint can be gathered by use of the medical imaging system 3030 (such as the CT scanner with the central pass-through hole in the middle shown in FIG. 39, shown in a approximated position needed to evaluate the knee region(s). In certain embodiments, positioning of the user is such that he or she is positioned supine with both knees resting in 20 degrees of flexion. However, alternative positioning may be envisioned for either the knee or any of a variety of other joints (e.g., pelvis, shoulder, elbow, wrist, fingers, ankle, thorax, etc.), as desirable or necessary for a particular application.

In various embodiments, a computer or other programmable controller is configured to control the motors to perform a desired diagnostic routine. For example, the diagnostic routine may comprise repeating several cycles of rotating the user's manipulation assemblies in a first direction (e.g., clockwise) from a neutral position (i.e. the foot pointing substantially upward) until a predetermined threshold is reached. Next, the user's leg may be rotated in a second direction (e.g., counterclockwise) from the neutral position until a predetermined threshold is reached for three cycles.

In other embodiments, the diagnostic routine may comprise the rotating of a user's lower leg in a clockwise direction until a predetermined threshold is met and then rotate the in a clockwise direction until a predetermined threshold is met in a substantially fluid motion. This procedure may be repeated for several cycles.

In various embodiments, both of the user's lower legs may be rotated simultaneously. For example, the user's left leg may be rotated counter clockwise (external rotation) and then clockwise (internal rotation) while the user's right leg is rotated clockwise (external rotation) and then counter-clockwise (internal rotation). By rotating the legs simultaneously in opposite directions, the movement in the hip area can be minimized since the motions counter act each other. In other embodiments, the rotation of each leg may be performed independently. In at least one embodiment, the legs may be rotated at a velocity of approximately 1.25 degrees per section, with an applied torque threshold of 6 Nm. However, it should be understood that still other envisioned embodiments may rotate the legs at any of a variety of velocities, subject to any of a variety of applied torques, as may be desirable for a particular application.

While the diagnostic routine is performed, various parameters may be monitored to evaluate the performance of the knee. In one embodiment, torque measurements are taken at regular intervals during the dynamic diagnostic routine. At the same time, images are generated of the joint using the medical imaging system 3000.

During the diagnostic routine, the CT scanner will be creating images at a high frequency, such as of 1.25 hz. A 20-mm capture volume will be imaged every 0.8 seconds throughout the dynamic test. The series of images are then used to generate three-dimensional models of the bones, thus allowing for accurate and reliable measurement of bony kinematics in six degrees of freedom (translation and rotation about three axes). For example, motion of the patella can be measured relative to the femur in order to better understand the condition surrounding ligamentous structures as well as the influence of bony morphology on the motion of the patella relative to the femur. In another embodiment, helical or spiral imaging techniques can be utilized to create images of a larger capture volume. In the example of the patellofemoral joint, the gantry can be programmed to move cranially and/or caudally throughout the course of the dynamic diagnostic routine in order to create images of the entire patella and not just a 20-mm capture volume. In this embodiment, the entire distal assembly can be allowed to slide cranially and/or caudally by the body in response to the movement of the gantry, or may be rigidly fixed to the gantry itself to allow the gantry to directly move the distal assembly.

The two time series of torque information and kinematic information can then aligned. From this data, a hysteresis curve can be generated, which may be used to evaluate the performance of the patellofemoral joint. In another embodiment, an additional non-invasive fixture can be strapped or attached to the tibia. In this embodiment, the tibial fixture features an elongate appendage that projects from the tibial fixture to the imaging device's capture volume, thus allowing for the relative motion of the tibia to be quantified. In this way, the patellofemoral kinematics can be evaluated while simultaneously generating information about how the tibia moves relative to the femur, and how the patella moves relative to the tibia.

Embodiments Related to Other Body Segments

While the above has been generally described with regard to a patient/user's leg/knee/thigh, it should be understood that system 3000 may be alternatively configured to grasp and/or perturb any of a variety of limb and/or joint portions (e.g., the non-limiting examples of wrist, forearm, upper arm, elbow, shoulder, thorax, etc.), as may be desirable for a particular application.

As a non-limiting example, it should be noted that similar methods and devices have been developed to evaluate joint play of other joints. The elbow can be evaluated in much the same way as a knee, with the opportunity to utilize one or more axes of motorized rotation distal to the hand, with the upper arm(s) being supported using a proximal stabilizing assembly. This will allow for varus/valgus, flexion/extension, or pronation/supination laxity of the elbow to be evaluation, which are all vital to understanding the condition of the elbow following ligamentous injury, radial head fractures, and any number of other orthopaedic injuries to the joint.

In much the same way, the ankle, hip, wrist and shoulder can be dynamically evaluated by stabilizing the proximal segment and using a distal assembly with computer-controlled motor(s) to manipulate the joint while measuring information about the applied torque as well as joint motion through the use of medical imaging techniques. Furthermore, the distal assembly can be easily modified to allow for dynamic evaluation of the lumbar, thoracic, or cervical spine.

IV. Conclusion

The foregoing description of the various embodiments of the present invention has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

The drawings and preferred embodiments do not and are not intended to limit the ordinary meaning of the claims in their fair and broad interpretation in any way.

What is claimed is:

1. An apparatus for evaluating leg movement characteristics of a patient, said patient having a torso, and also having a first leg extending from said torso, said leg including a femur, patella, tibia, and a foot distal relative to said tibia and pivotably attached at an ankle joint relative to said tibia, said apparatus comprising:

A) a base assembly configured to at least partially support said torso; and

B) a leg support assembly independently pivotably mounted about a pivot axis relative to said base assembly, said leg support assembly configured to at least partially support a portion of said leg, said support being independent of said support of said torso, said leg support assembly including:

1) a first leg support member comprising a foot rotation assembly rotating about at least one axis of rotation relative to said base assembly, said foot rotation assembly configured to at least partially retain and support a portion of said foot of said patient and to cooperate within said first leg support member so as to rotate said foot portion relative to said base assembly, said axis of rotation of said foot rotation assembly lying in a plane substantially parallel to said pivot axis of said leg support assembly, and said axis of rotation of said foot rotation assembly being distally spaced from the entirety of said foot and in a more distal position than the entirety of said foot, the entirety of said foot being positioned intermediate said pivot axis of said leg support assembly and said plane of said axis of rotation of said foot rotation assembly; and 2) a second leg support member configured for supporting a portion of said leg at a location proximal relative to said first leg support member during said rotation of said foot, said foot rotation assembly configured to rotate said associated foot about said axis of rotation such that an associated leg movement is provided and can be measured.

2. An apparatus for evaluating leg movement characteristics of a patient, said patient having a torso, and also having a first and a second leg extending from said torso, each leg including a femur, patella, tibia, and a foot distal relative to said tibia and pivotably attached at an ankle joint relative to said tibia, said apparatus comprising:

A) a base assembly configured to at least partially support said torso; and

B) first and second leg support assemblies each independently pivotably mounted about a pivot axis relative to said base assembly, each leg support assembly configured to at least partially support a portion of a respective one of said first and second legs, said support being independent of said support of said torso, each of said leg support assemblies including:

1) a first leg support member comprising a foot rotation assembly rotating about an axis of rotation, said foot rotation assembly configured to at least partially retain and support a portion of an associated foot of said patient and to cooperate with said leg support member so as to rotate said foot portion relative to said base assembly, said axis of rotation of said foot rotation assembly lying in a plane substantially parallel to said pivot axis of said leg support assembly, and said axis of rotation of said foot rotation assembly being distally spaced from the entirety of said foot and in a more distal position than the entirety of said foot, the entirety of said foot being positioned intermediate said pivot axis of said leg support assembly and said plane of said axis of rotation of said foot rotation assembly; and 2) a second leg support member configured for supporting a portion of said leg at a location proximal relative to said first leg support member during said rotation of said foot, each said foot rotation assembly configured to rotate said associated foot about said axis of rotation such that an associated leg movement is provided and can be measured.

3. The apparatus as claimed in claim 2, wherein said first and second leg support assemblies pivot relative to said base about substantially parallel axes.

4. The apparatus as claimed in claim 3, wherein said pivot axes are substantially vertical.

5. The apparatus as claimed in claim 2, wherein said second leg support member is a knee support member.

6. The apparatus as claimed in claim 5, further comprising a third leg support member, being a thigh retention assembly configured to retain the upper leg of said patient so as to at least partially restrict movement of said femur relative to said foot during rotation of said associated foot relative to said femur.

7. The apparatus as claimed in claim 2, wherein said second leg support member is a thigh retention assembly configured to retain the upper leg so as to at least partially restrict movement of said femur relative to said foot during rotation of said associated foot relative to said femur.

8. The apparatus as claimed in claim 7, wherein said thigh retention assembly is configured to be laterally adjustable relative to the longitudinal axis of the associated thigh, so as to accommodate a patient's particular valgus/varus knee condition.

9. The apparatus as claimed in claim 2, wherein said base assembly includes:
a main frame assembly including a torso support portion; and
a sliding support framework providing independent pivoting support of said first and second leg support assemblies relative to said base assembly such that said first and second leg support assemblies are supported by and may be pivoted relative to said base assembly,
said sliding support framework slidably mounted along a linear axis relative to said base assembly, such that said sliding support framework, and both of said leg support assemblies pivotably supporting thereon, may be slidably adjusted relative to said torso support portion.

10. The apparatus as claimed in claim 2, wherein said foot rotation assembly is mounted in a three axis gimbal configuration relative to said base assembly to at least partially capture and support an associated foot of said patient and to said foot about three separate axes, being substantially mutually perpendicular to each other.

11. A method for evaluating leg movement characteristics of a patient, said patient having a torso, and also having a first and a second leg extending from said torso, each leg including a femur, patella, tibia, and a foot distal relative to said tibia and pivotably attached at an ankle joint relative to said tibia, said method comprising the steps of:
A) providing an apparatus comprising:
1) a base assembly configured to at least partially support said torso; and
2) first and second leg support assemblies each independently pivotably mounted about a pivot axis relative to said base assembly, each leg support assembly configured to at least partially support a portion of a respective one of said first and second legs, said support being independent of said support of said torso, each of said leg support assemblies including:
a) a first leg support member including a foot rotation assembly rotating about an axis of rotation, said foot rotation assembly configured to at least partially retain and support a portion of an associated foot of said patient and to cooperate with said leg support member so as to rotate said foot about an axis of rotation relative to said base assembly, said axis of rotation of said foot rotation assembly lying in a plane substantially parallel to said pivot axis of said leg support assembly, and said axis of rotation of said foot rotation assembly being distally spaced from the entirety of said foot and in a more distal position than the entirety of said foot, the entirety of said foot being positioned intermediate said pivot axis of said leg support assembly and said plane of said axis of rotation of said foot rotation assembly; and
b) a second leg support member configured for supporting a portion of said leg at a location proximal relative to said first leg support member during said rotation of said foot; and
B) placing a patient in said device, rotating said associated foot about said axis of rotation such that said associated leg movement is provided, and measuring said movement.

12. The method as claimed in claim 11, further comprising the step of using a subjective pain device to affect operation of said apparatus, wherein said user is able to provide the user's subjective feedback to pain being encountered during said method.

13. The method as claimed in claim 11, wherein step "B" also includes measuring a force required to rotate said foot.

14. The method as claimed in claim 11, wherein step "B" includes rotating said foot first in a first direction, and then in a second, substantially opposite, direction.

15. The method as claimed in claim 11, wherein step "B" includes rotating said foot about an axis that is substantially perpendicular to the longitudinal axis of the tibia of the patient.

16. The apparatus as claimed in claim 1, wherein said axis of rotation of said foot rotation assembly is parallel to said pivot axis of said leg support assembly, such that Varus/Valgus type Rotation may be provided.

17. The apparatus as claimed in claim 1, wherein said axis of rotation of said foot rotation assembly is perpendicular to said pivot axis of said leg support assembly, such that Anterior/Posterior type Translation may be provided.

18. The method as claimed in claim 11, wherein one of either Anterior/Posterior type Translation or Varus/Valgus type Rotation is provided during said rotation of said foot about said axis of rotation.

19. The method as claimed in claim 11, wherein Anterior/Posterior type Translation is provided during said rotation of said foot about said axis of rotation.

20. The apparatus as claimed in claim 11, wherein said axis of rotation of said foot is perpendicular to said pivot axis of said leg support assembly such that Anterior/Posterior type Translation may be provided.

21. The apparatus as claimed in claim 11, wherein said axis of rotation of said foot is parallel to said pivot axis of said leg support assembly such that Varus/Valgus type Rotation may be provided.

22. A method for evaluating leg movement characteristics of a patient, said patient having a torso, and also having a first leg extending from said torso, said leg including a femur, patella, tibia, and a foot distal relative to said tibia and pivotably attached at an ankle joint relative to said tibia, said method comprising the steps of:
- A) providing an apparatus comprising:
  1) a base assembly configured to at least partially support said torso; and
  2) a leg support assembly independently pivotably mounted about a pivot axis relative to said base assembly, said leg support assembly configured to at least partially support a portion of said leg, said support being independent of said support of said torso, said leg support assembly including:
     a) a first leg support member comprising a foot rotation assembly rotating about an axis of rotation, said foot rotation assembly configured to at least partially retain and support a portion of said foot of said patient and to cooperate within said leg support member so as to rotate said foot portion relative to said base assembly, said axis of rotation of said foot rotation assembly lying in a plane substantially parallel to said pivot axis of said leg support assembly, and said axis of rotation of said foot rotation assembly being distally spaced from the entirety of said foot and in a more distal position than the entirety of said foot, the entirety of said foot being positioned intermediate said pivot axis of said leg support assembly and said axis of rotation of said plane of said foot rotation assembly; and
     b) a second leg support member configured for supporting a portion of said leg at a location proximal relative to said first leg support member during said rotation of said foot, and
- B) placing a patient in said device, rotating said associated foot about said axis of rotation such that said associated leg movement is provided, and measuring said movement.

23. An apparatus for evaluating leg movement characteristics of a patient, said patient having a torso, and also having a first leg extending from said torso, said leg including a femur, patella, tibia, and a foot distal relative to said tibia and pivotably attached at an ankle joint relative to said tibia, said apparatus comprising:
- A) a base assembly; and
- B) a leg support assembly mounted relative to said base assembly, said leg support assembly configured to at least partially support a portion of said leg, said leg support assembly including:
  1) a leg support member including a foot rotation assembly rotates about a foot axis of rotation, said foot rotation assembly configured to at least partially retain and support a portion of said foot of said patient and to cooperate within said leg support member so as to rotate said foot about a foot axis of rotation relative to said base assembly, said foot axis of rotation of said foot rotation assembly configured to provide internal and external rotation of said foot; and
  2) a tibia positioning assembly portion including a tibia axis of rotation, said tibia axis of rotation being distally spaced from the entirety of said foot in a more distal position than the entirety of said foot, said tibia positioning assembly portion configured to contact the lower leg portion of said associated leg at a location generally proximate said tibia and also configured to urge said lower leg portion about said tibia axis of rotation relative to said base assembly such that anterior/posterior type translation of the tibia is provided, said pivoting of said foot rotation assembly about said foot axis of rotation being independent relative to said pivoting of said tibia positioning assembly portion about said tibia axis of rotation, in that one may pivot while the other may not.

24. An apparatus for evaluating leg movement characteristics of a patient, said patient having a torso, and also having a first leg extending from said torso, said leg including a femur, patella, tibia, and a foot distal relative to said tibia and pivotably attached at an ankle joint relative to said tibia, said apparatus comprising:
- A) a base assembly configured to at least partially support said torso; and
- B) a leg support assembly independently pivotably mounted about a pivot axis relative to said base assembly, said leg support assembly configured to at least partially support a portion of said leg, said support being independent of said support of said torso, said leg support assembly including:
  1) a first leg support member including a foot rotation assembly rotating about a foot axis of rotation, said foot rotation assembly configured to at least partially retain and support a portion of said foot of said patient and to cooperate with said leg support member so as to rotate said foot about an axis of rotation relative to said base assembly;
  2) a second leg support member configured for supporting a portion of said associated leg at a location proximal relative to said first leg support member during said rotation of said foot; and
  3) a tibia positioning assembly portion including a tibia axis of rotation and configured to contact the lower leg portion of said associated leg at a location generally proximate said tibia and intermediate that of said first and second leg support members and also configured to urge said lower leg portion about said tibia axis of rotation relative to said base assembly, said tibia axis of rotation of said tibia positioning assembly portion being distally spaced from said the entirety of foot and in a more distal position than the entirety of said foot, the entirety of said foot being positioned intermediate said pivot axis of said leg support assembly and said plane of said foot rotation assembly, said foot axis of rotation of said foot rotation assembly lying in a plane substantially perpendicular to said tibia axis of rotation of said tibia positioning assembly portion, and said pivoting of said foot rotation assembly about said foot axis of rotation being independent relative to said pivoting of said tibia positioning assembly portion about said tibia axis of rotation, in that one may pivot while the other may not.

25. The apparatus as claimed in claim 24, wherein said pivoting of said foot rotation assembly about said foot axis of rotation is perpendicular to said pivoting of said tibia positioning assembly portion about said tibia axis of rotation.

26. The apparatus as claimed in claim 24, wherein said pivoting of said foot rotation assembly about said foot axis of rotation provides internal and external rotation of said foot, and wherein said pivoting of said tibia positioning assembly portion about said tibia axis of rotation provides varus valgus translation of the tibia.

27. The apparatus as claimed in claim 24, wherein said pivoting of said foot rotation assembly about said foot axis of rotation provides internal and external rotation of said foot, and wherein said pivoting of said tibia positioning assembly portion about said tibia axis of rotation provides anterior/posterior type translation of the tibia.

* * * * *